(12) United States Patent  
Smith et al.

(10) Patent No.: US 9,044,223 B2
(45) Date of Patent: Jun. 2, 2015

(54) IMPLANT INSERTION SYSTEMS AND METHODS OF USE

(75) Inventors: Daniel Joseph Smith, Dayton, NJ (US); Robert Nering, Stockton, NJ (US); Michael Nordmeyer, Pittstown, NJ (US); Jessica Liberatore, San Mateo, CA (US); Trevor Brian Akehurst, Bury St Edmunds (GB)

(73) Assignee: ETHICON, INC., Somerville, NJ (US)

( * ) Notice: Subject to any disclaimer, the term of this patent is extended or adjusted under 35 U.S.C. 154(b) by 328 days.

(21) Appl. No.: 13/488,664

(22) Filed: Jun. 5, 2012

(65) Prior Publication Data

US 2013/0324789 A1  Dec. 5, 2013

(51) Int. Cl.
*A61F 2/00* (2006.01)
*A61B 17/06* (2006.01)
*A61B 17/34* (2006.01)
*A61B 17/00* (2006.01)

(52) U.S. Cl.
CPC ....... *A61B 17/06109* (2013.01); *A61B 17/3468* (2013.01); *Y10S 128/25* (2013.01); *A61B 2017/00805* (2013.01); *A61F 2/0045* (2013.01)

(58) Field of Classification Search
USPC .............................................. 600/37, 29, 30
See application file for complete search history.

(56) References Cited

U.S. PATENT DOCUMENTS

| | | | |
|---|---|---|---|
| 5,368,602 A | 11/1994 | de la Torre | |
| 5,899,909 A | 5/1999 | Claren et al. | |
| 6,872,227 B2 | 3/2005 | Sump et al. | |
| 7,204,802 B2 | 4/2007 | De Leval | |
| 7,261,723 B2 | 8/2007 | Smith et al. | |
| 7,285,086 B2 | 10/2007 | Smith et al. | |
| 7,291,104 B2 | 11/2007 | Neisz et al. | |
| 7,611,454 B2 | 11/2009 | De Leval | |
| 8,043,205 B2 | 10/2011 | MacLean | |
| 8,092,366 B2 | 1/2012 | Evans | |
| 8,142,345 B2 | 3/2012 | Chu | |
| 2003/0149440 A1 | 8/2003 | Kammerer et al. | |

(Continued)

FOREIGN PATENT DOCUMENTS

| | | |
|---|---|---|
| GB | 2353220 | 2/2001 |
| WO | 02071953 | 9/2002 |
| WO | 2011106419 | 9/2011 |

OTHER PUBLICATIONS

"Gynecare TVT Abbrevo Continence System," Ethicon, Inc., www.ethicon.com/healthcare-professionals/products/gyncology-solutions, Jul. 1, 2013, 1 page.

(Continued)

*Primary Examiner* — Charles A Marmor, II
*Assistant Examiner* — Shannon McBride

(57) ABSTRACT

An implant insertion system includes an implant, such as a surgical mesh, having at least one insertion tip secured to the implant. Each insertion tip has a tapered distal end, a proximal end, a base extending proximally from the tapered distal end, and a central lumen formed in the base having an opening facing the proximal end of the insertion tip. The system includes an insertion device having an outer shaft and a latching assembly provided at a distal end of the outer shaft that is insertable into the opening of the central lumen for selectively locking the insertion tip to the latching assembly. The latching assembly has an outer dimension that is changeable from expanded state for locking the insertion tip to the latching assembly to a non-expanded state for unlocking the insertion tip from the latching assembly.

29 Claims, 36 Drawing Sheets

(56) References Cited

U.S. PATENT DOCUMENTS

| | | | |
|---|---|---|---|
| 2007/0015953 A1 | 1/2007 | MacLean | |
| 2008/0281148 A1 | 11/2008 | Evans et al. | |
| 2009/0137862 A1 | 5/2009 | Evans et al. | |
| 2009/0192540 A1 | 7/2009 | Chu et al. | |
| 2009/0306459 A1 | 12/2009 | De Leval | |
| 2010/0217069 A1 | 8/2010 | Meade et al. | |
| 2010/0234681 A1 | 9/2010 | Knapp et al. | |
| 2010/0256443 A1 | 10/2010 | Griguol | |
| 2011/0034759 A1* | 2/2011 | Ogdahl et al. | 600/37 |
| 2011/0230703 A1 | 9/2011 | Young et al. | |
| 2011/0297161 A1 | 12/2011 | Deitch | |

OTHER PUBLICATIONS

"Ophira Mini Sling System," Promedon, www.promedon.com, 2013, 5 pages.

"MiniArc Single-Incision Sling," American Medical Systems, www.americanmedicalsystems.com, Jul. 1, 2013, 3 pages.

"MiniArc Precise Single-Incision Sling," American Medical Systems, www.americanmedicalsystems.com, 2013, 3 pages.

"Solyx SIS System," Boston Scientific Corporation, www.bostonscientific.com/gynecology, 2009, 4 pages.

International Search Report issued for International Application No. PCT/US2013/043541, mailed Oct. 1, 2013, 9 pages.

* cited by examiner

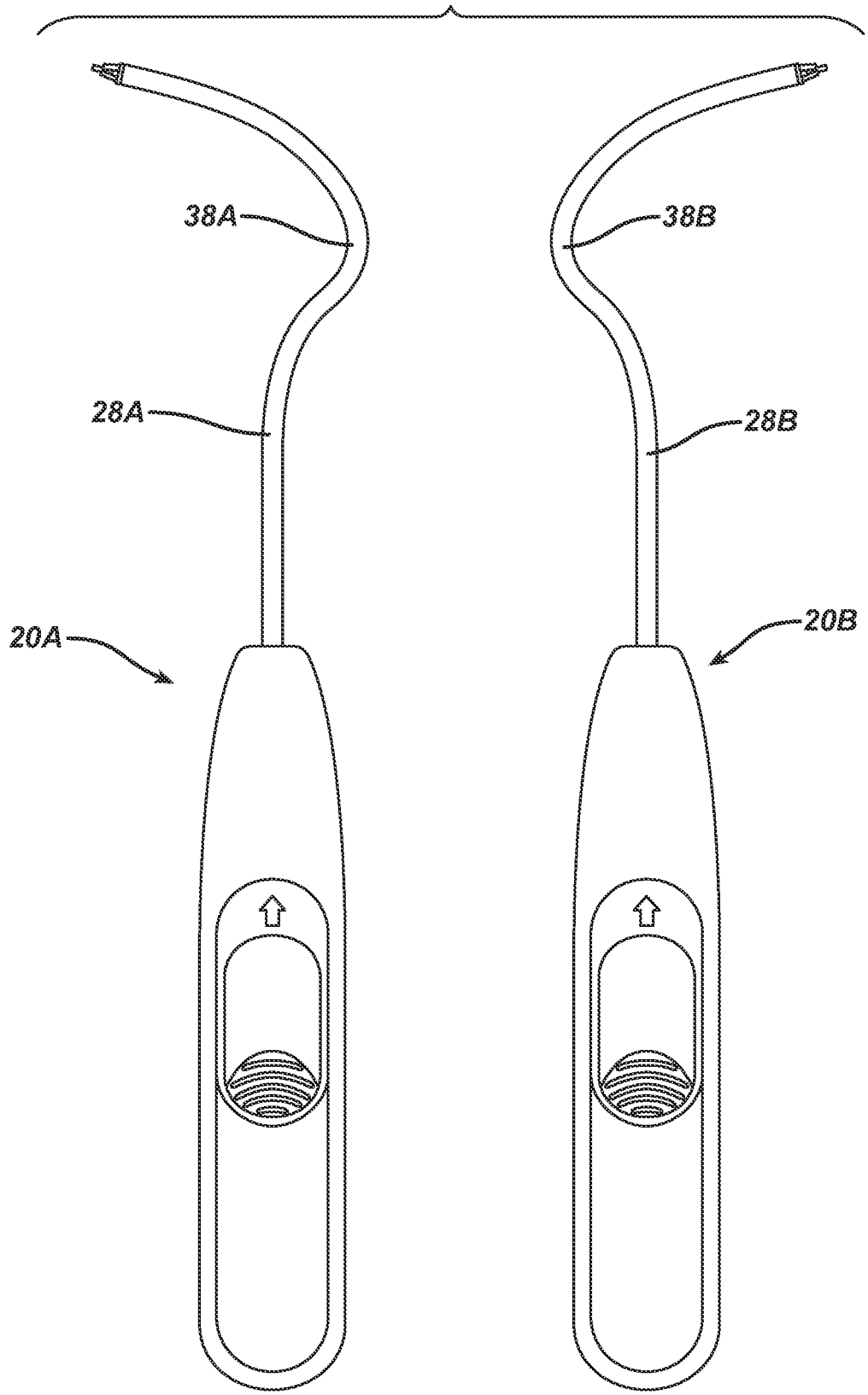

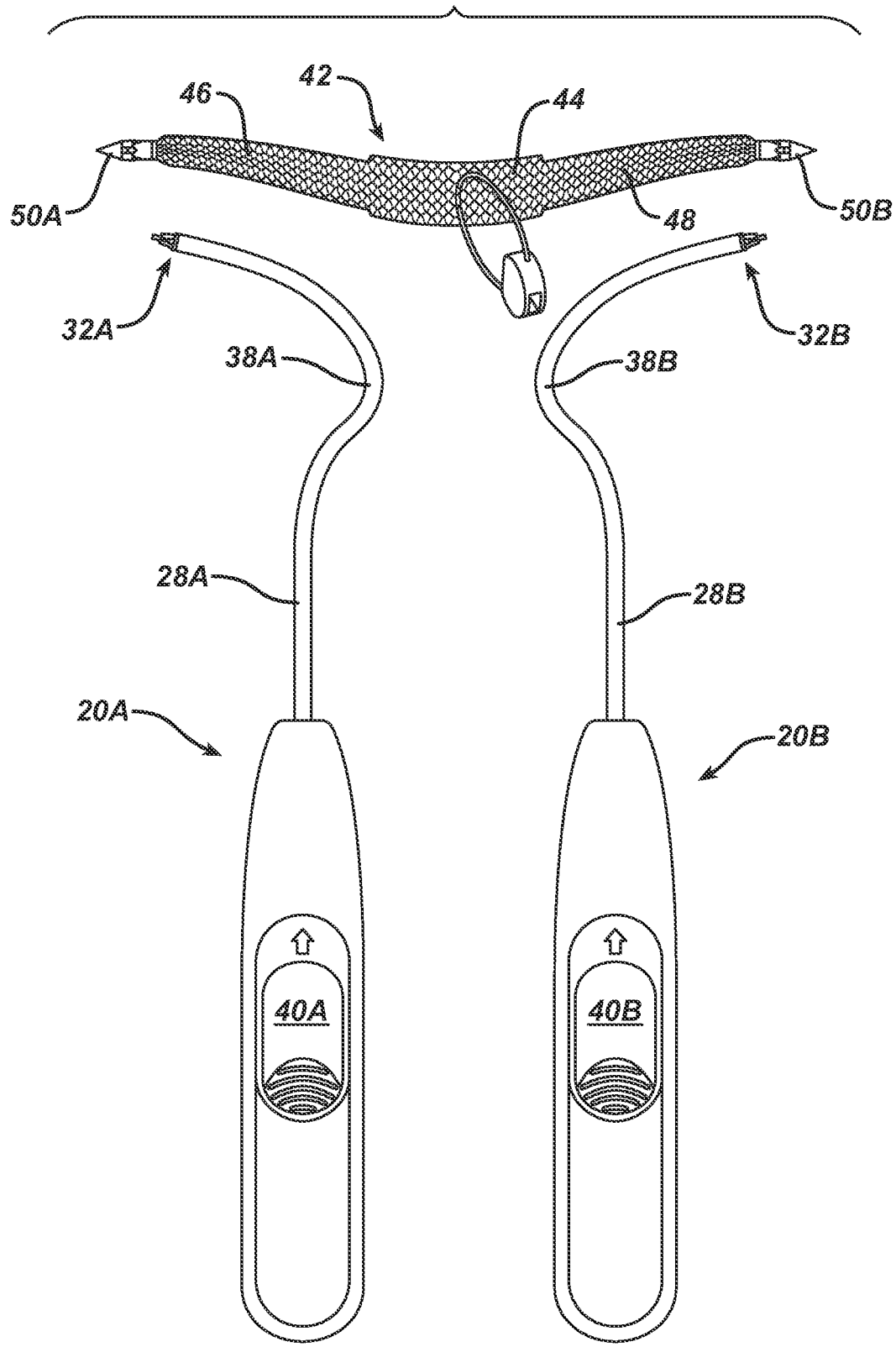

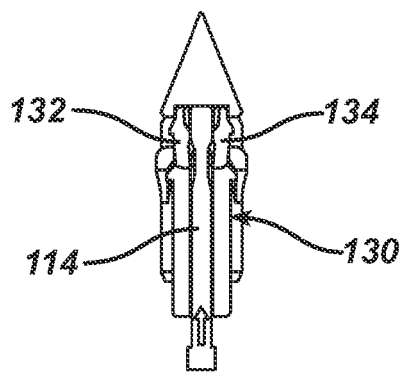
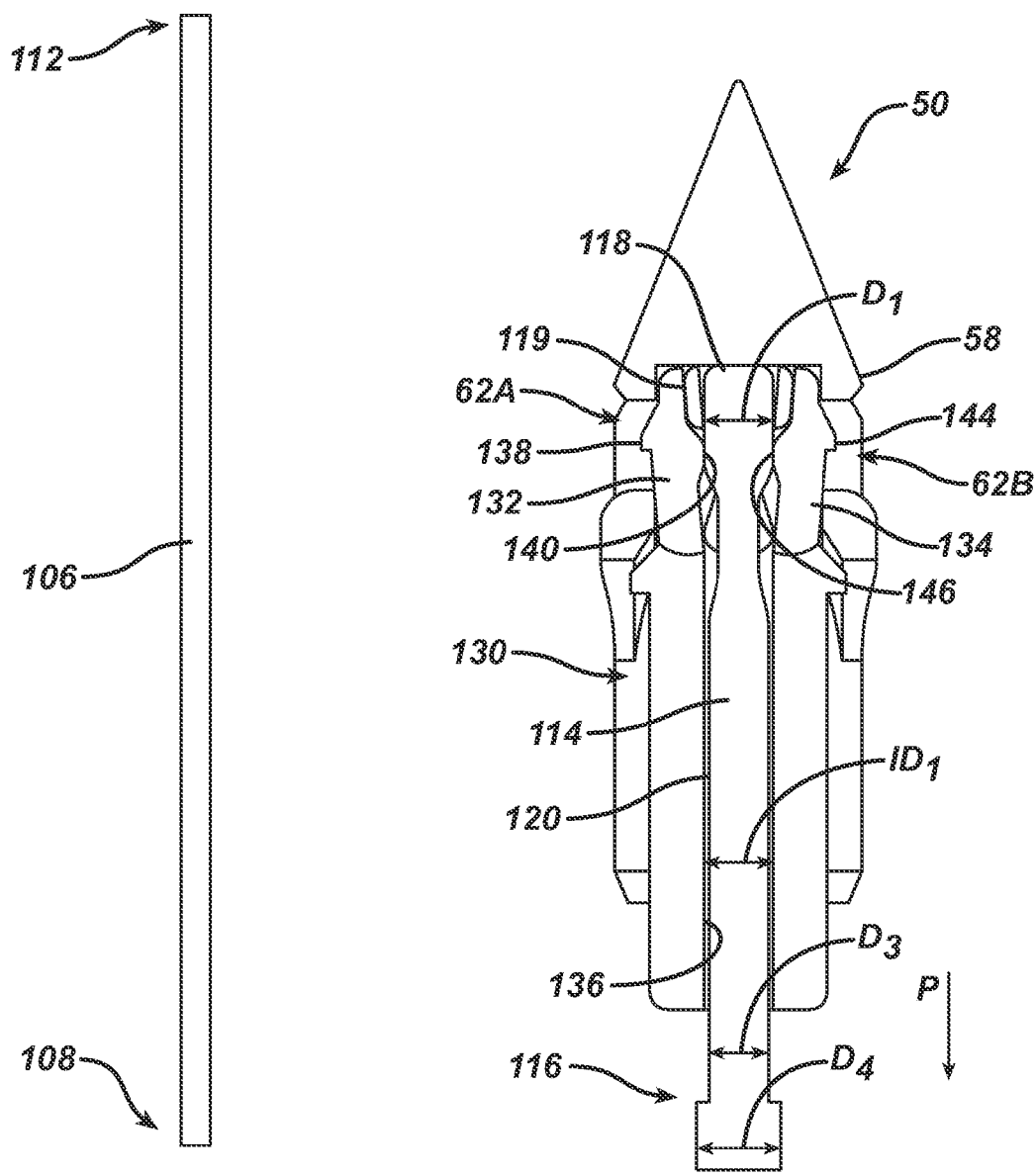

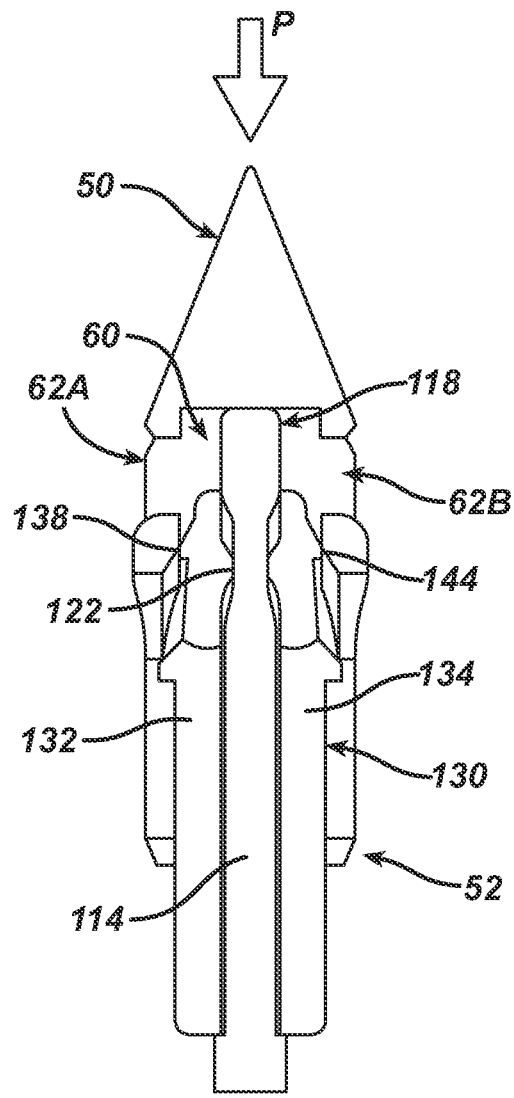 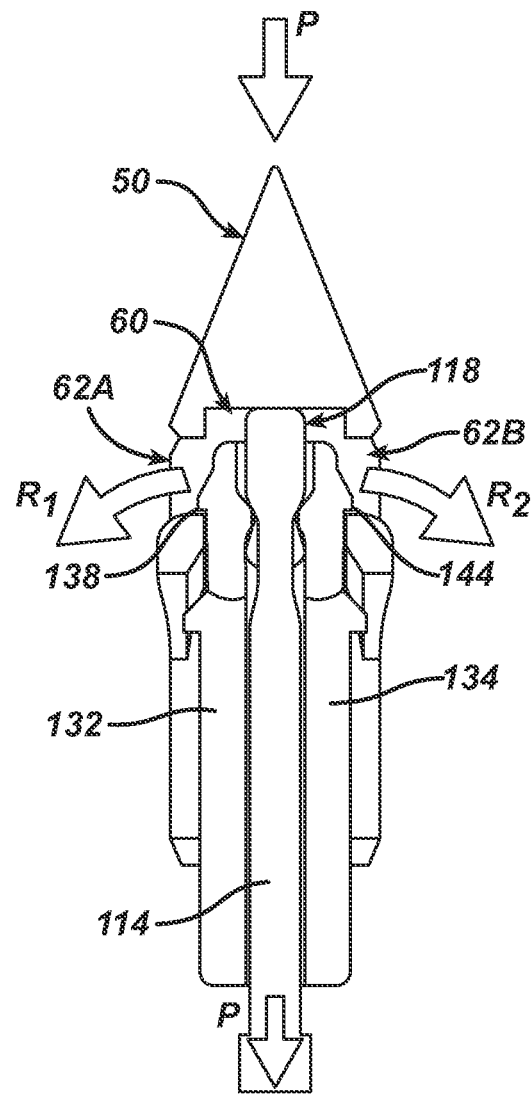
FIG. 14A  FIG. 14B

IMPLANT INSERTION SYSTEMS AND METHODS OF USE

BACKGROUND OF THE INVENTION

1. Field of the Invention

The present invention relates generally to systems, devices and methods for the treatment of female urinary incontinence, and more particularly, to systems and methods for placing a sub-urethral sling.

2. Description of the Related Art

Women account for more than 11 million incontinence cases, with a majority of those women suffering from stress urinary incontinence (SUI). Women with SUI involuntarily lose urine during normal daily activities and movements, such as laughing, coughing, sneezing and regular exercise.

SUI may be caused by a functional defect or weakened tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle and shy away from social situations.

One device and method for treating female urinary stress incontinence is described in detail in U.S. Pat. No. 5,899,909, which is incorporated herein by reference in its entirety. This patent discloses a surgical instrument comprising a shank having a handle at one end and connecting means at the other end to receive, one at a time, two curved needle-like elements which each are connected at one end to respective ends of a mesh intended to be implanted into the body. In practice, the mesh is passed into the body via the vagina first at one end and then at the other end, at one side and the other, respectively, of the urethra to form a loop around the urethra, located between the urethra and vaginal wall. The mesh is extended over the pubis and through the abdominal wall and is tightened. The mesh ends are cut at the abdominal wall, and the mesh is left implanted in the body. This trans-vaginal procedure is exemplified by the TVT product sold by Ethicon Inc., a Johnson & Johnson Company, of Somerville, N.J., USA. In this procedure two 5 mm needles pass a PROLENE mesh trans-vaginally and through the abdomen to create a tension-free support under the mid-urethra.

Sub-urethral slings have also been placed by a different approach wherein a needle is passed first though the abdominal wall along the same path as described above, and eventually exiting through the vaginal incision. The tape is then coupled to the needle in some manner, and pulled back through the body from the vaginal incision and out through the abdominal incision. The chosen approach, vaginal or abdominal, will often depend on the preferences of the surgeon.

Yet another approach for implanting a sub-urethral sling has also been recently developed in which the implanted sling extends from beneath the urethra, and out through the obturator hole on either side. This "transobturator" procedure may involve inserting an appropriately configured needle from a vaginal incision and subsequently out through the obturator hole, or vice versa. The former technique (an "inside-out" approach) and associated instruments are described in detail in U.S. Pat. Nos. 7,611,454, 7,204,802, and 7,261,723, and U.S. Patent Publication No. 2009/0306459, which are incorporated herein by reference in their entirety. As illustrated in U.S. Pat. No. 7,261,723, this technique may be performed using a surgical instrument including a surgical passer or introducer and tube elements applied over the ends of the surgical passers that are coupled to the tape to be implanted under the urethra.

More recently, sub-urethral slings that do not exit the body through the abdominal wall or the buttocks have been developed. These sub-urethral slings, sometimes referred to as "mini slings," are shorter in length and have ends that are secured inside the body into bone, tissue or the like. One embodiment of a "mini sling" is described in U.S. Pat. No. 7,285,086, the disclosure of which is hereby incorporated by reference herein.

With "mini slings" of this type, proper and accurate positioning of the distal ends within targeted tissue is essential in order to have and maintain the proper amount of support under the urethra to alleviate incontinence. One problem encountered in achieving this is that the ends of the sling must be coupled to some type of insertion device to be placed in position, then subsequently uncoupled from the insertion device so that the insertion device can be withdrawn leaving the implant in place within the body. Known insertion devices for coupling an implant to the insertion device, however, have no attachment mechanisms, have cumbersome attachment mechanisms, and/or require undesirable forces to be applied to uncouple the implant, which, in turn, frequently moves or dislodges the ends of the implant from the targeted and desired position upon uncoupling.

Thus, it would be desirable to provide an improved implant insertion system and surgical insertion devices that minimize or eliminate movement of the implant upon uncoupling of the implant from the insertion device.

SUMMARY OF THE INVENTION

In one embodiment, the present application discloses an implant insertion system including an insertion device having proximal and distal ends, an implant, and one or more insertion tips attached to the implant for advancing the implant through tissue and holding the implant at a desired location within the tissue. In one embodiment, the one or more insertion tips have distal ends that are pointed and proximal ends that are attached to the implant. In one embodiment, a proximal end of an insertion tip is secured with the distal end of the insertion device by placing the insertion tip over the distal end of the insertion device and moving the insertion tip in a proximal direction. The insertion tip is desirably secured to the distal end of the insertion device without elastically displacing any part of the insertion tip. The insertion device, with the insertion tip locked to the distal end thereof, is used for advancing the insertion tip and the implant attached to the insertion tip through tissue. After the insertion tip is positioned at a desired location within the tissue, the insertion tip is unlocked from the distal end of the insertion device without altering the position of the insertion tip or elastically displacing the insertion tip.

In one embodiment, an implant insertion system preferably includes an implant, and at least one insertion tip secured to the implant, each insertion tip having a distal end, a proximal end, a tapered point at the distal end, a base extending proximally from the tapered point, and a central lumen formed in the base having an opening facing the proximal end of the insertion tip. The system preferably includes an insertion device having an outer shaft and a latching assembly provided at a distal end of the outer shaft that is insertable into the opening of the central lumen for selectively locking the insertion tip to the latching assembly. The latching assembly has an outer dimension that is changeable from an expanded state for locking the insertion tip to the latching assembly to a non-expanded state for unlocking the insertion tip from the latching assembly.

In one embodiment, when the latching assembly is in the expanded state, the outer dimension of the latching assembly is greater than an inner dimension of the central lumen of the insertion tip for locking the insertion tip to the latching assembly. When the latching assembly is in the non-expanded state, the outer dimension of the latching assembly is less than or approximately equal to the inner dimension of the central lumen of the insertion tip for unlocking the insertion tip from the latching assembly. In one embodiment, the latching assembly, when in the non-expanded state, may form a slight interference fit with the inner dimension of the central lumen.

In one embodiment, the central lumen of the insertion tip has a width, whereby the latching assembly is wider than the width of the central lumen when the latching assembly is in the expanded state and narrower than or approximately equal to the width of the central lumen when the latching assembly is in the non-expanded state.

In one embodiment, the latching assembly has a proximal end attached to the distal end of the outer shaft, a distal end, a central opening extending between the proximal end and the distal end of the latching assembly, and first and second latches at the distal end of the latching assembly. The first and second latches preferably have respective first and second latch posts that project away from one another.

In one embodiment, one or more windows or fenestrations are formed in the base of the insertion tip. In one embodiment, first and second windows are desirably formed in opposing side walls of the base. The first and second windows preferably oppose one another, and intersect with the central lumen formed in the base of the insertion tip.

In one embodiment, the first and second latches are further apart from one another when the latching assembly is in the expanded state and are closer together when the latching assembly is in the non-expanded state. In one embodiment, the first and second latches are elastic and normally flex inwardly toward one another.

In one embodiment, when the latching assembly is in the expanded state, the first and second latch posts extend into the first and second windows in the base of the insertion tip for locking the insertion tip to the latching assembly.

In one embodiment, the system includes a tip pin disposed within the central opening of the latching assembly. The tip pin is desirably made of metal and is free to slide distally and proximally within the central opening of the latching assembly.

In one embodiment, the tip pin has a proximal end, a distal end, a shaft extending between the proximal and distal ends, a reduced diameter neck formed in the shaft, and an annular base at the proximal end of the tip pin. In one embodiment, the shaft has a first diameter, the reduced diameter neck has a second diameter that is smaller than the first diameter of the shaft, and the annular base has a third diameter that is greater than the first diameter of the shaft and greater than the diameter of the central opening of the latching assembly.

In one embodiment, the first and second latches have inner cam surfaces that slide over the outer surface of the tip pin shaft. When the latching assembly is in the non-expanded state, the distal end of the tip pin is distal to the distal end of the latching assembly and the inner cam surfaces of the first and second latches are in contact with the reduced diameter neck of the tip pin. When the latching assembly is in the expanded state, the distal end of the tip pin is aligned with the distal end of the latching assembly and the inner cam surfaces of the first and second latches are in contact with the first diameter section of the tip pin shaft adjacent the distal end of the tip pin.

In one embodiment, the insertion device includes a handle having a proximal end and a distal end with the proximal end of the outer shaft secured to the distal end of the handle. The insertion device desirably includes an actuator provided on the handle that is moveable between the proximal and distal ends of the handle. The outer shaft desirably has an elongated conduit extending between the proximal and distal ends thereof, and a push wire is disposed within the elongated conduit of the outer shaft, which is moveable in distal and proximal directions relative to the outer shaft. The push wire has a proximal end opposing the actuator and a distal end opposing the annular base of the tip pin. The push wire is not connected with the actuator or the tip pin, and is preferably free to move distally and proximally within the elongated conduit of the outer shaft. In one embodiment, the push wire may have some resistance to movement within the elongated conduit of the outer shaft, however, when an end of the push wire receives a force, the push wire remains free to move in distal and proximal directions within the outer shaft.

In one embodiment, the insertion tip is locked onto the latching assembly by placing the central lumen of the insertion tip over the distal end of the latching assembly and pushing the insertion tip toward the proximal end of the latching assembly for forcing the tip pin to move proximally, which, in turn, urges the first and second latches away from one another. As the first and second latches move away from one another, the latch posts advance into the windows formed in the base of the insertion tip for locking the insertion tip to the latching assembly.

In one embodiment, the insertion tip is unlocked from the latching assembly by moving the actuator toward the distal end of the handle, which, in turn, urges the push wire distally for contacting the annular base of the tip pin, and which, in turn, urges the tip pin distally for aligning the reduced diameter neck of the tip pin with the inner cam surfaces of the first and second latches so that the first and second latches are free to flex inwardly toward one another.

In one embodiment, the central lumen of the insertion tip has a closed end wall adjacent a distal end of the base, a top wall that defines an upper surface of the central lumen, a bottom wall that defines a lower surface of the central lumen, and opposing side walls extending between the top and bottom walls of the central lumen, whereby the first and second window openings in the base of the insertion tip extend through the side walls of the central lumen.

In one embodiment, the insertion tip preferably includes an elongated flat surface that extends proximally from the bottom wall of the central lumen to the proximal end of the insertion tip. In one embodiment, when the latching assembly is inserted into the central lumen, the latching assembly has a flat bottom surface that engages the bottom wall of the central lumen and the distal end of the outer shaft has a flat surface that engages the elongated flat surface that extends proximally from the bottom wall of the central lumen to the proximal end of the insertion tip. In one embodiment, the latching assembly is centrally located at the distal end of the outer shaft. In one embodiment, the latching assembly is not centrally located at the distal end of the outer shaft.

In one embodiment, the insertion tip has a hoop provided under the elongated flat surface adjacent the proximal end of the insertion tip. The hoop has a hoop opening for receiving an end of the implant. In one embodiment, the hoop has one or more ribs provided inside the hoop for providing frictional engagement between the hoop and the implant for attaching the implant to the insertion tip. The one or more ribs may extend only partially along the length of the hoop and not along the full length of the hoop. In one embodiment, the hoop has lead-ins to aid in pulling the mesh implant into the hoop. In one embodiment, a securing element is passed through a distal end of the hoop opening for contacting the mesh near the proximal end of the hoop opening, and the mesh is pulled into the proximal end of the hoop opening for securing the mesh to the hoop.

In one embodiment, the latching assembly has a flat top surface that engages the top wall of the central lumen of the insertion tip when the flat bottom surface of the latching assembly engages the bottom wall of the central lumen of the insertion tip.

In one embodiment, the implant has a central section and first and second arms extending from opposite sides of the central section. A first insertion tip is secured to the first arm and a second insertion tip is secured to the second arm.

In one embodiment, the system includes a first-hand insertion device, such as a left-hand insertion device, for securing the first insertion tip and a second-hand insertion device, such as a right-hand insertion device, for securing the second insertion tip.

In one embodiment, the outer shaft of the insertion device is made of metal, the handle of the insertion device is plastic, the actuator is plastic, the latching assembly is made of a polymer material, a metal, or a durable material, the tip pin is made of metal, the implant is a surgical mesh, the insertion tip is made of a polymer such as PP or PDS, and the push wire is flexible and made of stainless steel, polymers, nylon, Teflon, or polypropylene, or combinations thereof.

In one embodiment, the implant insertion system is used for treating stress urinary incontinence (SUI), whereby the implant is used in women as a sub-urethral sling for the treatment of stress urinary incontinence resulting from urethral hypermobility and/or intrinsic sphincter deficiency.

In one embodiment, an implant insertion method desirably includes providing a mesh implant having first and second insertion tips attached to the implant, securing the first insertion tip to a first insertion device without elastically displacing any part of the first insertion tip, positioning the first end of the surgical mesh implant within a patient in a first location, fixedly securing the second insertion tip to a second insertion device without elastically displacing any part of the second insertion tip, positioning the second end of the surgical mesh implant within a patient in a second location, adjusting the first and second locations relative to each other until the desired placement of the surgical mesh is achieved, and unlocking the first and second insertion tips from the respective first and second insertion devices without imparting movement of the insertion tips from their respective first and second locations and without elastically displacing the first and second insertion tips.

In one embodiment, the implant is a surgical mesh having an overall length of about 6-16 cm, and more preferably about 12 cm. In one embodiment, the surgical mesh has a central zone that is about 3 cm long×1.1 cm wide, and first and second arms having lengths of about 4.5 cm and widths of about 0.95 cm. The arms are integrally attached to both ends of the central zone.

In one embodiment, the implant preferably includes a placement loop secured to the central region of the implant. In one embodiment, the placement loop is a sterile, single-patient use device consisting of a monofilament loop of PROLENE™ suture with an attached polypropylene button. The loop and the button are pre-assembled as part of the implant at the center of the mesh to aid in the placement of the central zone of the mesh under the urethra.

In one embodiment, the implant is a surgical mesh, and one or more insertion tips are attached to the mesh, such as by using ultrasonic welding. In one embodiment, a proximal end of the insertion tip includes a hoop having a hoop opening that enables the mesh to be pulled therein, and that desirably entraps the mesh within the hoop. In one embodiment, the hoop is melted so that it conforms to the outer profile of the insertion tip. In one embodiment, the hoop preferably has one or more crush points to insure that the hoop arms fold inward and not outward during welding. In one embodiment, the hoop preferably has one or more internal ribs to ensure good bonding of the mesh to the insertion tip without damaging the hoop.

In one embodiment, the mesh may be secured to the one or more insertion tips using holes, glue, sewing, or insert welding. In other embodiment, the insertion tips may include flexible overlapping wings that form a hoop for aiding in mesh insertion. The insertion tips may also be attached to the mesh using other variants such as overmolding of the insertion tip to the mesh.

In one embodiment, when used with a surgical mesh, a function of the insertion tip is to aid in the insertion and positioning of the surgical mesh in a controlled manner. The insertion tip preferably provides a tapered point affixed to the end of a surgical mesh to aid with inserting the mesh into tissue. The tapered insertion tip desirably facilitates controlled implantation of the mesh by creating a tissue pathway without requiring the use of a scissor, blunt dissection, or knife dissection. The insertion tip can be pushed in or pulled out of the tissue, without being disconnected from the insertion device, for providing a surgeon with the ability to precisely position the mesh without causing unwanted tissue trauma. The insertion tip preferably holds the surgical mesh in a desired location until the insertion tip is intentionally unlocked from an insertion device.

In one embodiment, the insertion tip has a central lumen for securing the insertion tip to the distal end of an insertion device. In one embodiment, the distal end of the insertion device includes a latching assembly with elastic latches and the insertion tip has one or more fenestrations, windows, or recesses formed in the sides of the insertion tip that receive the elastic latches for locking the insertion tip to the latching assembly.

In one embodiment, the insertion tip is made of an absorbable material, such as PDS. In one embodiment, the absorbable insertion tip will degrade in the body over a period of about three-nine months. In one embodiment, the insertion tip is may be made of non-absorbable materials, such as polypropylene.

In one embodiment, the insertion tip has a diameter that is slightly greater than the diameter of the distal end of the shaft of the insertion device. In one embodiment, the insertion tip has a diameter of about 4 mm, and the distal end of the shaft of the insertion device has a diameter of about 3 mm.

In one embodiment, the insertion device has a curved distal section. In one embodiment, the distal end of the insertion device and the proximal end of the insertion tip are designed to be engaged in a predetermined orientation. In one embodiment, the insertion tip has a pointer or alignment indicator that aids in alignment of the insertion tip with respect to the insertion device.

In one embodiment, the insertion tip preferably has a tail used to contain the end of a mesh implant. The tail may assist in orienting the insertion tip relative to the insertion device. In one embodiment, the insertion device has a shaft with a curve near the distal end of the shaft that resists flexing of the shaft as the implant is placed. In one embodiment, the tail of the insertion tip is aligned with the outside curvature of the curved shaft of the insertion device.

In one embodiment, the insertion tip has a conical or semi-conical distal geometry and a barb-less structure. This design preferably enables the insertion tip, prior to being unlocked and released from the insertion device, to be moved in proximal and distal directions within tissue for positioning the insertion tip in the tissue with minimal tissue trauma.

In one embodiment, the insertion tip has barbs and/or hooks. In one embodiment, the barbs and/or hooks are shielded from the tissue by structures on the insertion device while engaged with the insertion device.

In one embodiment, the implant insertion system preferably includes two stainless steel, curved shaft inserters with plastic inserter handles incorporating release buttons or actuators that are designed to deliver the implant. The inserters are provided as left-hand and right-hand insertion device units for engaging the two insertion tips attached to the ends of the implant.

In one embodiment, the insertion device preferably includes an actuator, a push wire, a latching assembly and a tip pin whereby the actuator, push wire, and tip pin are not connected together. The absence of a permanent connection between the tip pin, the push wire, and the actuator requires the use of less force when locking the insertion tip onto the distal end of the insertion device.

In one embodiment, the push wire may be made from stainless steel, but may also be made of various materials such as nylon, Teflon, polypropylene or any combination thereof. In one embodiment, the push wire is not attached to either the actuator or the tip pin and is free to move in distal and proximal directions within the outer shaft of the insertion device. The push wire moves distally when urged to move distally by the actuator, and moves proximally when urged to move proximally by the tip pin. In one embodiment, from a start position, the actuator is advanced distally about 0.300", which, in turn, results in the push wire advancing distally about 0.060". Thus, there is some lost motion between the distal advancement of the actuator and the distal advancement of the push wire, and the ratio of distal travel between the actuator and the push wire is about 5:1. In one embodiment, the actuator has a ramp that moves distally and proximally with the actuator, and the handle half has a fixed flexible arm that travels over the ramp as the actuator moves distally and proximally. The engagement of the fixed flexible arm with the ramp creates a first detectable click when the actuator is advanced to its most distal position (correlating with unlocking the insertion tip from the latching assembly), and a second detectable click when the actuator is returned to its most proximal position for beginning another cycle.

In one embodiment, the tip pin is a wire that is used to move the elastic latches of the latching assembly both inwardly and outwardly. The tip pin has a wider diameter distal end that forces the latches outwardly, and a reduced diameter neck that is located proximal to the wider diameter distal end that enables the latches to flex inwardly. The tip pin is free to slide in proximal and distal directions relative to the latching assembly. The tip pin is not attached with the push wire, which allows the tip pin to have very detailed machining and grinding, and which requires less force for locking the insertion tip onto the distal end of the insertion device.

The latching assembly is preferably a one piece design that includes a main body with elastic, flexible latches spaced from one another at the distal end of the latching assembly. The inner surfaces of the latches and the outer surface of the tip pin are designed with opposing cam surfaces for selectively locking and unlocking the insertion tip from the insertion device. When expanded by the tip pin, the latches lock securely into the fenestrations of the insertion tip for locking the insertion tip to the latching assembly and adding stiffness to the assembly of the insertion device and the insertion tip, which is important when the insertion tip and the latching assembly are made from soft materials such as absorbable PDS and polycarbonate, respectively.

In one embodiment, the latching assembly may be made of metal and may include an elongated metal body, elongated metal latches disposed in slots formed in the elongated metal body, the latches having opposing inner cam surfaces and respective latch posts that extend away from one another, and an elongated rod moveable in proximal and distal directions that is positioned between the inner cam surfaces of the opposing metal latches. The elongated rod has an outer surface with a protrusion that is adapted to ride over the opposing inner cam surfaces of the latches. In one embodiment, when an insertion tip is positioned over a distal end of the elongated rod and moved proximally, the protrusion on the outer surface of the elongated rod moves proximally for contacting the inner cam surfaces for moving the latch posts away from one another. As the latch posts move away from one another, the latch posts advance into windows formed on an insertion tip for locking the insertion tip to the latching assembly. When the elongated rod is moved distally for unlocking the insertion tip from the latching assembly, the opposing inner cam surfaces align with a smaller diameter section of the elongated rod so that the latch posts are able to move inwardly toward one another for being retracted from the windows of the insertion tip. As the elongated rod moves distally, the distal end of the elongated rod engages the closed end of the central lumen of the insertion tip for separating the distal end of the latching assembly from the insertion tip, while the insertion tip remains in place in tissue.

In one embodiment, the latching assembly design is unique because two relatively small plastic parts (i.e. polycab for the latches and PDS for the insertion tip) enable the two parts to be strong enough to withstand the forces of insertion and removal. This system differs from other stress urinary incontinence devices that require a metal tip to facilitate placement in tissue.

In one embodiment, an insertion tip has a central lumen and one section of a wall of the central lumen extends proximally beyond the length of the central lumen. When the insertion tip is secured to the insertion device, one section of the elongated wall that extends proximally from the central lumen is preferably oriented on the outer curvature of the distal curved section of outer shaft of the insertion device. This orientation desirably maintains the centrality of the insertion tip relative to the insertion device and ensures proper alignment of the insertion tip on the distal end of the insertion device so that a section of the elongated wall of the insertion tip aids in resisting flexing of the insertion tip as it is placed into tissue.

In one embodiment, the distal end of the insertion device is designed to mate with the insertion tip such that the insertion tip can only be mounted to the insertion device in a single orientation. This design allows for two plastic parts (i.e., the plastic latching assembly and the plastic insertion tip) to cooperatively resist bending that to date has only been achieved when using insertion tips made of metal.

In one embodiment, moving the insertion tip in a proximal direction over the distal end of the insertion device causes proximal movement of a tip pin, which, in turn, causes outward radial deployment of one or more latches of the latching assembly. The outwardly moving latches advance into fenestrations, windows or recesses formed in the insertion tip for securing the insertion tip to the latching assembly at the distal end of the insertion device. In one embodiment, the proximal motion of the insertion tip to engage the tip pin on the insertion device is between about 0.02-0.06", and more preferably about 0.040".

In one embodiment, unlocking the insertion tip from the distal end of the insertion device preferably includes moving a tip pin in a distal direction for allowing inward radial movement of the elastic latches, which enables retraction of the latches from the fenestrations, windows or recesses for unlocking the insertion tip from the latching assembly of the insertion device, which, in turn, positively moves the insertion device to a new location relative to the insertion tip for unlocking the insertion tip from the insertion device.

The radially extendable and retractable latches enable an insertion tip to be securely held by an insertion device via a single motion. As a result, the insertion tip may be used to dissect tissue and/or be positioned within tissue without concern that the insertion tip will prematurely separate or detach from the insertion device until desired by the surgeon. The fenestrations, windows or recesses within the insertion tip preferably allow for positive locking and unlocking from the inserter, encourage tissue in-growth, and minimize the likelihood of infection.

In one embodiment, the insertion device includes a tip pin having a outer surface that interacts with the inner cam surfaces of the elastic latches of a latching assembly. In one embodiment, the push wire is made of metal or polymer materials, or a combination of both. In one embodiment, the tip pin is moved distally by a sliding push wire that is not connected to either the tip pin or the actuator. When the tip pin moves proximally, a larger diameter section of the tip pin engages the inner cam surfaces of the elastic latches for urging the latches to move in an outward radial direction for locking the insertion tip to the insertion device. When the tip pin is advanced distally, a reduced diameter neck section of the tip pin engages the inner cam surfaces of the elastic latches to enable the latches to flex in an inward radial direction for unlocking the insertion tip from the distal end of the insertion device.

In one embodiment, the fenestrations, windows or recesses have respective lengths that are greater than the length of the latch posts on the latches. The greater lengths of the fenestrations, windows or recesses provides sufficient clearance to allow proximal movement of the latch posts within the insertion tip to ensure that the insertion tip does not move distally during unlocking and release of the insertion tip from the insertion device.

In one embodiment, the actuator is used to unlock the insertion tip from the insertion device. In one embodiment, the actuator on the handle is pushed distally for urging the push wire to move distally. In turn, the distally moving push wire pushes the tip pin in a distal direction. As the tip pin is urged to move distally by the push wire, the reduced diameter neck of the tip pin moves into alignment with the inner cam surfaces of the elastic latches for allowing the latches to flex inwardly, which, in turn, enables the latches of the latching assembly to retract from the fenestrations on the sides of the insertion tip. In one embodiment, the tolerances and the cam angles are very precise to ensure locking and unlocking of the insertion tip within a very short distance of linear movement of the tip pin of about 0.010-0.020".

In one embodiment, the actuator has an internal mechanism, such as a ramp, attached thereto that interacts with a fixed flexible element inside the handle to provide a detectable click and/or tactile feedback when the actuator is pushed to a distal-most position for signaling that the insertion tip has been unlocked from the insertion device. In one embodiment, the fixed flexible element rides over the ramp as the actuator is moved distally and proximally. In one embodiment, the fixed flexible element and the ramp generate a first detectable click when the actuator is advanced to a distal-most position which corresponds with unlocking of the insertion tip, and a second detectable click when the actuator is returned to a proximal-most position. Thus, the insertion device generates a detectable double click during a complete cycle of movement of the actuator.

In one embodiment, a return spring is connected with the actuator for returning the actuator to an initial start position after the actuator has been pushed distally. The return spring enables multiple firing of the insertion device in the event of reloading or test firing prior to final use.

In one embodiment, a shield is provided at the distal end of the insertion device to protect and/or isolate the insertion tip from tissue until the insertion device has reached a desired location. In one embodiment, when the insertion tip and shield reach the desired location, the shield may be retracted and or removed to expose the insertion tip for enabling the insertion tip to be advanced into tissue. The shield preferably acts as a tissue stop to prevent unintended damage and/or injury to surrounding organs, tissue, or body structures.

In one embodiment, the implant insertion system includes an atraumatic winged guide, which is a stainless steel accessory instrument that facilitates consistent passage of the implant through the dissection tract. The winged guide is marked with an insertion zone to aid the surgeon's assessment of the inserted depth. The insertion zone indicates a distance of 3-4 cm from the tip of the winged guide.

In one embodiment, an alternate method of fixedly attaching an insertion tip to an insertion device uses a 'snap-tip' arrangement. In this embodiment, the central lumen of the insertion tip is elastically deformed by a protrusion (i.e., a raised portion) provided on the outer surface of the insertion device as the insertion device moves in a distal direction within the central lumen of the insertion tip. The elastic deformation of the central lumen returns to its original shape when the protrusion on the insertion device reaches a recess, widened section, or window located toward the distal end of the central lumen of the insertion tip. Alternatively, the protrusion may reside on the inside of the central lumen of the insertion tip and the corresponding recess may reside on an outer surface of a distal end of an insertion device.

In one embodiment, the snap-tip arrangement has no moving parts. The snap tip may be made of plastic, metal or other suitable materials. The snap-tip protrusions insertable into fenestrations have a profile size of about 0.002-0.030" and more preferably in the range of about 0.010"-0.020". The protrusions on the snap tip may be at full width to fill the fenestrations in the insertion tip or smaller depending on the holding force that is required. The protrusions may also include a radius at the distal end. In one embodiment, the shape of the protrusions on the snap-tip may be formed using a grinding machine to form a detent lock having unlocking forces that can be altered by changes to angles and/or diameters of the snap-tip body or the snap-tip protrusions.

These and other preferred embodiments of the present invention will be described in more detail below.

BRIEF DESCRIPTION OF THE DRAWING

FIG. 7A shows a cross-sectional view of a push wire, a latching assembly, a tip pin, and an insertion tip, in accordance with one embodiment of the present invention.

FIG. 7B shows a magnified view of the latching assembly, tip pin, and insertion tip shown in FIG. 7A.

FIGS. 14A-14C show a cross-sectional view of a method of securing and self-locking an insertion tip to a latching assembly at a distal end of an insertion device, in accordance with one embodiment of the present invention.

DETAILED DESCRIPTION

Figure 1A:
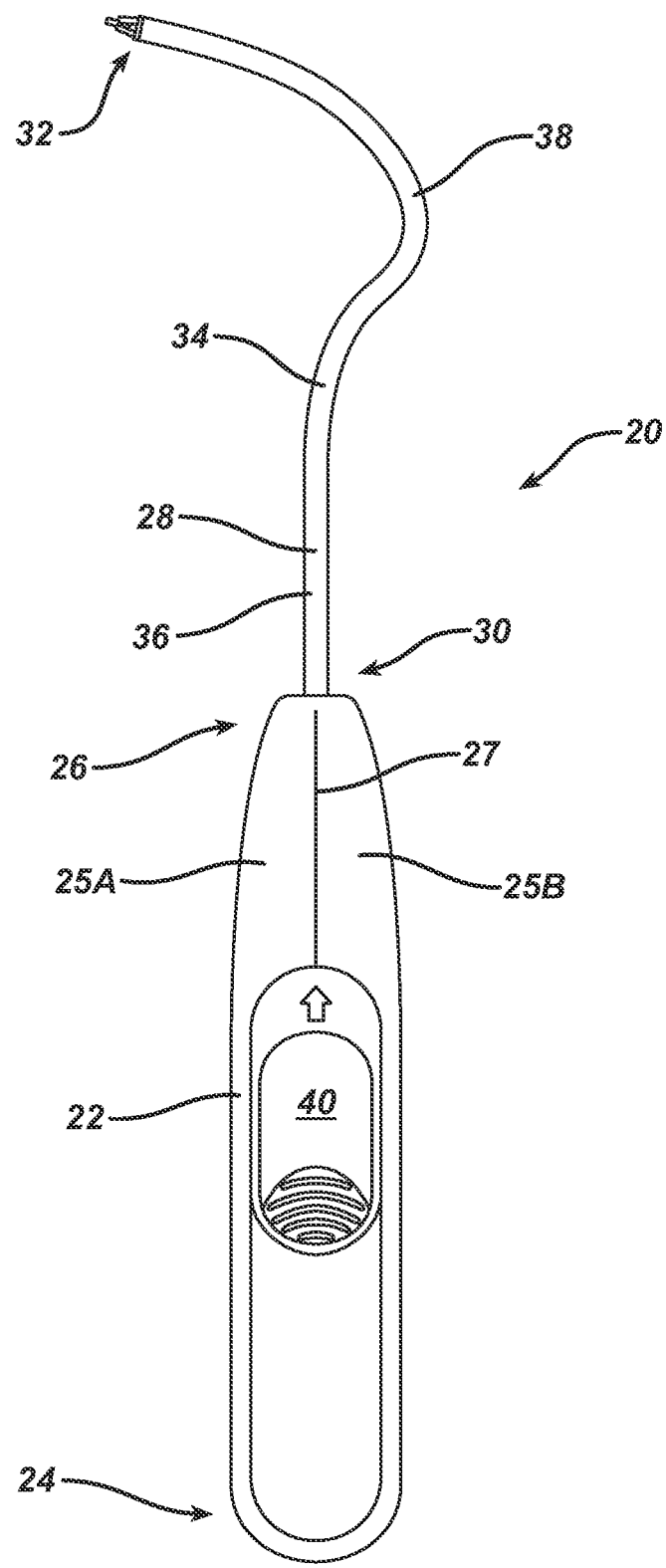
FIG. 1A shows a top plan view of an insertion device of an implant insertion system, in accordance with one embodiment of the present invention.

Referring to FIG. 1A, in one embodiment, an implant insertion system preferably includes an insertion device 20, having a handle 22 with a proximal end 24 and a distal end 26. The insertion device 20 includes an outer shaft 28 having a proximal end 30 secured to the handle 22 and a distal end 32 remote therefrom. The distal end 32 of the outer shaft 28 is a free end of the outer shaft and is adapted for connection with an insertion tip of an implant insertion tip, as will be described in more detail herein. The outer shaft 28 preferably includes a midsection 34 located between the proximal end 30 and the distal end 32 thereof. The outer shaft 28 has a first section 36 extending between the proximal end 30 and the midsection 34 that is substantially straight, and a second section 38 extending between the midsection 34 and the distal end 32 that is curved. In one embodiment, the distal-most end 32 of the outer shaft 28 is preferably straight. The insertion device 20 includes an actuator 40 that is slideable toward the distal end 26 of the handle 22 for selectively unlocking and/or releasing an insertion tip secured to the distal end 32 of the outer shaft 28.

In one embodiment, the distal end 26 of the handle 22 preferably includes first and second flat surfaces 25A, 25B that are separated by a dividing line 27. The first and second flat surfaces 25A, 25B are adapted for being engaged by a surgeon's thumb for enabling the surgeon to have more leverage and control over the insertion device 20 during a surgical procedure.

Referring to FIG. 1B, in one embodiment, the implant insertion system preferably includes a left-hand insertion device 20A, which is similar to the insertion device 20 shown in FIG. 1A, and a right-hand insertion device 20B. The left-hand insertion device 20A and the right-hand insertion device 20B are preferably mirror images of one another. The second section 38A of the outer shaft 28A of the left-hand insertion device 20A curves to the left and the second section 38B of the outer shaft 28B of the right-hand insertion device 20B curves to the right. The left-hand and right-hand insertion devices 20A, 20B preferably operate in a similar manner with one difference being that the outer shaft 28A on the left-hand device 20A curves to the left and the outer shaft 28B on the right-hand device 20B curves to the right. In one embodiment, the outer shaft 28A of the left-hand insertion device 20A preferably curves to the left from the perspective of a surgeon, which is toward the right-hand side of a patient, and the outer shaft 28B of the right-hand insertion device 20B preferably curves to the right from the perspective of the surgeon, which is toward the left-hand side of the patient.

Figure 2A:
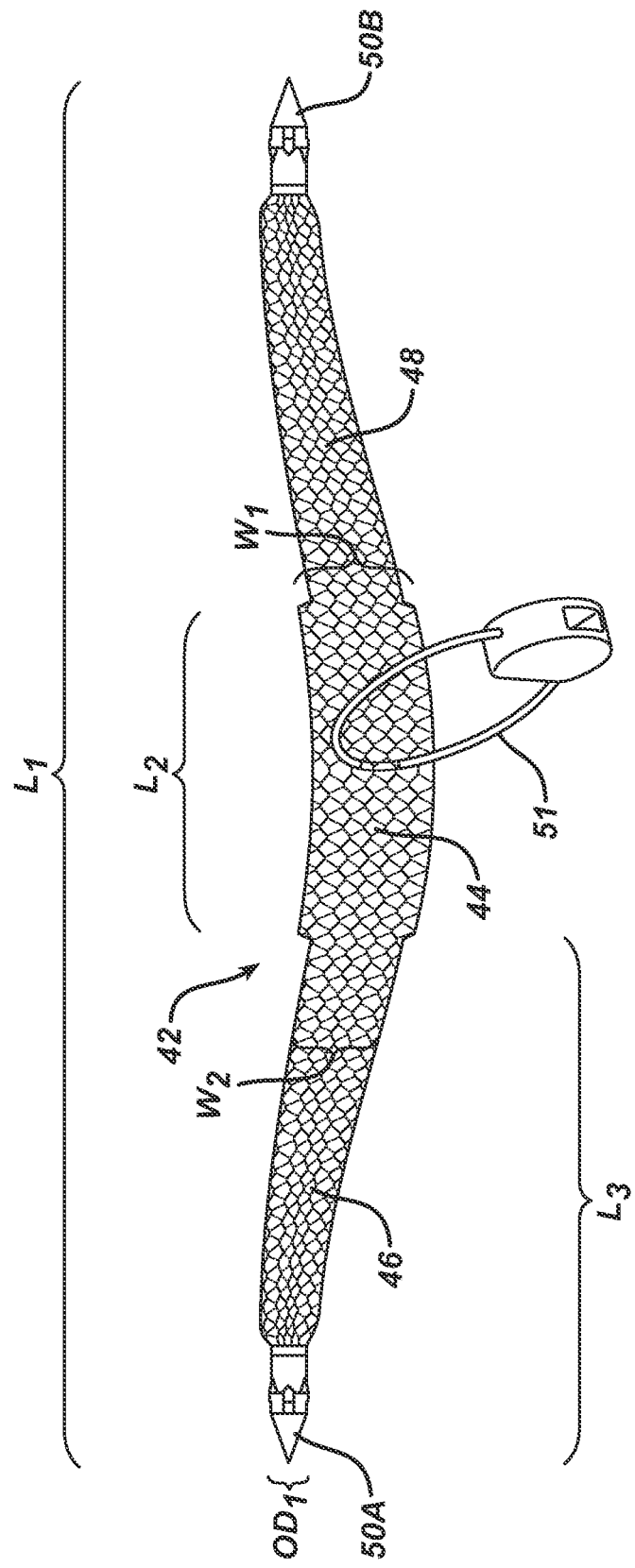
FIG. 2A shows a top plan view of an implant having a central region, first and second arms, first and second insertion tips secured to the respective first and second arms, and a pull loop, in accordance with one embodiment of the present invention.

Referring to FIG. 2A, in one embodiment, the left and right-hand insertion devices 20A, 20B shown in FIG. 1B may be utilized for securing an implant 42 to tissue. The implant 42 may be made of a mesh material. In one embodiment, the implant 42 has a length $L_1$ of about 8-20 cm, and more preferably about 12 cm. The implant 42 has a central region 44 having a length $L_2$ of about 2-4 cm and more preferably about 3 cm, and a width $W_1$ of about 0.8-1.5 cm and more preferably about 1.1 cm. The implant 42 includes first and second arms 46, 48 that are integrally formed with and extend from opposite ends of the central region 44. The first and second arms have a length $L_3$ of about 3-5 cm and more preferably about 4.5 cm, and a width $W_2$ of about 0.5-1.2 cm and more preferably about 0.95 cm. The implant 42 desirably includes a first insertion tip 50A that is attached to the outer end of the first arm 46 of the implant 42, and a second insertion tip 50B that is attached to the outer end of the second arm 48 of the implant 42. The insertion tips 50A, 50B are preferably used for advancing the implant 42 through tissue and for securing the implant at a desired location within the tissue.

In one embodiment, the insertion tips 50A, 50B have an outer diameter $OD_1$ of about 3-5 mm, and more preferably about 4 mm. In one embodiment, the width $W_2$ of the first and second arms 46, 48 of the implant 42 is less than the width $W_1$ of the central region 44 of the implant so that the first and second arms 46, 48 are less resistant to lengthening than is the central region 44. The reduced resistance to lengthening preferably reduces the footprint of the arms as they are advanced through a surgical opening and into tissue. Although the present invention is not limited to any particular theory of operation, it is believed that the smaller relative width of the first and second arms 46, 48, which enables more stretching of the arms than the central section when under tension, which provides an implant 42 having auto-tensioning capabilities.

In one embodiment, the mesh material is preferably made of polypropylene, or a combination of polypropylene and MONOCRYL absorbable material. In one embodiment, the implant preferably includes a mesh, such as a shaped piece of blue (phthalocyanine blue, color index number 74160) PROLENE™ polypropylene mesh. The implant is attached to two insertion tips such as violet (D&C violet no. 2, color index number 60725) PDS™ (Polydioxanone) absorbable insertion tips. The absorbable insertion tips are preferably molded from polydioxanone identical in composition to that used in PDS™ II (polydioxanone) suture.

In one embodiment, the mesh is preferably constructed of knitted monofilaments of extruded non-absorbable polypropylene strands identical in composition to polypropylene suture sold under the trademark PROLENE™. The PROLENE™ mesh is knitted using a process that interlinks each fiber junction and provides elasticity that allows adaptation to various stresses encountered in the body.

In one embodiment, the implant 42 is a sterile device that is intended to be used one time on a single patient. In one embodiment, the implant preferably includes a placement loop 51 with a button secured to the central region 44 of the implant. In one embodiment, the placement loop has a monofilament loop of PROLENE™ suture with an attached polypropylene button. The loop and the button are pre-assembled as part of the implant at the center of the mesh to aid in the placement of the central region 44 of the mesh under an urethra.

Referring to FIG. 2B, in one embodiment, the left-hand insertion device 20A has an outer shaft 28A with a curved section 38A that curves to the left, which is adapted for securing the first insertion tip 50A to a latching assembly at the distal end of the outer shaft 28A. The right-hand insertion device 20B includes an outer shaft 28B having a curved section 38B that curves to the right, which is adapted for securing the second insertion tip 50B to a latching assembly at the distal end of the outer shaft 28B.

In one embodiment, the first insertion tip 50A is secured to the distal end 32A of the outer shaft 28A of the left-hand insertion device, and the distal end of the left-hand insertion device 20A is utilized for positioning the first arm 46 of the implant 42 within a patient at a first location. The second insertion tip 50B is secured to the distal end 32B of the outer shaft 28B of the right-hand insertion device 20B, and the right-hand insertion device 20B is utilized for positioning the second arm 48 of the implant 42 within a patient at a second location. The left and right-hand insertion devices 20A, 20B may be utilized for adjusting the spacing between the first insertion tip 50A and the second insertion tip 50B until the implant 42, including the central region 44 of the implant, has been positioned at a desired location.

When the insertion tips 50A, 50B and the implant 42 have been properly positioned within a patient, the actuators 40A, 40B on the respective left and right-hand insertion devices 20A, 20B are utilized for unlocking the first and second insertion tips 50A, 50B from the latching assemblies at the distal ends of the respective left and right-hand insertion devices 20A, 20B. As will be described in greater detail herein, once the insertion tips have been positioned at desired locations, the first and second insertion tips 50A, 50B are desirably unlocked and released from the distal ends of the respective left and right-hand insertion devices without moving the first and second insertion tips from their respective desired locations.

Figure 3A:
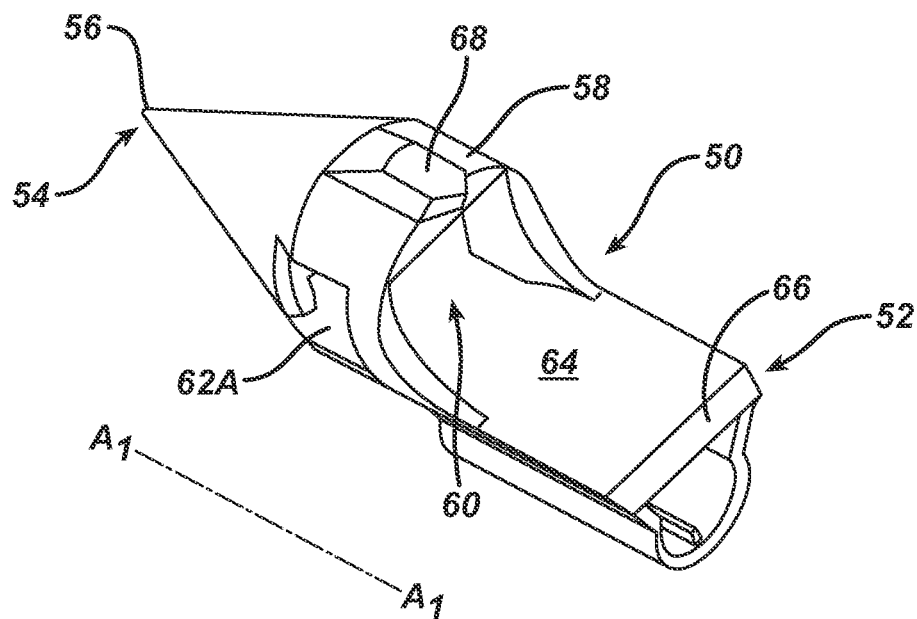
FIG. 3A shows a perspective view of an insertion tip for an implant, in accordance with one embodiment of the present invention.
Figure 3B:
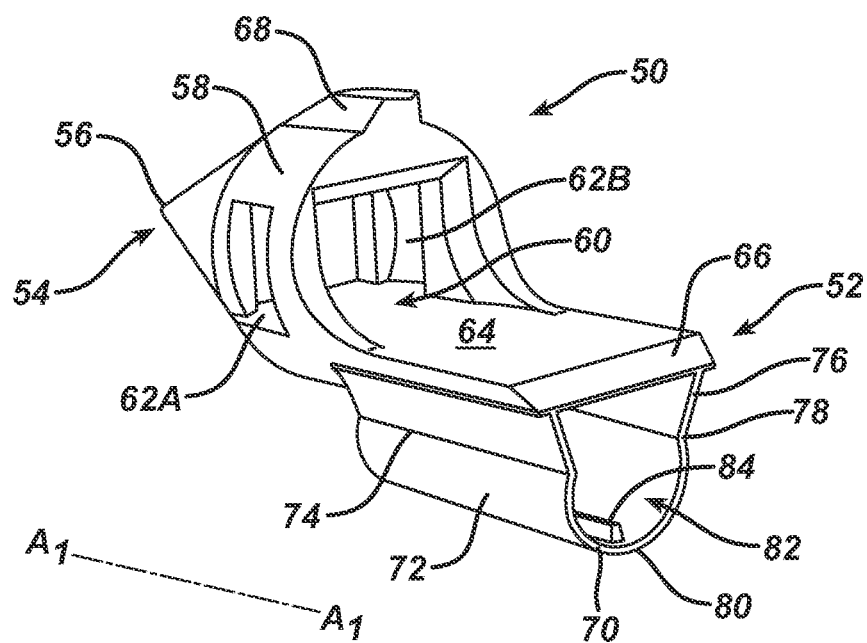
FIG. 3B shows another perspective view of the insertion tip shown in FIG. 3A.
Figure 3C:
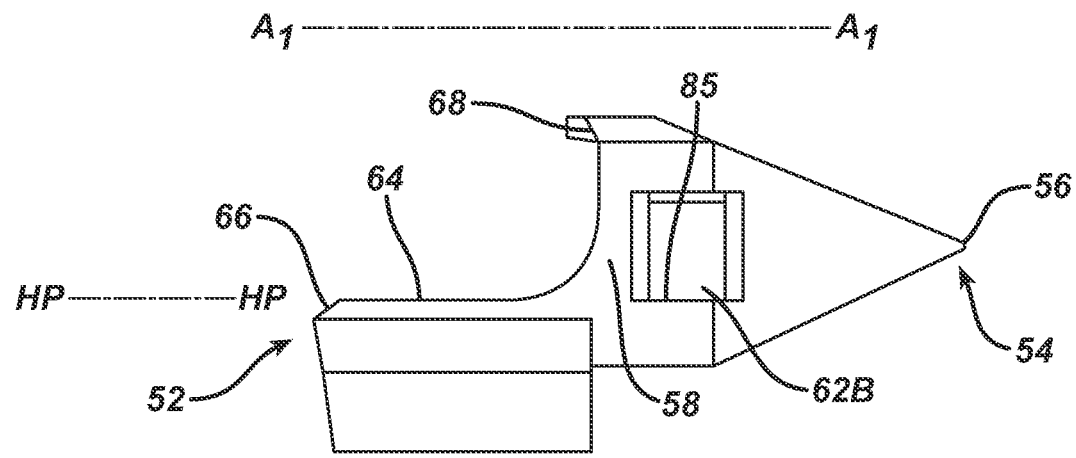
FIG. 3C shows a side elevation view of the insertion tip shown in FIGS. 3A and 3B.

Referring to FIGS. 3A-3C, in one embodiment, an insertion tip 50 for an implant preferably includes a proximal end 52 and a distal end 54 having a tapered point 56. The insertion tip 50 includes a base 58 that extends proximally from the tapered point 56. The insertion tip 50 has a central lumen 60 that is surrounded by the base 58. The central lumen 60 desirably has a distal end that is closed and a proximal end that is open for receiving the latching assembly at the distal end of an insertion device (FIG. 2B). A pair of opposing fenestrations or windows 62A, 62B are formed in the sides of the base 58 and provide radial access into the central lumen 60.

The insertion tip 50 preferably includes an elongated flat surface 64 that extends proximally from the central lumen 60 toward the proximal end 52 of the insertion tip 50. The elongated flat surface 64 has a distal end that is co-planar with a bottom wall or floor of the central lumen 60. The bottom wall or floor of the central lumen 60 intersects with lower ends of the opposing windows 62A, 62B.

The insertion tip 50 desirably includes a sloping surface 66 at the proximal end 66 of the insertion tip 50 that slopes in a downward and proximal direction between the elongated flat surface 64 and the proximal end 52 of the insertion tip 50. The sloping surface 66 preferably engages an opposing sloping surface provided at a distal end of an outer shaft of an insertion device as will be described in more detail herein.

The insertion tip 50 desirably extends along a longitudinal axis $A_1$. In one embodiment, the insertion tip 50 includes an alignment post 68 that also extends along the longitudinal axis $A_1$. The alignment post 68 preferably enables surgical personnel to properly orient the insertion tip 50 relative to the distal end of an insertion device. The alignment post 68 may also enable surgical personnel to properly orient the insertion tip 50 within a patient's body.

Figure 3D:
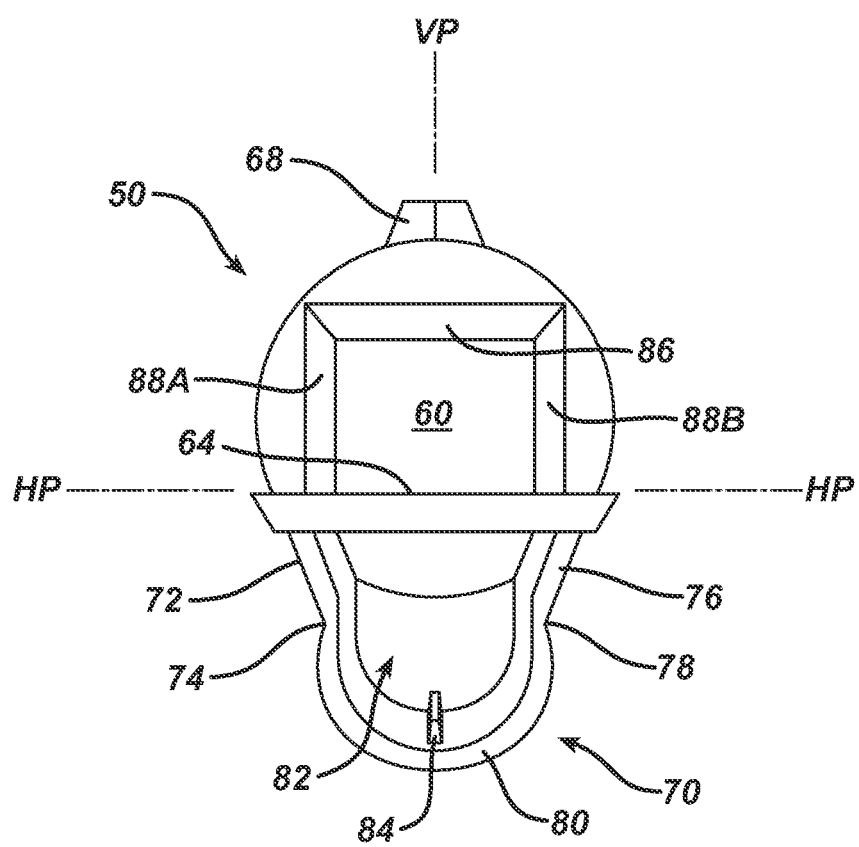
FIG. 3D shows a rear elevation view of the insertion tip shown in FIGS. 3A-3C.

Referring to FIGS. 3B and 3D, the insertion tip 50 preferably includes a hoop 70 adapted to capture an end of the implant 42 (FIG. 2A). The hoop 70 preferably includes a first side wall 72 having a first crush point 74 and a second side wall 76 having a second crush point 78. The hoop 70 desirably includes a base 80 that spans the gap between the first side wall 72 and the second side wall 76. The first and second side walls 72, 76 and the base 80 desirably define a hoop opening 82 adapted to receive an end of an implant. In one embodiment, the base 80 desirably has an internal rib 84 that extends along the longitudinal axis $A_1$ of the insertion tip 50. The rib 84 may extend only partially along the length of the hoop 70. The rib 84 desirably provides frictional engagement with the implant when the hoop 70 is collapsed onto the end of the implant inserted into the hoop opening 82.

In one embodiment, an end of an implant, such as the end of a mesh implant, is pulled into the hoop opening 82 via a hook placed through the distal end of the hoop opening. In one embodiment, the hoop is crushed down and the crush points 74, 78 in the first and second side walls 72, 76 are pushed inwardly toward one another for collapsing the hoop opening 82 so that the end of the implant is pinched between the first and second side walls 72, 76 and the hoop base 80. The internal rib 84 desirably forms a frictional engagement with the implant material inserted into the hoop opening for holding the implant material within the hoop opening 82. The hoop is preferably melted to the bottom of the elongated flat surface to capture the end of the mesh within the collapsed hoop.

Referring FIGS. 3C and 3D, in one embodiment, the central lumen 60 of the insertion tip 50 is defined a bottom wall 85, a top wall 86 that opposes the bottom wall 85, and internal, opposing side walls 88A, 88B. The elongated flat surface 64 is co-planar with and extends proximally from the bottom wall 85. In one embodiment, the bottom wall 85, the top wall 86 and the internal, opposing side walls 88A, 88B define a parallelogram, such as a square or rectangular shaped opening. The distal-most end of the insertion device 20 (FIG. 1) preferably includes a latching assembly having a square or rectangular shaped tip that matches the square or rectangular shaped opening of the central lumen 60.

Referring to FIGS. 3C and 3D, in one embodiment, the insertion tip 50 extends along the longitudinal axis $A_1$. The elongated flat surface 64 lies within a horizontal plane HP, and the alignment post 68 and the internal rib 84 lie within a vertical plane VP. The horizontal plane HP is desirably perpendicular to the vertical plane VP.

Figure 4:
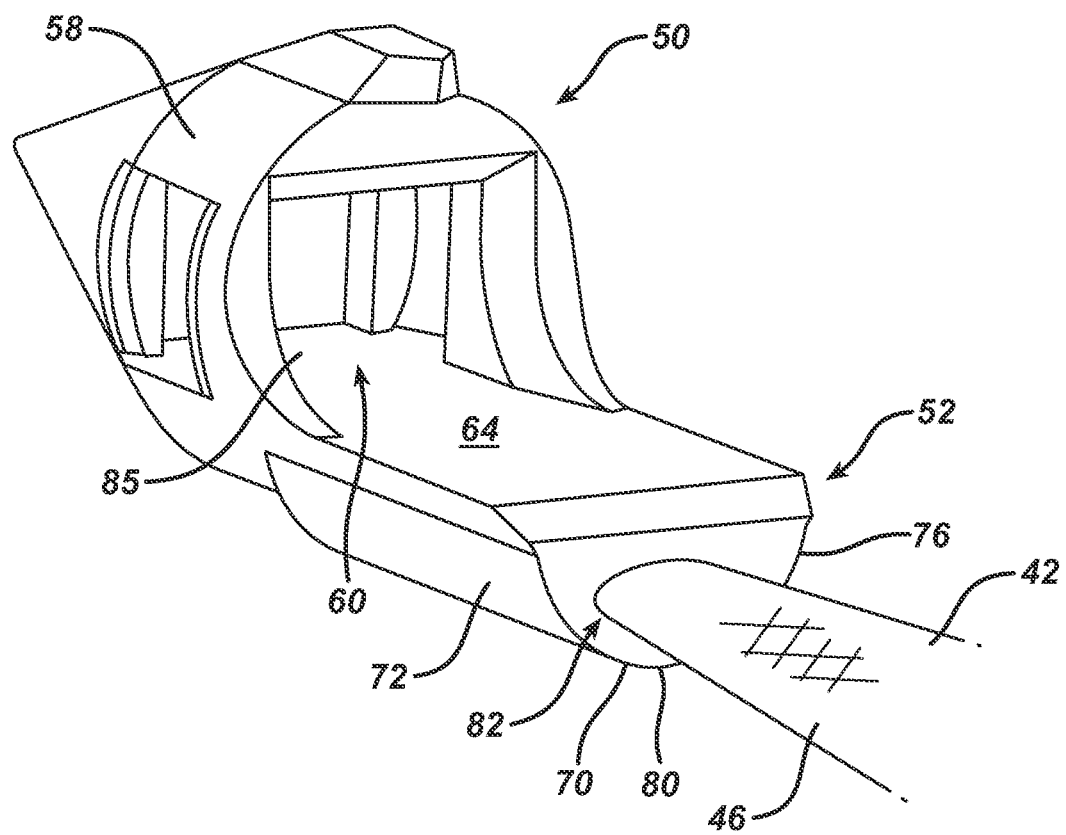
FIG. 4 shows a perspective view of the first end of the implant of FIG. 2A after mesh attachment, in accordance with one embodiment of the present invention.

Referring to FIGS. 2A, 3D and 4, in one embodiment, a free end of the first arm 46 of the implant 42 is attached to the hoop opening 82 at the proximal end 52 of the first insertion tip 50A. In one embodiment, the hoop is collapsed and the first and second side walls 72, 76 of the hoop 70 are collapsed inwardly for pinching the free end of the first arm 46 of the implant 42 between the first and second side walls 72, 76 and the hoop base 80 for attaching the first arm 46 of the implant 42 to the proximal end 52 of the first insertion tip 50A. In one embodiment, the free end of the second arm 48 (FIG. 2A) of the implant 42 is attached to the second insertion tip 50B using the same methodology described above for the first insertion tip 50A.

Figure 5A:
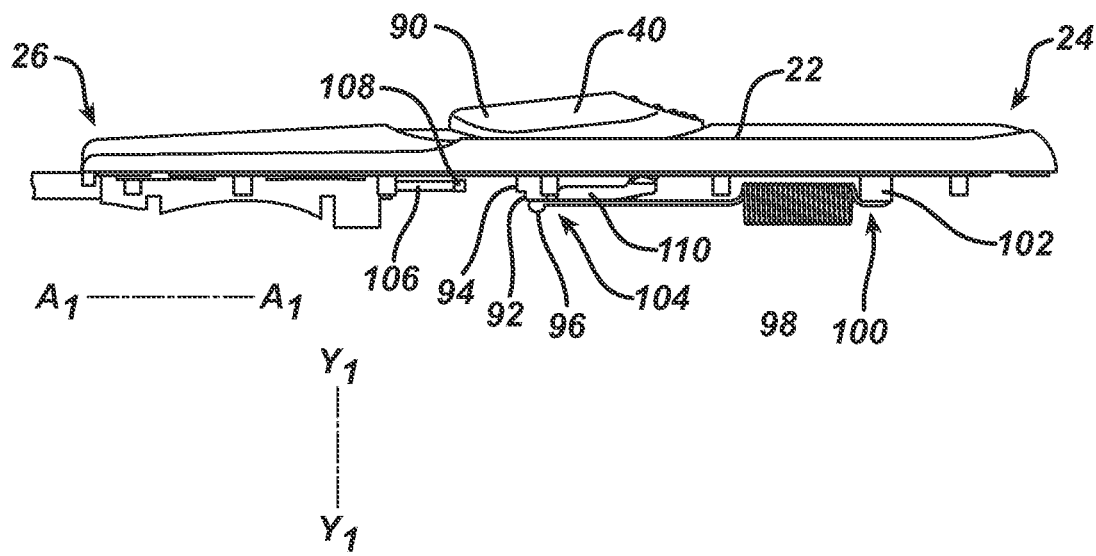
FIG. 5A shows a front elevation view of an upper half of a handle of the insertion device of FIG. 1A, in accordance with one embodiment of the present invention.

Referring to FIG. 5A, in one embodiment, the handle 22 of the insertion device 20 (FIG. 1A) preferably includes the proximal end 24 and the distal end 26. In FIG. 5A, the lower half of the handle 22 has been removed for providing a clear view of the internal components of the handle. The handle 22 includes the actuator 40 mounted thereon, which is adapted to slide between the proximal end 24 and distal end 26 of the handle 22. The actuator 40 desirably includes an external part 90 that is engageable outside the handle 22 (e.g. with a thumb) and an internal part 92 that is located inside the handle 22. The external part 90 and the internal part 92 move together along the longitudinal axis designated $A_1$. The internal part 92 includes a leading face 94 that extends along an axis $Y_1$ that is perpendicular to the longitudinal axis $A_1$ of the insertion device 20. The internal part 92 also includes a ramp (not shown) and an attachment post 96 that extends below the leading face 94.

The insertion device also preferably includes an actuator return spring 98 having a proximal end 100 connected to a post 102 provided inside the upper half of the handle 22. The actuator return spring 98 desirably includes a distal end 104 that is secured to the attachment post 96 provided on the internal element 92 of the actuator 40.

In one embodiment, a surgeon may engage the external part 90 of the actuator 40 for pushing the actuator 40 toward the distal end 26 of the handle 22 for unlocking an insertion tip from the latching assembly at the distal end of the insertion device. As the actuator 40 moves toward the distal end 26 of the handle, the actuator return spring 98 is stretched. When the actuator 40 is released, the stretched spring 98, having potential energy stored therein, returns the actuator 40 to the initial position shown in FIG. 1A.

Figure 5B:
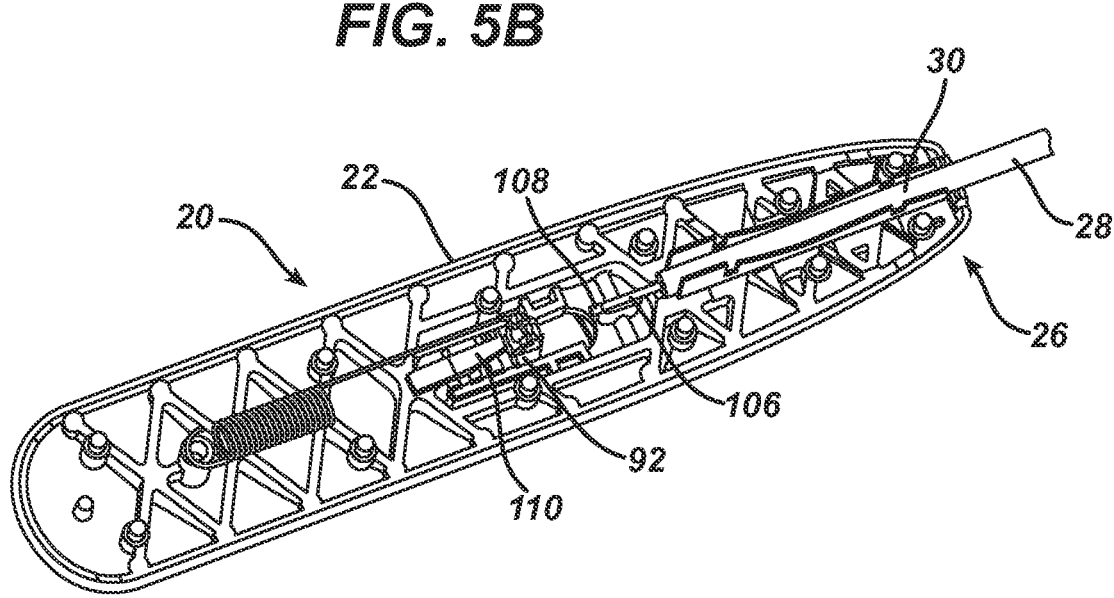
FIG. 5B shows a perspective view of the bottom surface of the upper half of the handle shown in FIG. 5A, in accordance with one embodiment of the present invention.

Referring to FIGS. 5A and 5B, in one embodiment, the proximal end 30 of the outer shaft 28 is secured with the distal end 26 of the handle 22. The outer shaft 28 preferably includes a central conduit (not shown) that extends between the proximal end 30 of the outer shaft 28 and the distal end 32 (FIG. 1A) of the outer shaft. The insertion device 20 preferably includes a push wire 106 that is disposed within the central lumen of the outer shaft 28. The push wire 106 preferably includes a proximal end 108 that is accessible inside the handle 22 for being contacted by the leading face 94 and a distal end that is located adjacent the distal end of the outer shaft 28. The push wire 106 moves freely in proximal and distal directions within the central lumen of the outer shaft 28.

Referring to FIGS. 5A and 5B, in one embodiment, the proximal end 108 of the push wire 106 is aligned with the leading face 94 of the internal part 92 of the actuator 40. The push wire 106 extends through the outer shaft toward the distal end of the outer shaft 28. The actuator return spring has a proximal end 100 secured to the post 102, and a distal end 104 secured to an anchor post 96 connected with the actuator 40. As the actuator 40 moves distally, the actuator return spring 98 is stretched for storing potential energy therein.

In one embodiment, the actuator 40 is pushed toward the distal end 26 of the handle 28, which simultaneously slides the leading face 94 of the internal actuator part 92 toward the distal end 26 of the handle 22. In one embodiment, as the actuator 40 moves distally and after lost motion, the leading face 94 of the internal actuator part 92 ultimately abuts against the distal end 108 of the push wire 106 for urging the push wire 106 toward the distal end of the outer shaft 28. In one embodiment, the ratio of distal movement of the actuator 40 to the push wire 106 is 5:1, which is due to the lost motion between the movement of the actuator and the movement of the push wire. A surgeon may confirm that the actuator 40 and the leading face 94 have been fully advanced toward the distal end 26 of the handle 22 upon hearing a detectable click or receiving tactile feedback generated by the ramp on the internal actuator part 92 engaging a flexible element 110 located inside the handle 22. After the actuator 40 has been fully advanced in the distal direction for unlocking the insertion tip, surgical personnel may release the external part 90 of the actuator, whereupon the return spring 98 pulls the actuator 40 back toward the initial start position (shown in FIG. 5A) for resetting the arm of the flexible element 110 on the ramp of the internal actuator part 92.

Figure 5C:
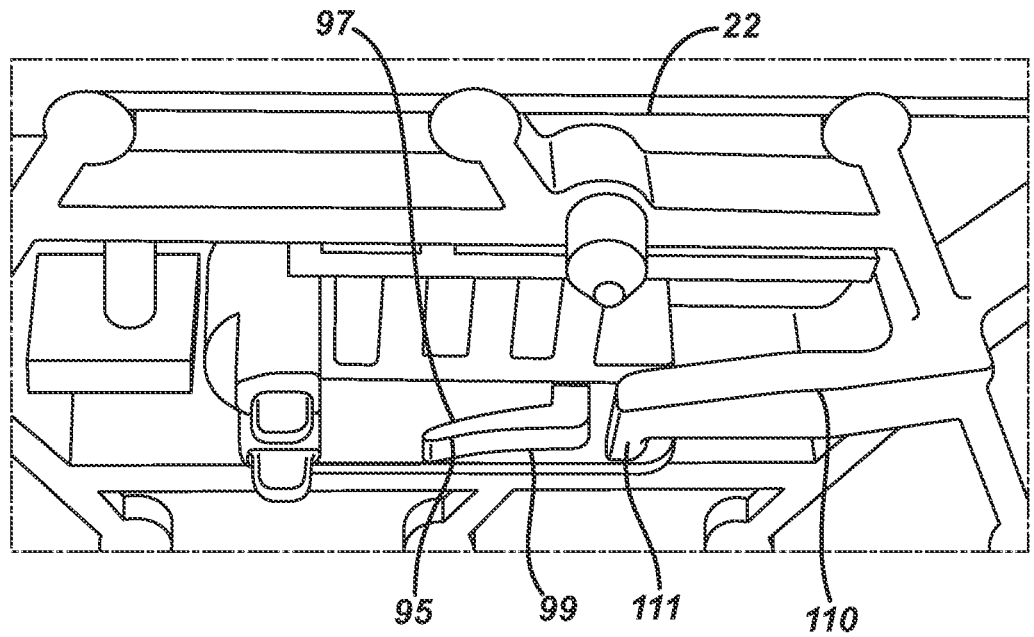
FIG. 5C shows a perspective view of an internal part of an actuator including a ramp and a flexible element having a free end that engages the ramp, in accordance with one embodiment of the present invention.

Referring to FIG. 5C, in one embodiment, as the actuator moves distally and proximally, the flexible element 110 has a free end 111 that slides over and under the ramp 95 of the internal actuator part 92 for generating a first detectable click when the actuator 40 is in a distal-most position and a second detectable click when the actuator 40 is in a proximal-most position. The ramp 95 preferably includes a top surface 97 and a bottom surface 99 that define a racetrack pattern, whereby the free end 111 of the flexible element 110 travels around the racetrack pattern as the actuator moves distally and proximally. In one embodiment, the top and bottom surfaces 97, 99 of the ramp 95 slope upwardly toward the distal end of the handle 22. In one embodiment, the flexible element 110 is flexed up as the free end 111 slides over the top surface 97 of the ramp 95, and the flexible element 110 is flexed down as the free end 111 slides over the bottom surface 99 of the ramp 95.

Figure 6A:
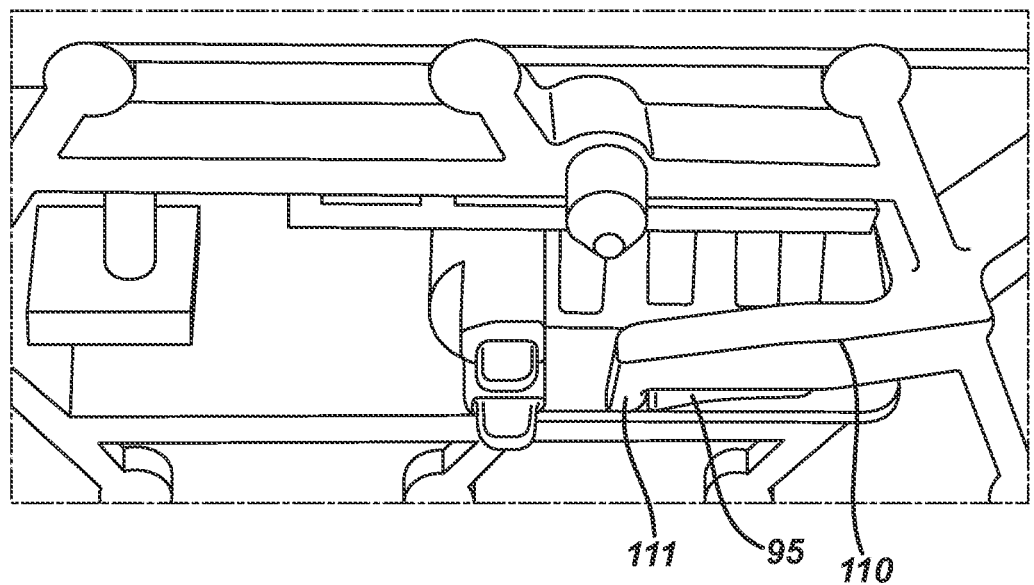
FIGS. 6A-6C show a method of using an insertion device for generating a detectable click, in accordance with one embodiment of the present invention.
Figure 6B:
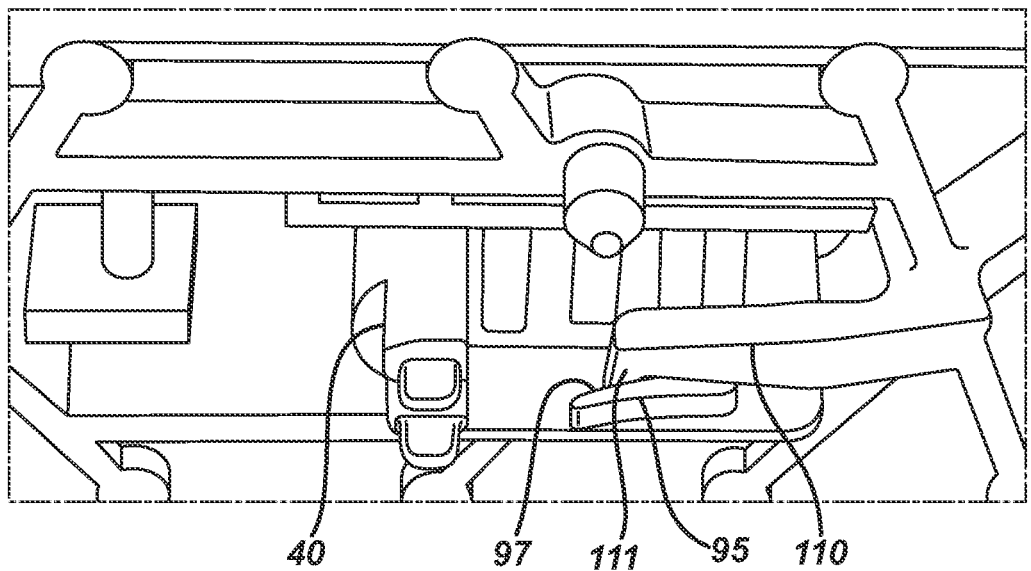
Figure 6C:
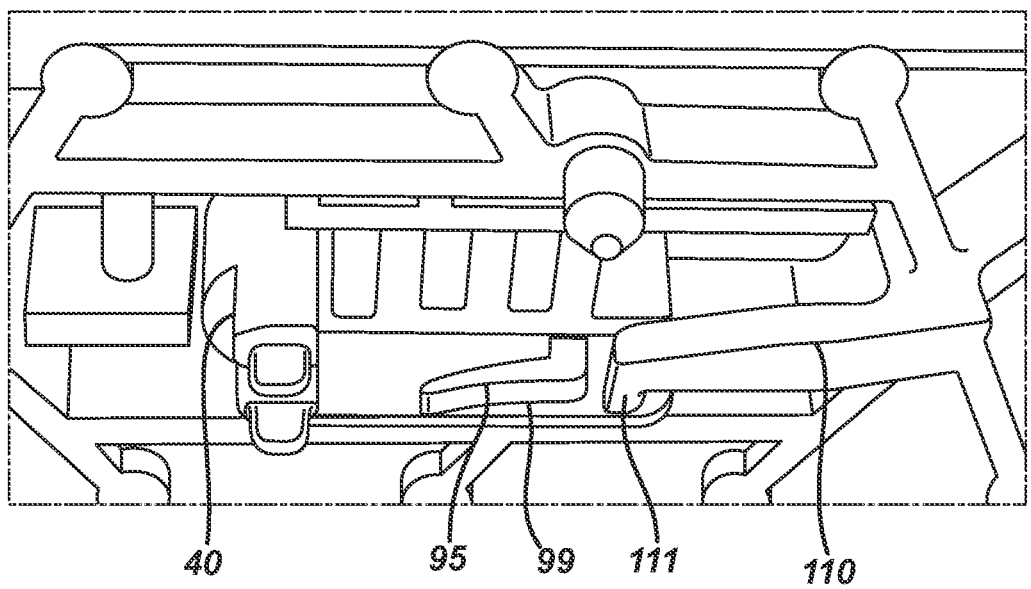

Referring to FIG. 6A, in one embodiment, when the actuator 40 is retracted to a proximal-most position, the free end 111 of the flexible element 110 is distal to a distal end of the ramp 95 and the flexible element 110 is in an undeflected state. In FIG. 6B, as the actuator 40 is moved distally for unlocking an insertion tip from the latching assembly, the free end 111 of the flexible element 110 slides over the top surface 97 of the ramp 95 for deflecting the flexible element 110 upwardly. Referring to FIG. 6C, when the free end 111 of the flexible element 110 clears the proximal end of the ramp 95, the flexible element 110 snaps back to an undeflected state for generating a first detectable click that indicates unlocking and release of the insertion tip. In FIG. 6C, the actuator 40 is in a distal-most position that coincides with the unlocking of an insertion tip from the latching assembly at the distal end of the insertion device. In one embodiment, after the insertion tip has been unlocked from the insertion device, the actuator 40 may be released by the surgeon whereupon the actuator return spring pulls the actuator in a proximal direction. As the actuator is pulled proximally, the free end 111 of the flexible element 110 slides over the bottom surface 99 of the ramp 95 for flexing the flexible element 110 downwardly. When the free end 111 of the flexible element 110 clears the distal end of the ramp 95, the flexible element 110 snaps back to an undeflected state (FIG. 6A) for generating a second detectable click indicating that the actuator 40 has returned to a proximal-most position.

Referring to FIG. 7A, in one embodiment, the insertion device includes the push wire 106 (FIG. 5A) having a proximal end 108 and a distal end 112. Although not shown in FIG. 7A, the push wire 106 preferably extends through an elongated conduit formed in the outer shaft 28 of the insertion device 20 (FIG. 5B). The push wire 106 is desirably flexible for conforming to the shape of the outer shaft. Referring to FIG. 7B, in one embodiment, the insertion device preferably includes a tip pin 114 that is provided at the distal end of the outer shaft 28. The tip pin 114 desirably includes a proximal end 116 and a distal end 118.

Figure 8:
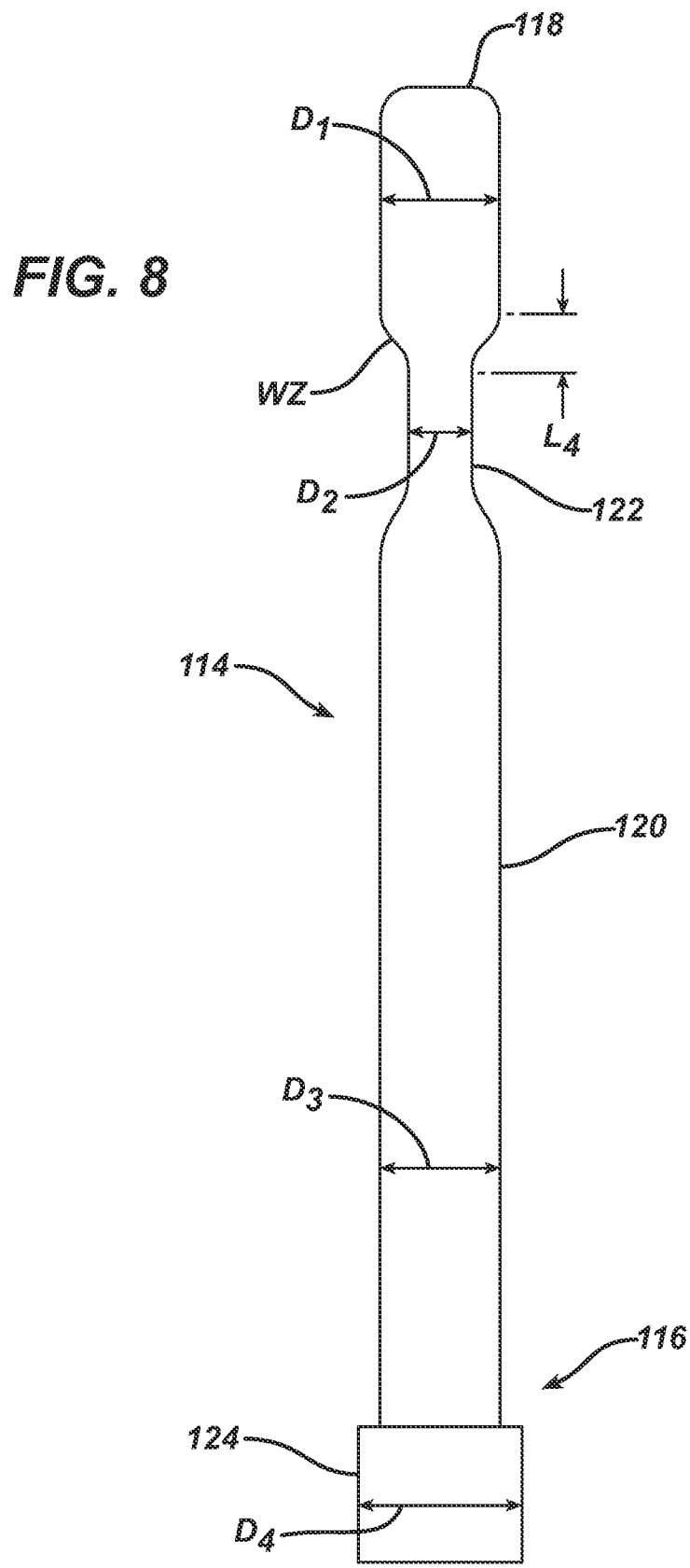
FIG. 8 shows a cross-sectional view of the tip pin shown in FIGS. 7A-7B, in accordance with one embodiment of the present invention.

Referring to FIG. 8, in one embodiment, the tip pin 114 preferably has an elongated shaft 120 having a distal end with an outer diameter $D_1$ of about 0.038"+/−0.001". The tip pin 114 has a reduced diameter neck 122 that is closer to the distal end 118 of the tip pin than the proximal end 116 thereof. The reduced diameter neck 122 has an outer diameter $D_2$ of about 0.024"+/−0.001", which is smaller than the outer diameter $D_1$. The proximal end 116 of the tip pin 114 has an outer diameter $D_3$ of about 0.036"+/−0.001". The tip pin 114 has an annular base 124 secured to the proximal end of the elongated shaft 120 having an outer diameter $D_4$ of about 0.050"+/−0.002" that is greater than the diameter $D_3$. In one embodiment, the tip pin 114 desirably has a work zone designated WZ having a length $L_4$ of about 0.010-0.020" and more preferably about 0.015". The work zone WZ includes a radial surface that slopes inwardly between the section of the tip pin having the outer diameter $D_1$ and the section of the tip pin having the outer diameter $OD_2$. The inner cam surfaces of the latches ride over the work zone WZ of the tip pin as the tip pin moves proximally and distally for moving the latches between a non-expanded state and an expanded state for unlocking and locking the insertion tip with a flexible latching assembly. In one embodiment, the tip pin moves axially about 0.015" for moving the latches between the non-expanded state and the expanded state.

Referring back to FIGS. 7A and 7B, the insertion device includes a flexible latching assembly 130 provided at the distal end of the outer shaft 28 (FIG. 1A). The flexible latching assembly 130 includes a first elastic latch 132 and a second elastic latch 134. The latches 132, 134 normally spring toward one another. Referring to FIG. 7B, in one embodiment, the flexible latching assembly 130 desirably includes a central conduit 136 adapted to receive the tip pin 114. The central conduit 136 has an inner diameter $ID_1$ of about 0.041"+/−0.002" that is equal to or greater than the outer diameters $D_1$ and $D_3$ at the respective distal and proximal ends of the tip pin 114. The outer diameter $D_4$ of the annular base 124 of the tip pin 114 is about 0.050"+/−0.002", which is greater than the inner diameter $ID_1$ of the central conduit 136 for halting distal movement of the tip pin 114 relative to the latching assembly once the annular base 124 of the tip pin abuts against the proximal end of the latching assembly 130. The first elastic latch 132 has an outwardly extending latch post 138 and an inner cam surface 140, and the second elastic latch 134 has an outwardly extending latch post 144 and an inner cam surface 146.

Referring to FIG. 7B, in one embodiment, an insertion tip 50 is pushed onto a distal end of the latching assembly 130 for moving the tip pin 114 in a proximal direction designated P. As the tip pin 114 moves proximally, the outer surface of the tip pin shaft 120, which is distal to the reduced diameter neck 122, engages the respective inner cam surfaces 140, 146 of the first and second latches 132, 134 for pushing the first and second latches 132, 134 away from one another. As the first and second latches 132, 134 flex away from one another, the latch posts 138, 144 are pushed into the opposing windows 62A, 62B of the insertion tip 50 for securing the insertion tip 50 to the latching assembly 130 at the distal end of the insertion device. In the position shown in FIG. 7B, the inner cam surfaces 140, 146 of the latches are in contact with the outer diameter $D_1$ at the distal end of the tip pin 114 (FIG. 8). The retracted tip pin 114 holds the latch posts 138, 144 in the extended position so that insertion tip 50 remains locked or secured to the distal end of the insertion device.

Referring to FIG. 7B, in one embodiment, the base 58 of the insertion tip 50 has a blind pocket 119 with a closed end wall. The blind pocket 119 is preferably located at a distal end of the central lumen and is distal to the opposing windows 62A, 62B. In one embodiment, the blind pocket 119 has a depth of about 0.010-0.030" and more preferably about 0.020". When the insertion tip 50 is locked onto the end of the latching assembly 130, the latches 132, 134 have latch extensions at distal ends thereof that extend into the blind pocket 119 for providing lateral stabilization of the insertion tip on the latching assembly.

In one embodiment, the opposing windows 62A, 62B have a length, extending along the longitudinal axis of the insertion tip 50, of about 0.030-0.070" and more preferably about 0.050". The latch posts 138, 144 of the respective first and second latches preferably have a length, extending along the longitudinal axis of the insertion tip 50, of about 0.025-0.030" and more preferably about 0.028". The lengths of the windows 62A, 62B are preferably longer than the lengths of the respective latch posts 138, 144 so that the latch posts can move axially relative to the windows while being retracted, which prevents any jamming between the latching assembly and the insertion tip. In one embodiment, the latch extensions desirably have a length of about 0.015-0.020", and more preferably about 0.019".

Figure 9:
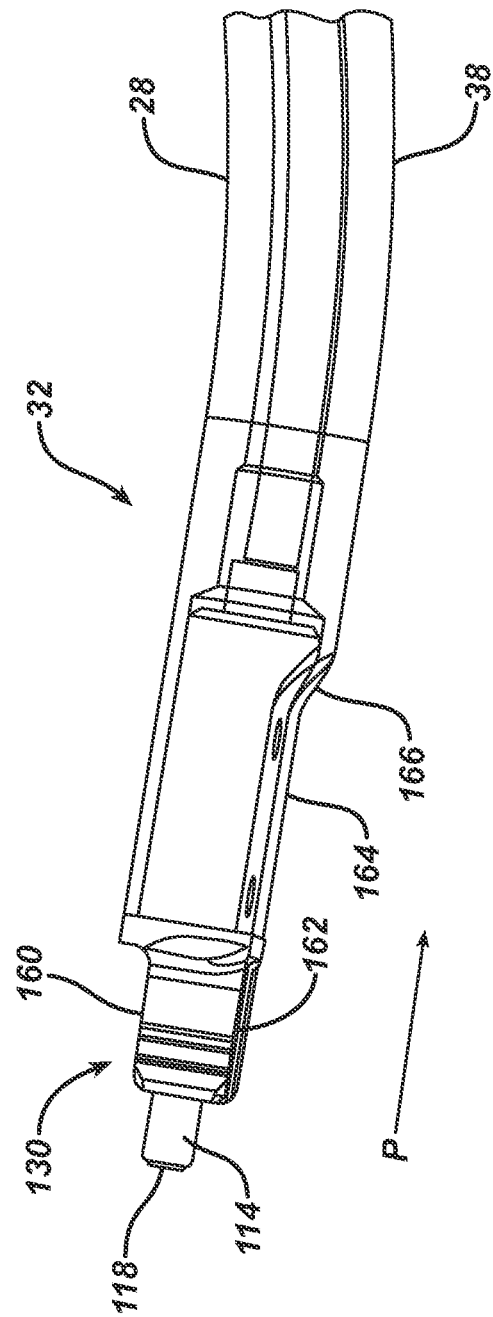
FIG. 9 shows a side elevation view of the distal end of the insertion device shown in FIG. 1A.

Referring to FIG. 9, in one embodiment, the outer shaft 28 has a curved section 38 that is proximal to the distal end 32 of the outer shaft. In one embodiment, the distal-most end of the outer shaft 28 (i.e. a section that is distal to the curved section 38) is straight. The flexible latching assembly 130 is disposed at the distal end 32 of the outer shaft 28. In one embodiment, the flexible latching assembly 130 includes a flat top surface 160 that is adapted to engage the top wall 86 of the central lumen 60 of the insertion tip 50 (FIG. 3D) and a flat bottom surface 162 that engages the bottom wall 85 of the central lumen 60 (FIG. 4). The distal-most end of the outer shaft 28 also includes a supplemental flat surface 164 that is generally co-planar with the flat bottom surface 162 of the latching assembly 130. When an insertion tip 50 is secured to the distal end 32 of the outer shaft 28, the supplemental surface 164 preferably engages the elongated flat surface 64 (FIG. 4) of the insertion tip 50 that is proximal to the bottom wall 85 of the central lumen. Although the present invention is not limited by any particular theory of operation, it is believed that providing the flat top surface 160 and the flat bottom surfaces 162, 164 properly orients the insertion tip 50 relative to the distal 32 of the outer shaft 28, and stabilizes the insertion tip when it is locked to the distal end of the insertion device.

Referring to FIG. 9, in one embodiment, before the insertion tip 50 (FIG. 4) is secured to the latching assembly 130, the distal end 118 of the tip pin 114 preferably projects beyond the distal end of the latching assembly 130. When an insertion tip is placed onto the latching assembly 130 and pushed proximally, the closed end wall of the central lumen 60 (FIG. 4) at the proximal end of the base 58 of the insertion tip 50 preferably abuts against the distal end 118 of the tip pin 114 for moving the tip pin in the proximal direction P.

In one embodiment, the outer shaft 28 has a sloping surface 166 that slopes inwardly between the outer surface of the outer shaft 28 and the supplemental flat surface 164. When an insertion tip 50 is secured to the distal end of the outer shaft 28, the sloping surface 66 at the proximal end 52 of the insertion tip 50 (FIG. 3B) preferably engages the sloping surface 166 on the outer shaft 28 for stabilizing the insertion tip at the distal end of the outer shaft 28.

Figure 10:
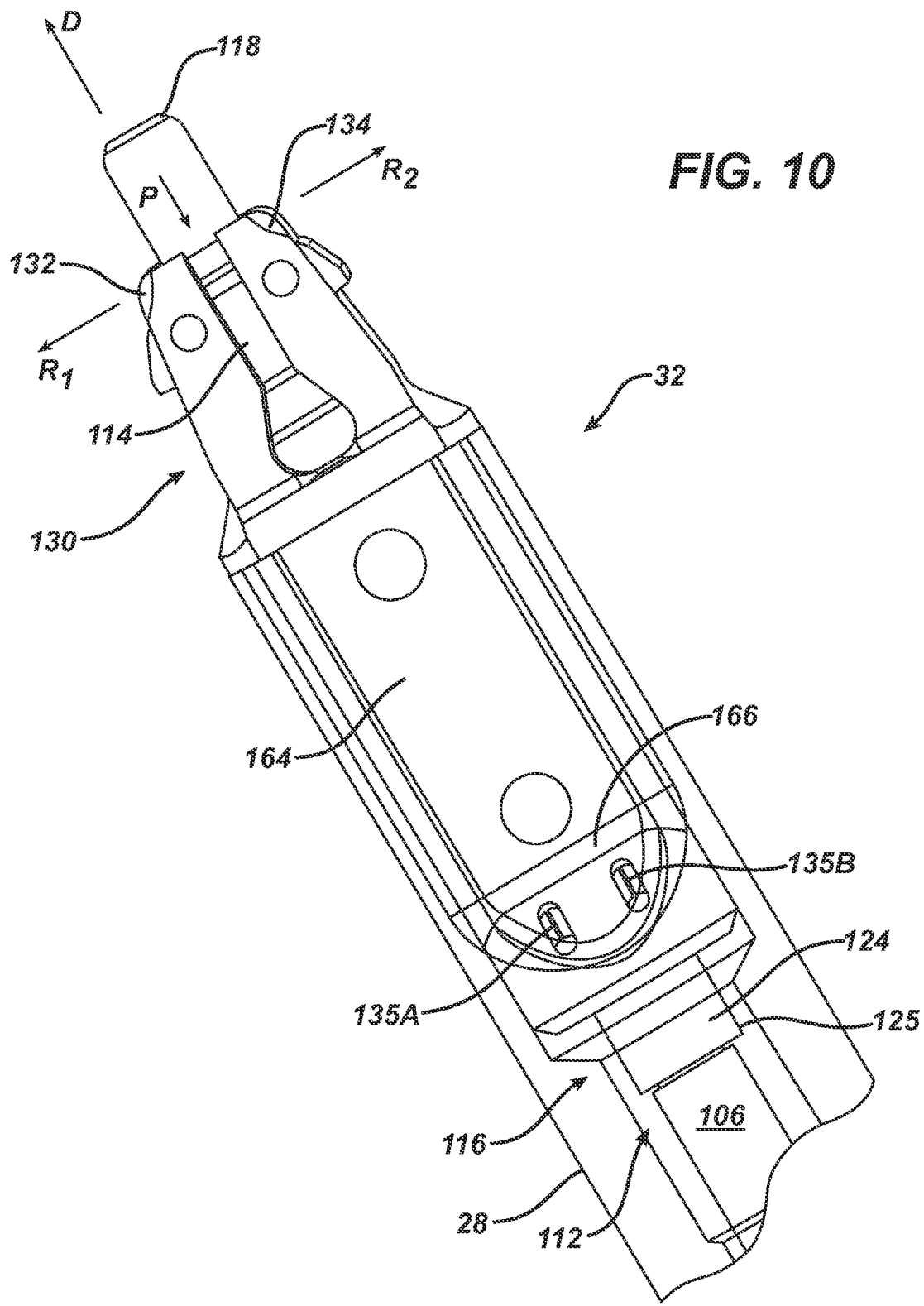
FIG. 10 shows a bottom plan view of the distal end of the insertion device shown in FIG. 9.

Referring to FIG. 10, in one embodiment, the distal end 32 of the outer shaft 28 includes the supplemental flat bottom surface 164 and the sloping surface 166. In one embodiment, the sloping surface 166 includes a pair of crushable ribs 135A, 135B. The ribs 135A, 135B may be crushed to form a connection between the proximal end of the latching assembly 130 and the distal end of the outer shaft 28 to ensure that there is no linear movement between the latching assembly 130 and the distal end of the outer shaft 28. In one embodiment, it is important that there is no linear movement between the latching assembly 130 and the distal end of the outer shaft 28 because any linear movement can adversely impact the unlocking function since the cam action occurs within a very small window having a length of about 0.010-0.020". The crushable ribs 135A, 135B preferably take up any material flex during the assembly process while ensuring that the reforming of the distal end of the outer tube does not change the inner diameter $ID_1$ of the central conduit 136 of the flexible latching assembly 130 (FIG. 7B), or impede distal and/or proximal movement of the tip pin 114.

The push wire 106 extends through a central conduit of the outer shaft 28 so that the distal end 112 of the push wire engages the annular base 124 at the proximal end 116 of the tip pin 114. The tip pin 114 has a distal end 118 that desirably projects beyond the distal end of the latching assembly 130. The tip pin 114 desirably includes a reduced diameter neck section 122 having a smaller diameter than the diameter of the tip pin adjacent the distal end 118 thereof. The flexible latching assembly 130 includes the first latch 132 projecting outwardly from a first side of the flexible latching assembly and a second latch 134 projecting outwardly from a second side of the flexible latching assembly. In one embodiment, when the tip pin 114 moves in the proximal direction P, the larger diameter section of the tip pin adjacent the distal end 118 thereof pushes the first and second latches 132, 134 outward, away from one another in the opposite radial directions $R_1$, $R_2$ for expanding the width of the flexible latching assembly 130 at the distal end thereof. In one embodiment, when the tip pin 114 is pushed in a distal direction D by the push wire 106, the reduced diameter neck 122 is advanced into alignment with the first and second latches 132, 134, whereby the first and second latches flex inwardly toward one another for reducing the width defined by the first and second latches 132, 134 at the distal end of the latching assembly 130.

The elongated conduit of the outer shaft 28 transitions to a larger bore area 125 to ensure that the annular base 124 at the proximal end of the tip pin does not move into the smaller diameter area of the elongated conduit of the outer shaft 28.

Figure 11A:
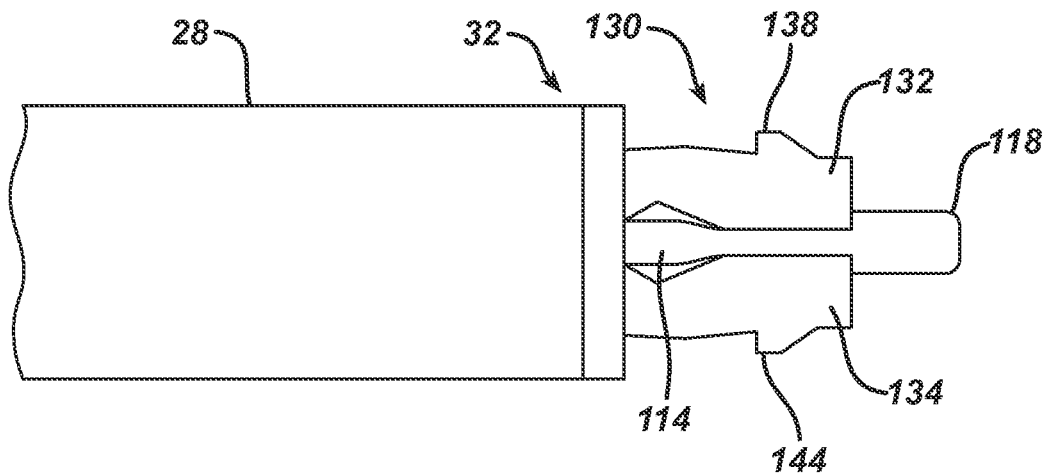
FIGS. 11A-11B shows the distal end of an insertion device with a latching assembly moving between a non-expanded state and an expanded state, in accordance with one embodiment of the present invention.
Figure 11B:
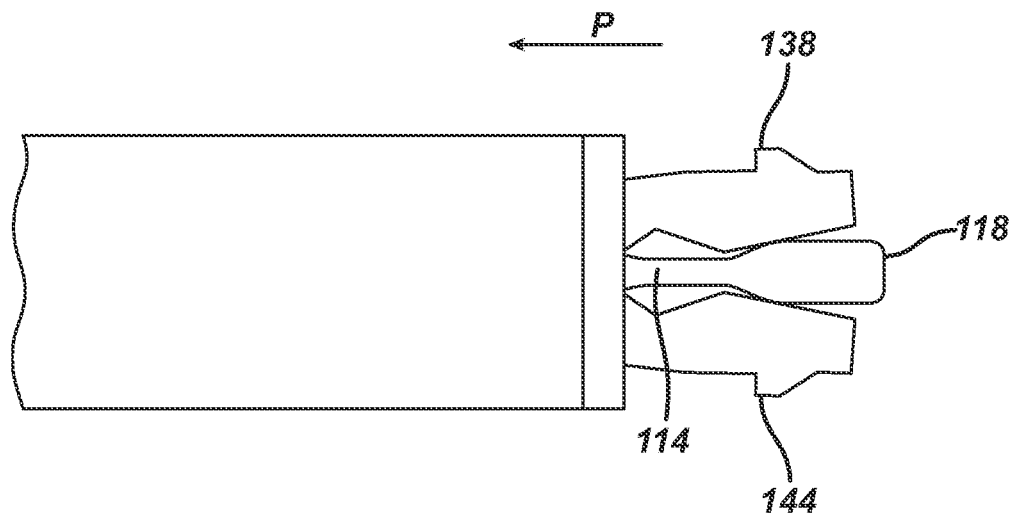

Referring to FIGS. 11A and 11B, in one embodiment, the flexible latching assembly 130 is located at the distal-most end 32 of an outer shaft 28. The latching assembly 130 is preferably flexible and includes a first latch 132 having a first latch post 138 projecting outwardly therefrom, and a second latch 134 having a second latch post 144 projecting outwardly therefrom. The tip pin 114 extends through a central opening of the latching assembly 130. The first and second latch posts preferably extend away from one another in opposite directions. In FIG. 11A, the tip pin 114 is fully extended so that the larger diameter distal end 118 of the tip pin 114 extends beyond the distal-most end of the first and second latches 132, 134. In one embodiment, the larger diameter distal end of the tip pin 114 extends about 0.060" beyond the distal-most end of the first and second latches. The reduced diameter neck section 122 of the tip pin 114 is in alignment with inner cam surfaces of the first and second latches 132, 134, whereby the latch posts 138, 144 are free to flex inwardly toward one another to provide a reduced width at the distal end of the flexible latching assembly 130.

Referring to FIG. 11B, in one embodiment, the tip pin 114 may be pushed in a proximal direction P so that the larger diameter section of the tip pin 114 adjacent the distal end 118 of the tip pin 114 is in alignment with the inner cam surfaces of the first and second latches 132, 134. In FIG. 11B, the larger diameter section at the distal end 118 of the tip pin 114 is aligned with the first and second latch posts 138, 144 for urging the first and second latch posts away from one another. As a result, the distal-most end of the flexible latching assembly 130 is wider than as shown in FIG. 11A, and the first and second latch post 138, 144 are spaced further away from one another than in the original position shown in FIG. 11A.

Figure 12A:
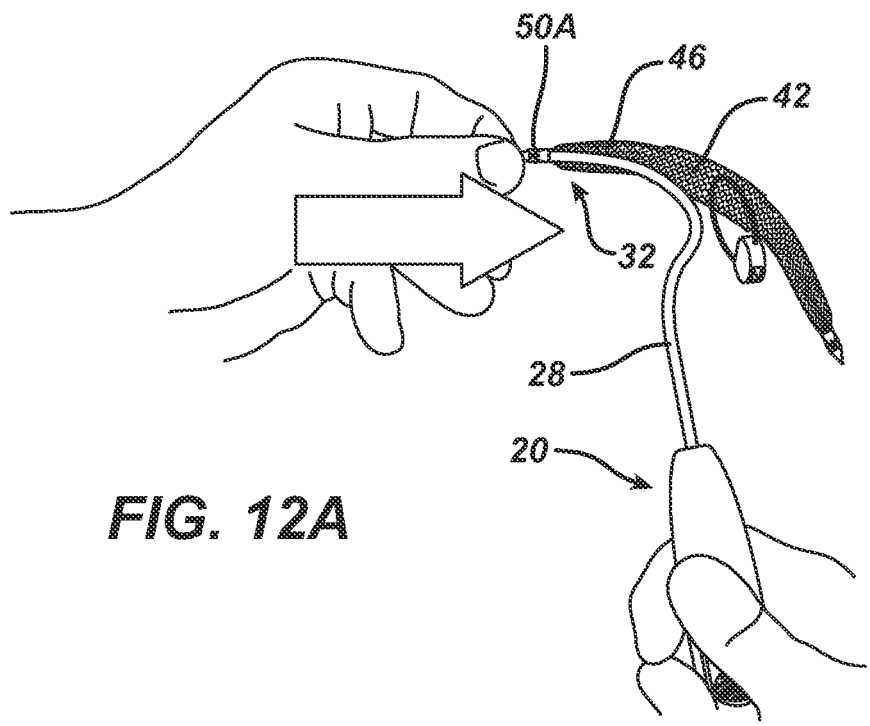
FIGS. 12A-12C show a method of self-locking and securing an insertion tip of an implant to a latching assembly at a distal end of an insertion device, in accordance with one embodiment of the present invention.
Figure 12B:
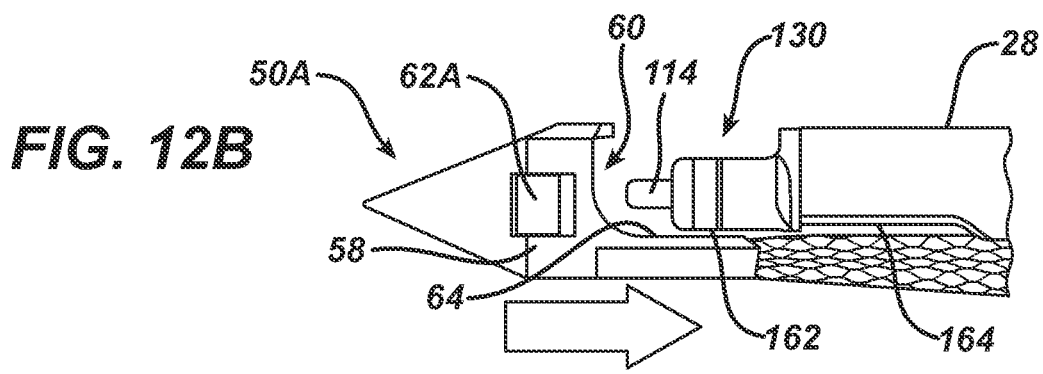
Figure 12C:
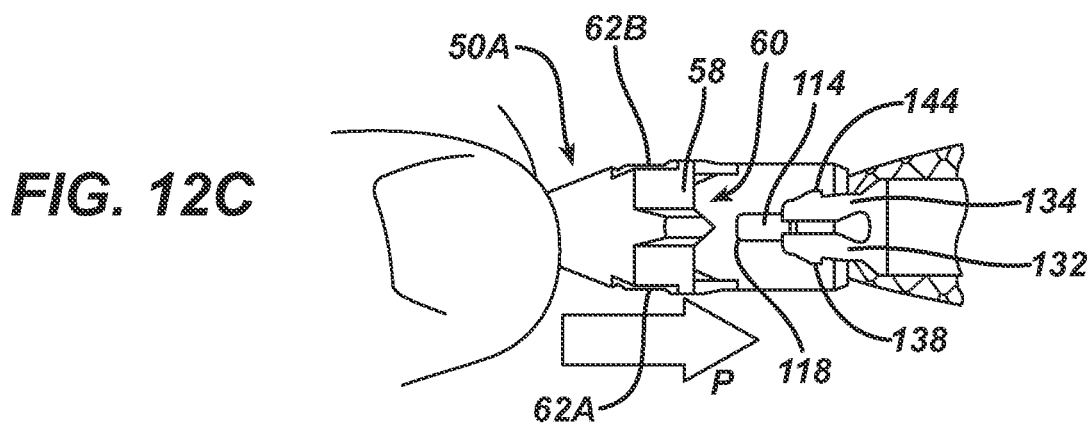

Referring to FIGS. 12A-12C, in one embodiment, an insertion tip 50A attached to the first arm 46 of an implant 42 is securable to a distal end 32 of an outer shaft 28 of an insertion device 20. Referring to FIGS. 12B and 12C, before the insertion tip 50A is pushed onto the latching assembly 130 at the distal end of the insertion device, the tip pin 114 preferably projects beyond the distal end of the flexible latching assembly 130. The tip pin 114 and the flexible latching assembly 130 are inserted into the central lumen 60 (FIG. 4) of the insertion tip 50A. The flat bottom surface 162 of the latching assembly 130 and the flat bottom surface 164 at the distal end of the outer shaft 28 are preferably juxtaposed with the bottom wall 85 of the central lumen 60 and the elongated flat surface 64 of the insertion tip 50A (FIG. 4). The first and second latch posts 138, 144 of the flexible latching assembly 130 are preferably in alignment with the windows 62A, 62B formed in the side wall 58 of the insertion tip 50.

In one embodiment, the insertion tip 50A is pushed in a proximal direction P until the closed end wall of the central lumen 60 abuts against the distal end 118 of the tip pin 114. After contact of the end wall with the distal end 188, further movement on the insertion tip 50A in a proximal direction results in engagement of the insertion tip 50A with the distal end 118 of the tip pin 114 for urging the tip pin to move in the proximal direction P. As the tip pin 114 moves in the proximal direction P, the wider diameter section of the tip pin 114 adjacent the distal end 118 thereof pushes the first and second latch post 138, 144 away from one another, whereupon the latch posts 138, 144 move into the opposing windows 62A, 62B of the insertion tip 50A for auto-locking the insertion tip to the latching assembly at the distal end of the insertion device.

Figure 13A:
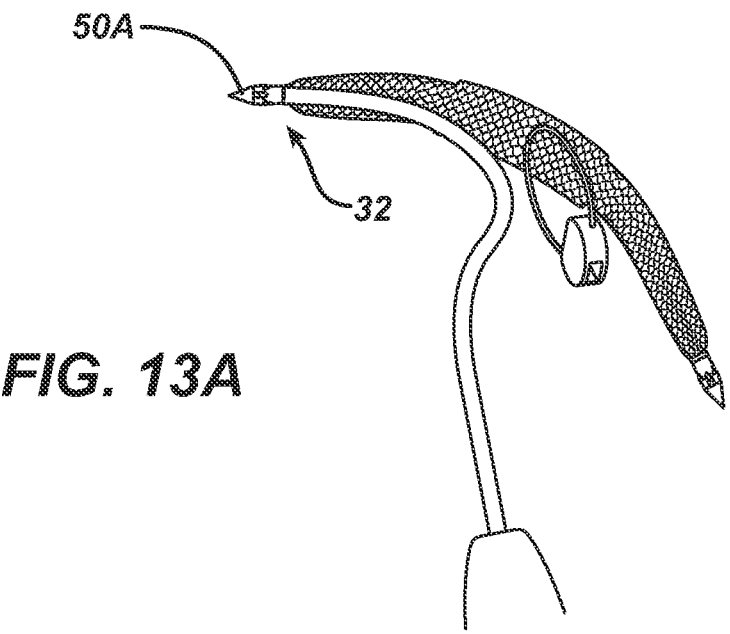
FIGS. 13A-13C show a method of attaching an insertion tip to a latching assembly of an insertion device, in accordance with one embodiment of the present invention.
Figure 13B:
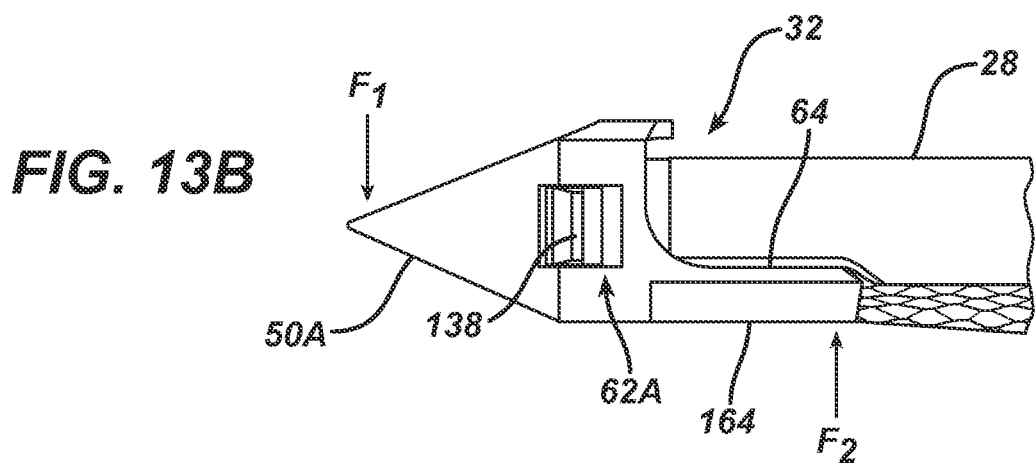
Figure 13C:
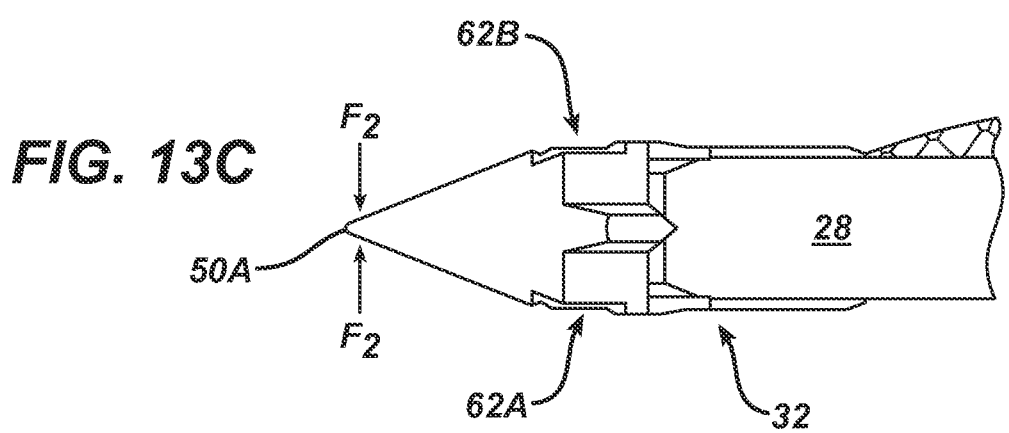

Referring to FIGS. 13A-13C, in one embodiment, when the insertion tip 50A is fully inserted onto the distal end 32 of the outer shaft 28 of the insertion device, the tip pin 114 (FIG. 12C) urges the first and second latch posts 138, 144 away from one another for moving into the respective first and second windows 62A, 62B of the insertion tip 50A. The first and second latch posts 138, 144 are held in the expanded state by the tip pin 114. Referring to FIG. 13B, in one embodiment, the elongated flat surface 64 extending to the proximal end 52 of the insertion tip 50A engages the flat surface 164 at the outside of the outer shaft 28 for providing rotational stability for counteracting rotational forces $F_1$ encountered during rotational use of the insertion device. The engagement between the elongated flat surface 64 and the flat surface 164 prevents rotation of the insertion tip and serves as a rotational stabilizer. Referring to FIG. 13C, in one embodiment, latch extensions at the distal-most ends of the first and second latches extend into the blind pocket 119 (FIG. 7B) formed in the base 58 of the insertion tip 50A for providing lateral stability for counteracting lateral forces $F_2$ when the insertion tip is locked to the latching assembly at the distal end of the insertion device. The first and second latch posts 138, 144 will continue to hold the insertion tip 50A onto the distal end 32 of the outer shaft 28 until the operator of the insertion device moves the tip pin in a distal direction so that the reduced diameter neck 122 (FIG. 8) of the tip pin 114 is once again in alignment with the inner cam surfaces of the first and second latches 132, 134 (FIG. 12C). Once the inner cam surfaces of the first and second latches 132, 134 are returned to alignment with the reduced diameter neck of the tip pin, the first and second latch posts 138, 144 flex inwardly for reducing the width at the distal end of the flexible latching assembly. At that point, the insertion tip is unlocked from the distal end of the insertion device and the first and second latch posts 138, 144 and the flexible latching assembly may be retracted from the central lumen 60 (FIG. 3B) of the insertion tip 50A.

Referring to FIG. 14A, in one embodiment, an insertion tip 50 is pushed onto the flexible latching assembly 130 at a distal-most end of an insertion device. Initially, the distal end 118 of the tip pin 114 extends beyond the distal-most end of first and second latches 132, 134. The insertion tip 50 has first and second windows 62A, 62B that are adapted to receive the respective latch posts 138, 144 on the respective first and second latches 132, 134. The first and second latches 132, 134 have inner cam surfaces 140, 146 that are initially seated within the reduced diameter neck section 122 of the tip pin 114. The distal end 118 of the tip pin 114 and the first and second latches 132, 134 are desirably inserted into the central lumen 60 of the insertion tip 50 (FIG. 3B).

Referring to FIG. 14B, in one embodiment, the insertion tip 50 is pushed in the proximal direction P until the closed end wall of the central lumen 60 abuts against the distal end 118 of the tip pin 114 for moving the tip pin 114 in the proximal direction P. The larger diameter section of the tip pin 114 adjacent the distal end 118 thereof engages the opposing inner cam surfaces 140, 146 of the respective first and second latches 132, 134 for moving the latch posts 138, 144 away from one another and advancing the latch posts into the windows 62A, 62B of the insertion tip 50. In one embodiment, the first and second windows 62A, 62B have an axial length of about 0.050", the latch posts 138, 144 have an axial length of about 0.028", and the latch extensions at the distal-most ends of the latches 132, 134 have a length of about 0.019".

Figure 14C:
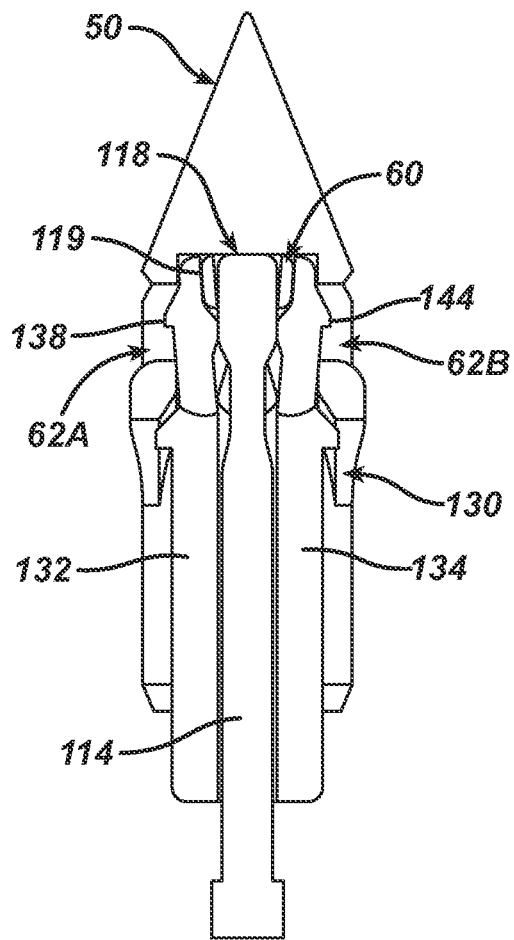

Referring to FIG. 14C, in one embodiment, when the tip pin is pushed proximally into a retracted position, the insertion tip 50 is fully seated onto the latching assembly 130 at the distal end of the insertion device. The closed end wall of the central lumen 60 of the insertion tip 50 urges the tip pin 114 to move proximally into the fully retracted position shown in FIG. 14C. The larger diameter section at the distal end 118 of the tip pin 114 urges the first and second latches 132, 134 away from one another, whereby the first and second latch posts 138, 144 are seated within the first and second windows 62A, 62B of the insertion tip 50 for securing the insertion tip 50 to the distal end of the insertion device. With the tip pin 114 is in the retracted position, the insertion tip 50 remains locked to the distal end of the insertion device because the latch posts 138, 144 are incapable of moving inwardly for unlocking the insertion tip 50 from the distal end of the insertion device. In FIG. 14C, the latch extensions at the distal-most ends of the latches 132, 134 have a length of about 0.019" and the blind pocket 119 seats the latch extensions for providing lateral stability for the insertion tip. The blind pocket 119 preferably has a depth of about 0.020". In the state shown in FIG. 14C, the insertion device may be utilized for inserting the insertion tip 50 and the implant into tissue at a desired location. With the insertion tip locked to the latching assembly, the insertion tip may also be retracted in tissue for repositioning the insertion tip during surgery. The insertion tip 50 will remain firmly locked to the distal-most end of the insertion device as long as the tip pin 114 is in the retracted position shown in FIG. 14C.

Figure 14D:
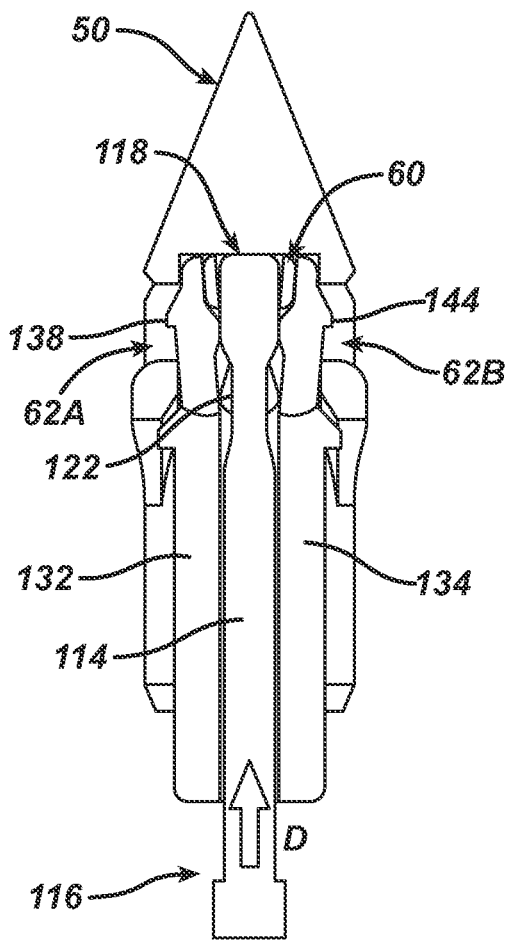
FIGS. 14D-14F show a cross-sectional view of a method of unlocking an insertion tip from a latching assembly at a distal end of an insertion device, in accordance with one embodiment of the present invention.
Figure 14E:
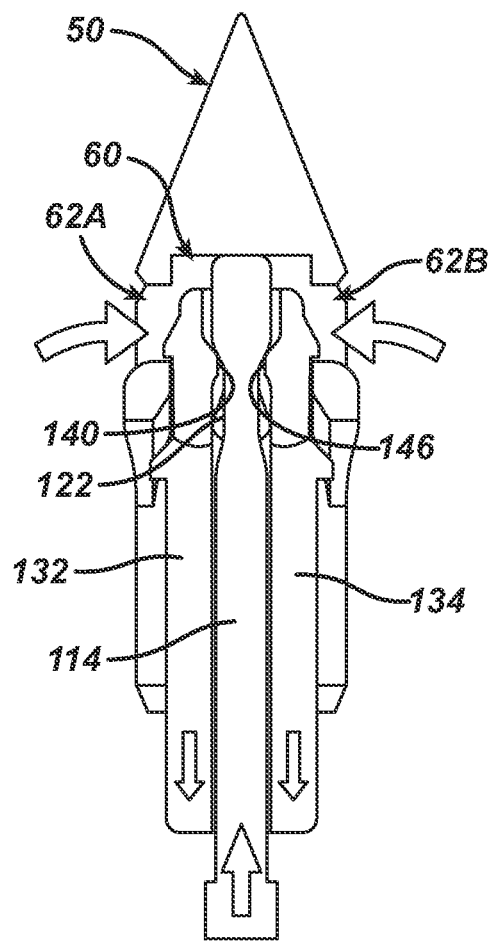
Figure 14F:
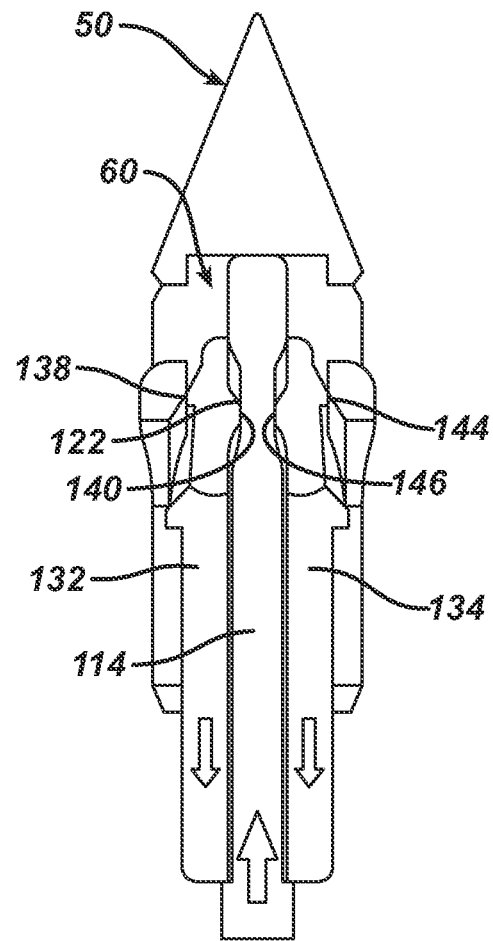

Referring to FIGS. 14D-14F, in one embodiment, after the insertion device has been used for inserting the insertion tip 50 into tissue at a desired location, a surgeon may seek to unlock the insertion tip from the distal end of the insertion device. In one embodiment, a surgeon may engage the actuator 40 on the handle 22 (FIG. 5A) for urging the push wire 106 to move in the distal direction D. After the push wire has moved a predetermined distance, a distal-most end 112 of the push wire 106 will engage the annular base 124 at the proximal end 116 of the tip pin 114 (FIG. 10) for moving the tip pin 114 in the distal direction D. At this stage, the actuator generates the detectable click and the actuator resets to the start position. As the tip pin 114 moves distally, the distal end 118 of the tip pin 114 provides a distal force on the closed end wall of the central lumen 60 of the insertion tip 50, which, in turn, moves the first and second latch posts 138, 144 in a proximal direction so that the inner cam surfaces of the first and second latches 132, 134 are once again aligned with the reduced diameter neck 122 of the tip pin. The first and second windows 62A, 62B have respective lengths that are greater than the lengths of the first and second latch posts 138, 144 so that the first and second latch posts 138, 144 may initially move proximally before they begin to move inwardly toward one another for retracting the latch posts from the first and second windows 62A, 62B, thereby preventing a jam condition between the inner cam surfaces of the latches and the tip pin. Although the present invention is not limited by any particular theory of operation, it is believed that this structure enables the distal end of the insertion device to be detached from the insertion tip 50 without moving the insertion tip from the desired location once placed in tissue.

FIG. 14E shows further proximal movement of the first and second latches 132, 134 whereupon the opposing inner cam surfaces 140, 146 of the first and second latches move into alignment with the reduced diameter neck 122 of the tip pin 114 so that the first and second latch posts 138, 144 are free to flex inwardly toward one another for being retracted from the opposing windows 62A, 62B of the insertion tip 50.

FIG. 14F shows the inner cam surfaces 140, 146 of the first and second latches 132, 134 fully seated within the reduced diameter neck 122 of the tip pin 114 with the first and second latches 132, 134 fully retracted, whereby the width defined by the first and second latch posts 138, 144 is smaller than the diameter of the central lumen 60 of the insertion tip 50. The smaller width of the flexible latching assembly 130 enables the distal end of the insertion device to be removed from the central lumen 60 of the insertion tip 50.

Figure 15A:
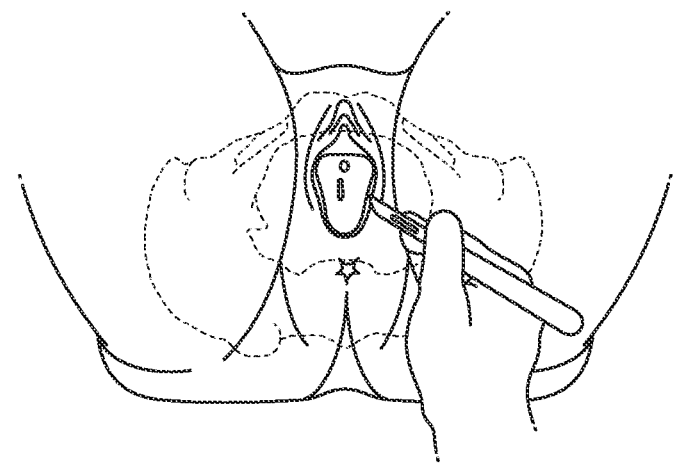
FIGS. 15A-15Y show a method of using an implant insertion system for treating a patient, in accordance with one embodiment of the present invention.

Referring to FIG. 15A, in one embodiment, a procedure for inserting an implant in a patient includes placing the patient in a dorsal lithotomy position with the legs flexed about 90° and the tip of the coccyx positioned flush with the edge of a table. The surgical procedure may be carried out under local, regional or general anesthesia. A urethral catheter may be inserted into the patient's bladder for emptying the bladder prior to the procedure.

In one embodiment, at the level of the mid urethra, a small amount of anesthesia may be injected submucosally to create a space between the vaginal wall and the periurethral fascia. Using a scalpel, and starting about 1 cm proximal to the urethral meatus, a sagittal incision of no more than 1.5 cm in length is desirably made. The incision is preferably positioned over the mid-urethral zone and will allow for subsequent passage of the implant.

Figure 15B:
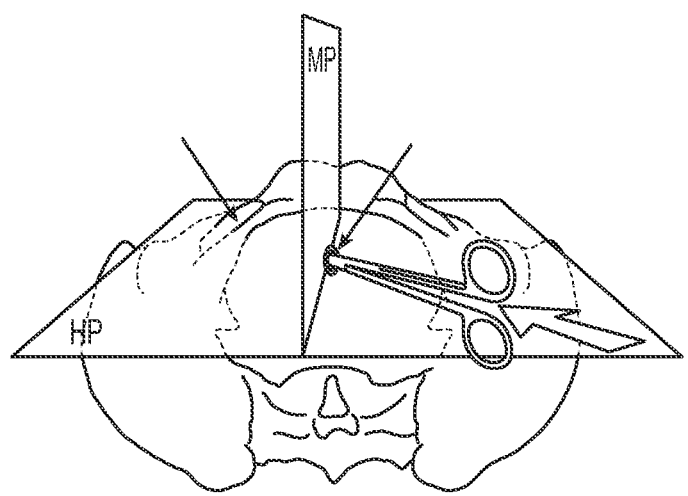

Referring to FIG. 15B, in one embodiment, after initiating sharp dissection, the surgeon continues to make a narrow blunt dissection toward, but not into, the obturator membrane using pointed, curved scissors parallel to the floor. The surgeon preferably makes left and right periurethral incisions just into the obturator internus muscle and behind the ischiopubic ramus (IPR). Surgical personnel should not dissect beyond the obturator internus muscle. The path of the lateral dissection should preferably be in a horizontal plane directed toward the ischio-pubic ramus in a 45° angle in relation to the coronal plane. The goal of the dissection is to create a channel that is sufficiently wide enough for insertion of a winged guide, as will be described in more detail below. In FIG. 15B, the horizontal plane is designated HP and the midline plane is designated MP.

Figure 15C:
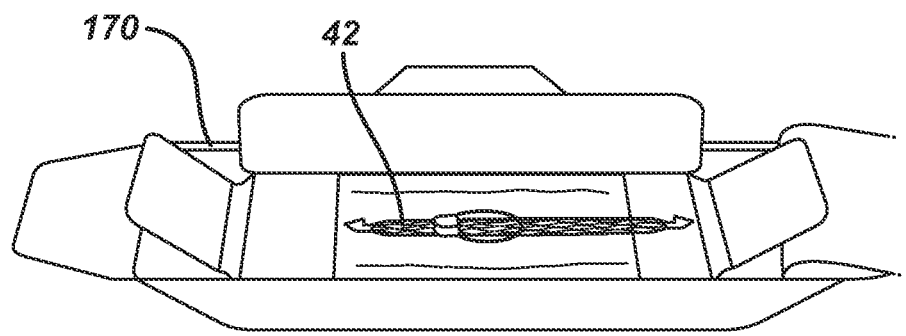

Referring to FIG. 15C, in one embodiment, an implant 42, such as that shown and described above in FIG. 2A, is removed from a sterile package 170 and positioned on a sterile drape or other suitable sterile location until needed.

Figure 15D:
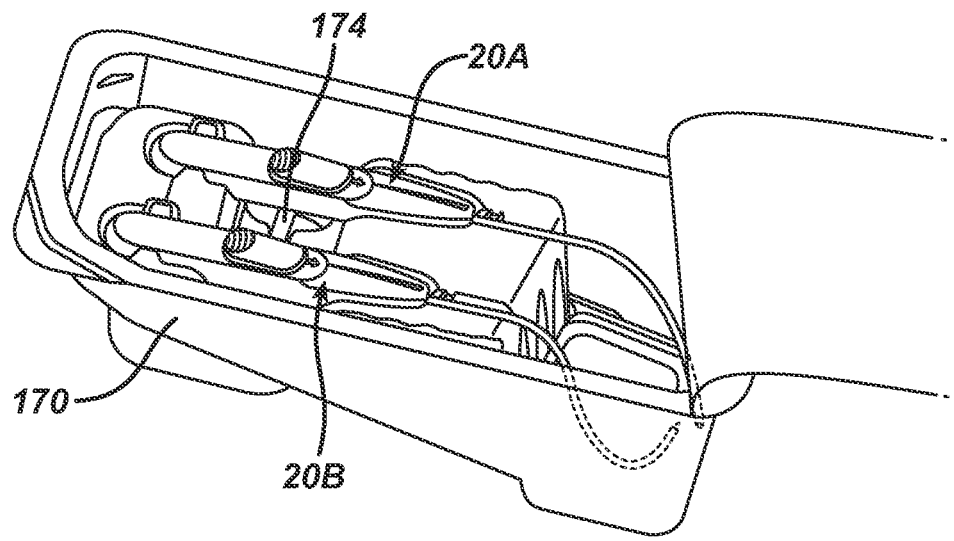

Referring to FIG. 15D, in one embodiment, a left-hand insertion device 20A and a right-hand insertion device 20B are removed from the sterile package 170 and placed upon a sterile drape or other suitable sterile location until needed. The sterile package 170 contains a winged guide 174 that is utilized for facilitating insertion of the implant 42 (FIG. 15C), as will be described in more detail herein. The winged guide 174, after being removed from the sterile package 170, is preferably placed atop a sterile drape or other suitable sterile location until needed.

Figure 15E:
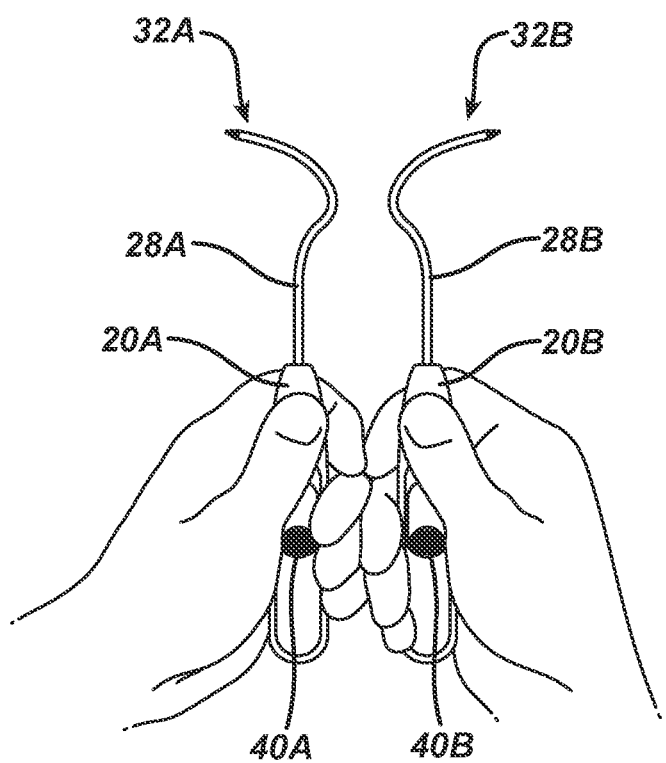

Referring to FIG. 15E, in one embodiment, the surgeon preferably ensures proper orientation of the left-hand insertion device 20A and the right-hand insertion device 20B. When properly oriented, the left-hand insertion device 20A is held by the surgeon's left-hand with the product logo and the actuator button 40A facing toward the surgeon so that the surgeon may engage the actuator button 40A with his/her left thumb. The distal end 32A of the outer shaft 28A preferably extends to the left. The left-hand insertion device 20A in the surgeon's left hand is preferably used on the patient's right side.

The surgeon preferably orients the right-hand insertion device 20B so that the product logo and the actuator 40B are facing toward the surgeon so that the surgeon may engage the actuator button 40B with his/her right thumb. The distal end 32B of the outer shaft 28B preferably extends to the right, which is away from the distal end 32A of the outer shaft 28A of the left-hand insertion device 20A. The right-hand insertion device 20B in the surgeon's right-hand is preferably used on the patient's left side.

Figure 15F:
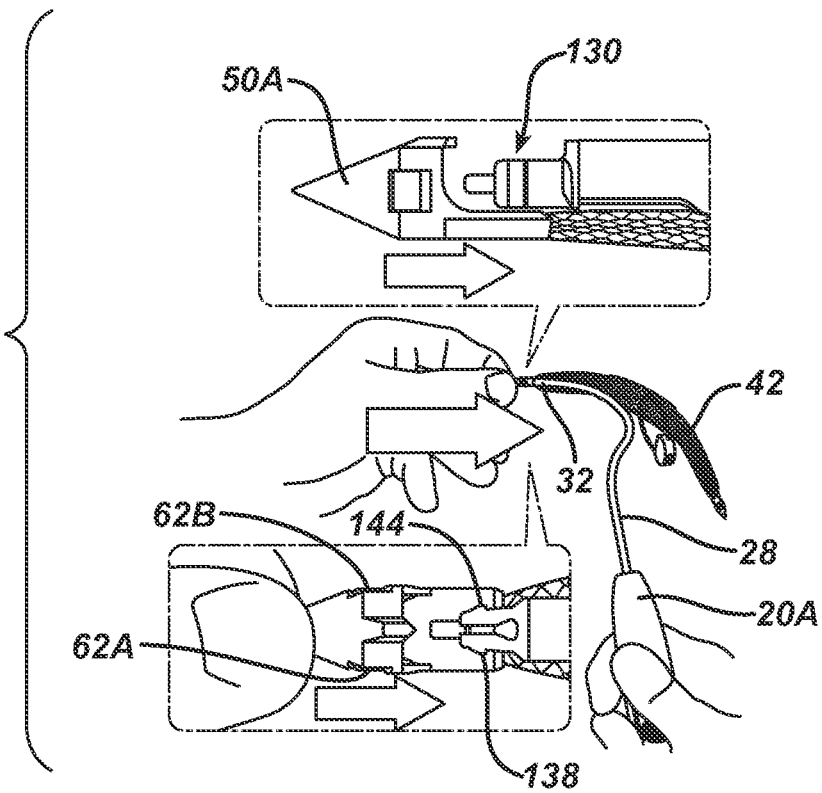
Figure 15G:
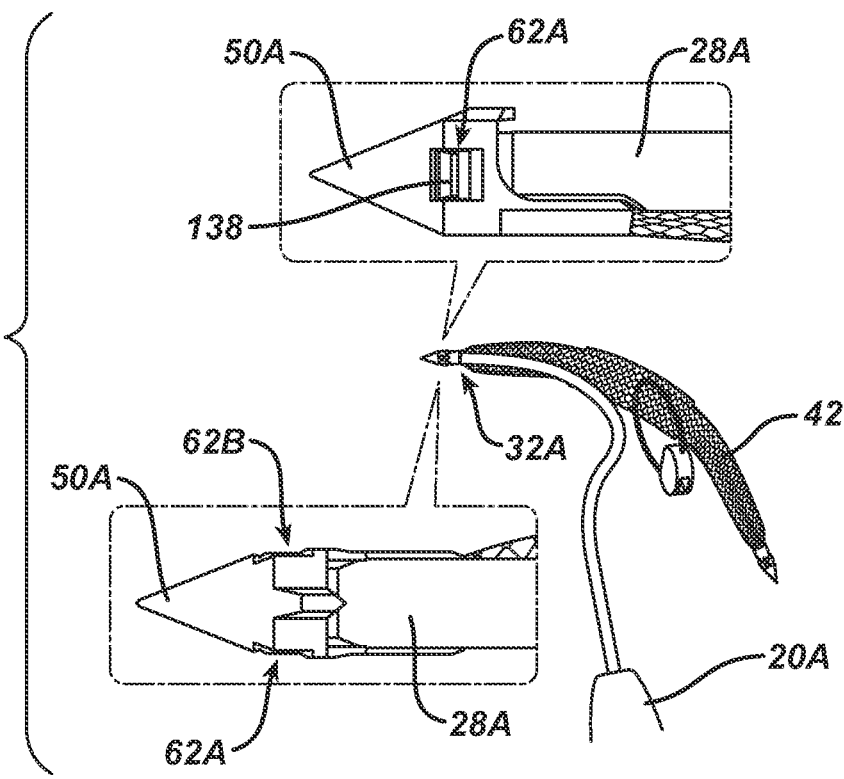

Referring to FIG. 15F, in one embodiment, the surgeon aligns the first insertion tip 50A of the implant 42 with the flexible latching assembly 130 at the distal end 32 of the outer shaft 28 of the left-hand insertion device 20A. Referring to FIGS. 15F and 15G, as the first insertion tip 50A is pushed onto the distal end of the outer shaft 28A, the latch posts 138, 144 extend into the opposing windows 62A, 62B of the first insertion tip 50A for attaching the first insertion tip to the distal end 32A of the left-hand insertion device 20A.

Figure 15H:
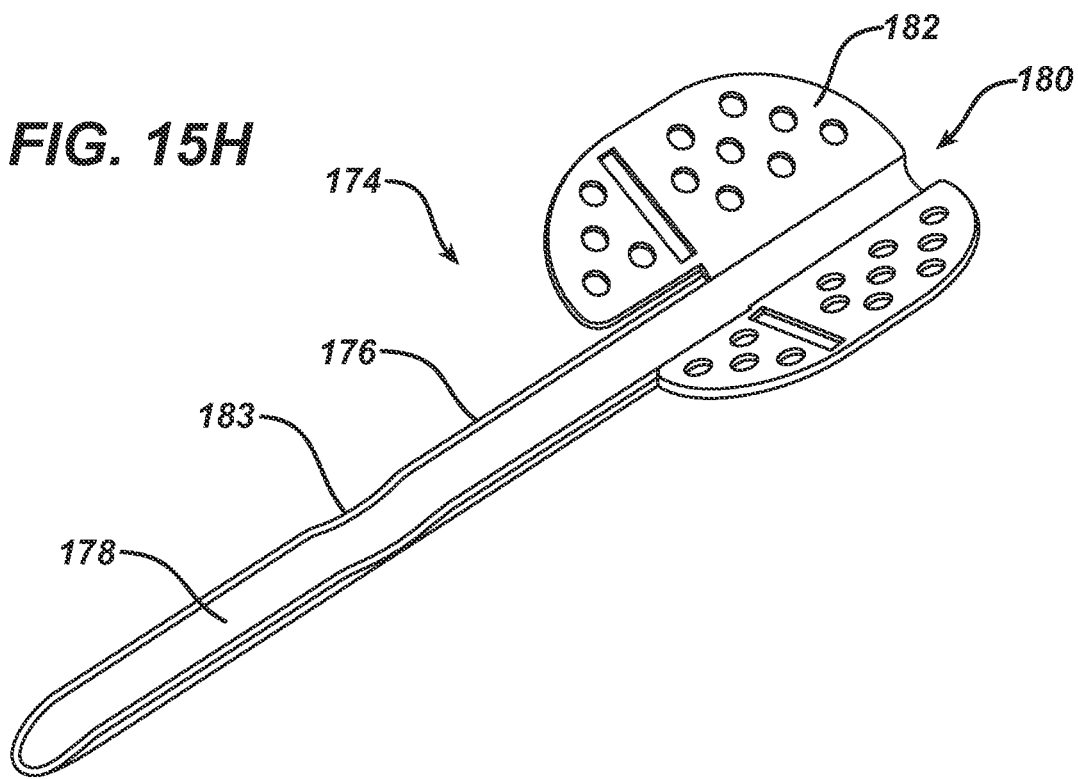

Referring to FIG. 15H, in one embodiment, after the left-hand insertion device has been secured to the first insertion tip 50A of the implant 42 (FIG. 15G), the winged guide 174 is utilized for properly inserting the first insertion tip 50A and the first arm of the implant into the dissected opening. In one embodiment, the winged guide 174 preferably has an elongated shaft 176 including a U-shaped channel 178 extending along the length thereof. The U-shaped channel 178 preferably guides the outer shafts of the insertion devices as they are advanced into the dissection opening. In one embodiment, the winged guide 174 provides a correct trajectory and path for the insertion devices through tissue to avoid bladder and urethral injuries. The elongated shaft 176 of the winged guide 174 has a proximal end 180 and a gripping flange 182 extending from opposite sides of the proximal end 180. In one embodiment, the gripping flange 182 has a V-shaped configuration. In one embodiment, the winged guide 174 includes a cut-out 183 located midway between the ends of the elongated shaft 176. The cut-out 183 preferably defines an insertion zone along the length of the elongated shaft 176. During a surgical procedure, the cut-out 183 is desirably used by a surgeon to limit excessive insertion of the elongated shaft into tissue so as to avoid premature perforation of the obturator membrane. In one embodiment, a surgeon will preferably halt insertion of the elongated shaft 176 when the cut-out 183 has been advanced into alignment with the exterior surface of the surgical opening.

Figure 15I:
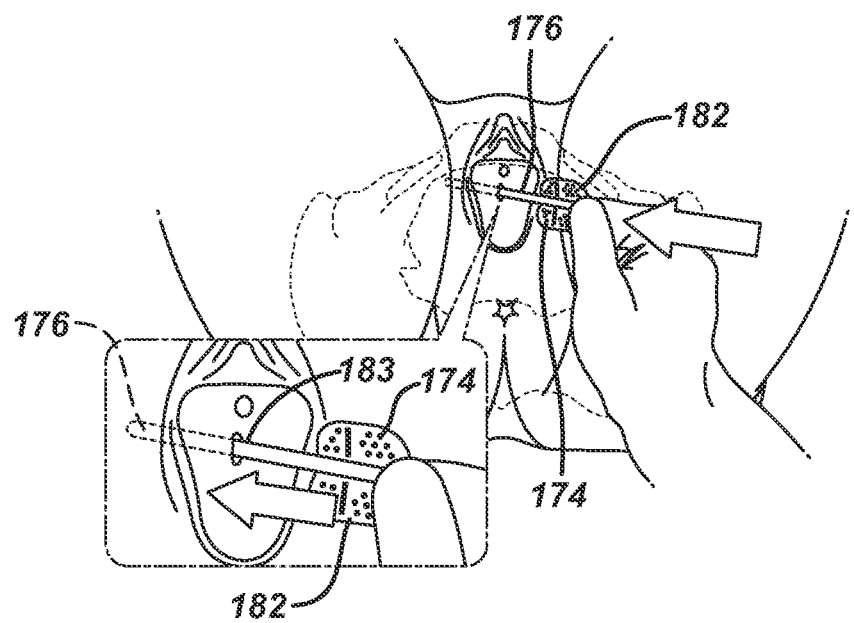

Referring to FIG. 15I, in one embodiment, the distal end of the U-shaped shaft 176 of the winged guide 174 is inserted into the dissected tract until the distal end of the shaft 176 reaches the ischio-pubic ramus and extends slightly into the obturator internus muscle. Preferably, surgical personnel will refer to the cut-out 183 provided on the elongated shaft 176 to halt advancement of the winged guide 174 so that the distal end of the U-shaped shaft 176 does not perforate the obturator membrane. Advancement beyond this preferred insertion zone may allow unintended entry into the obturator membrane or the space of Retzius. In one embodiment, if boney contact is not achieved after insertion of the winged guide 174 within the insertion zone, surgical personnel may preferably remove and re-evaluate the angle of dissection. If the surgeon encounters difficulty during insertion of the winged guide 174, the surgeon may re-confirm the direction of the dissected tract with scissors. The path of the winged guide 174 is desirably in a horizontal plane, directed toward the ischio-pubic ramus in a 45° angle in relation to the coronal plane.

Figure 15J:
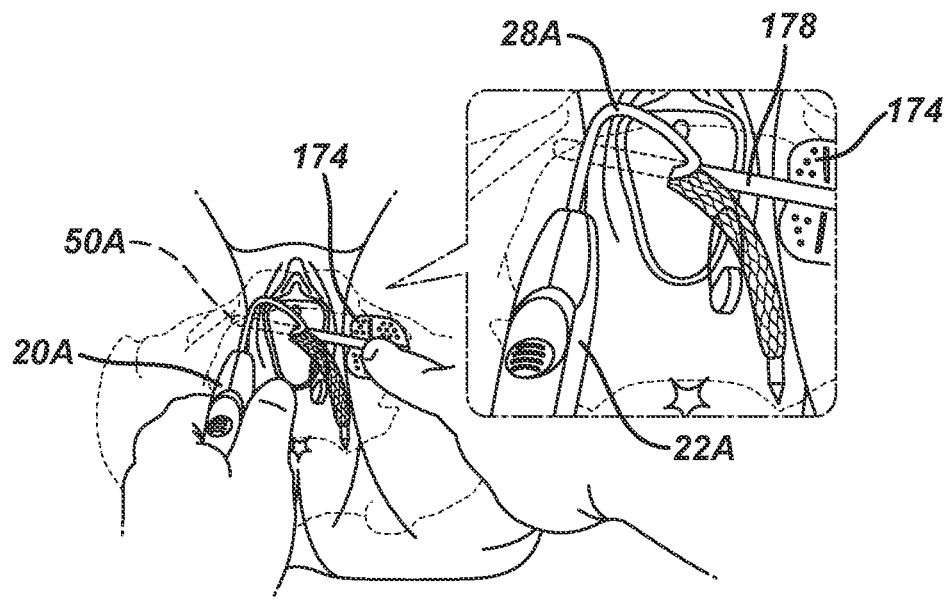

In one embodiment, during insertion of the winged guide 174, the obtuse or open side of the U-shaped channel 178 (FIG. 15H) of the winged guide 174 should face the surgeon and the gripping flange 182 should be pressed tightly against the patient's contra-lateral thigh. Referring to FIG. 15J, in one embodiment, while the surgeon holds the winged guide 174, the distal end of the left-hand insertion device 20A and the first insertion tip 50A connected therewith is inserted into the dissected tract following the U-shaped channel 178 of the winged guide 174 (FIG. 15H). The surgeon should preferably ensure that the handle 22A of the left-hand insertion device is oriented so that the straight section at the distal end 32A of the outer shaft 28A is aligned with the U-shaped channel 178 of the winged guide 174, and that the straight section at the distal end 32A remains in that orientation until the insertion tip reaches and/or contacts the superior border of the inferior ischo-pubic ramus and is pushed slightly into the obturator internus muscle, such that the insertion tip is not advanced into the obturator membrane.

Figure 15K:
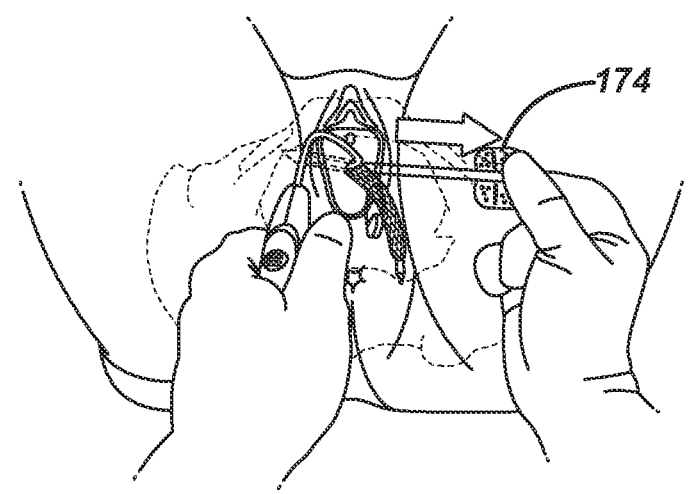

Referring to FIG. 15K, in one embodiment, after the step shown in FIG. 15J, the surgeon removes the winged guide 174 from the patient. The winged guide 174 is preferably maintained in a sterile condition for later use on the patient.

Figures 1, 15L:
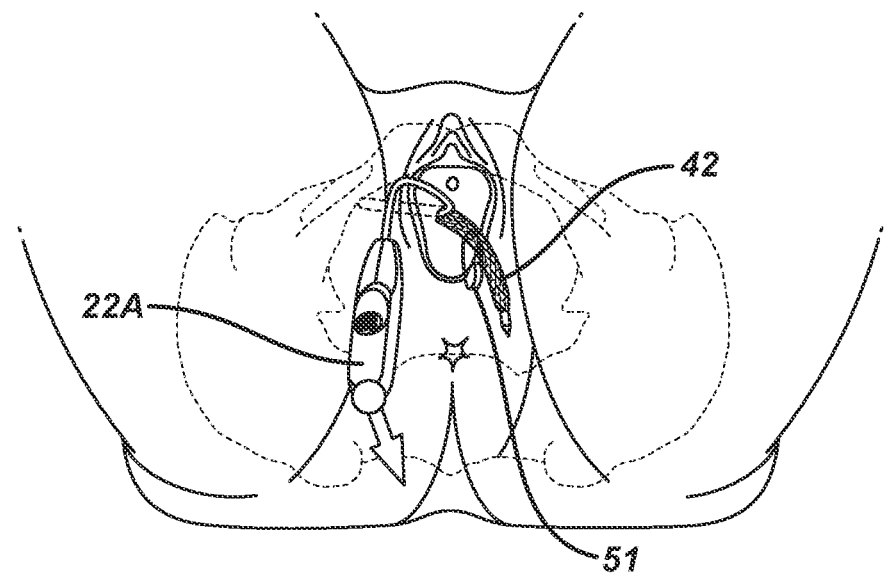
FIG. 1B shows a top plan view a left-hand insertion device and a right-hand insertion device of an implant insertion system, in accordance with one embodiment of the present invention.
Figures 2, 15L:
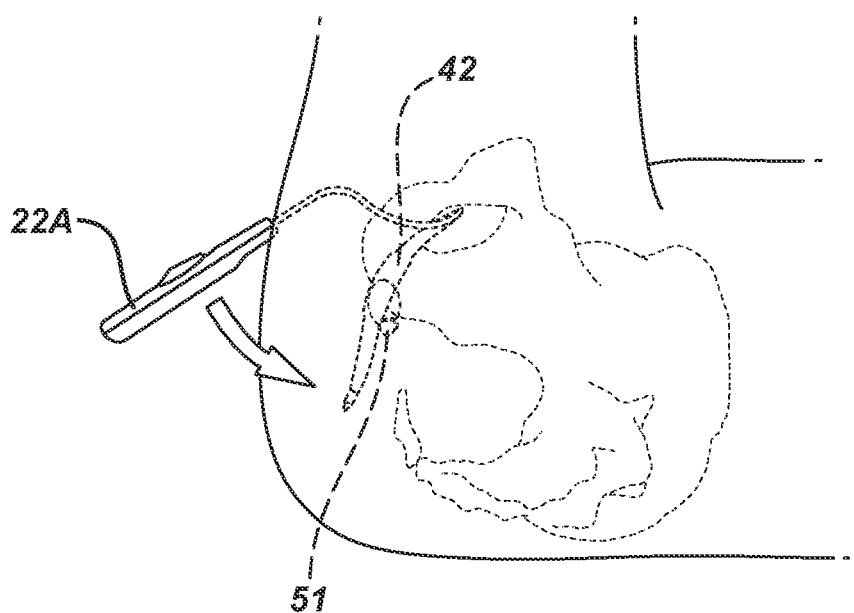
FIG. 2B shows the implant of FIG. 2A and the left-hand and right-hand insertion devices of FIG. 1B.
Figures 1, 15M:
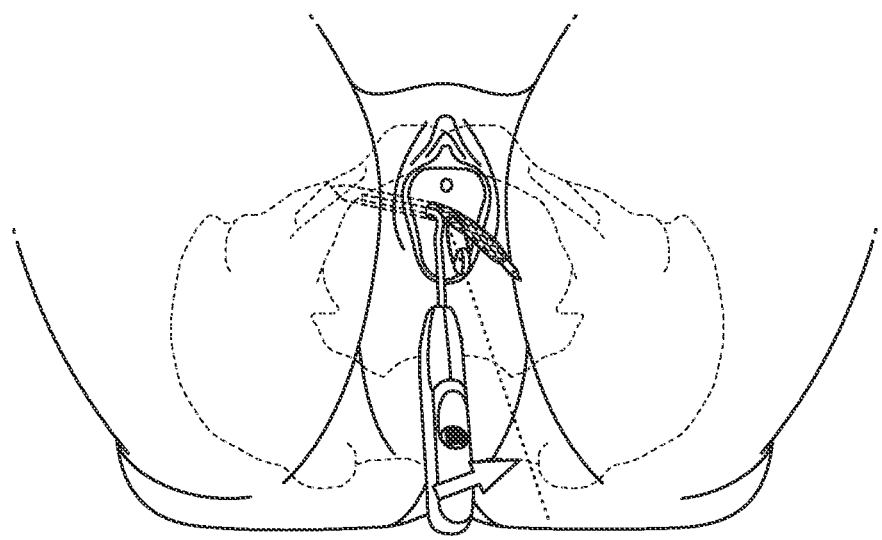
Figures 2, 15M:
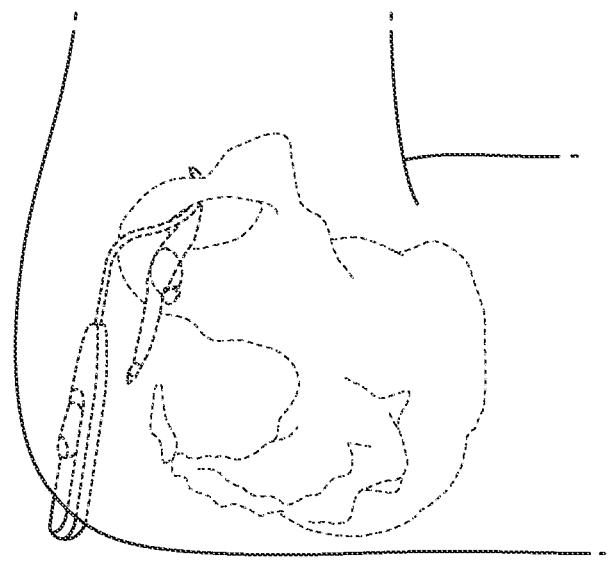
Figures 1, 15N:
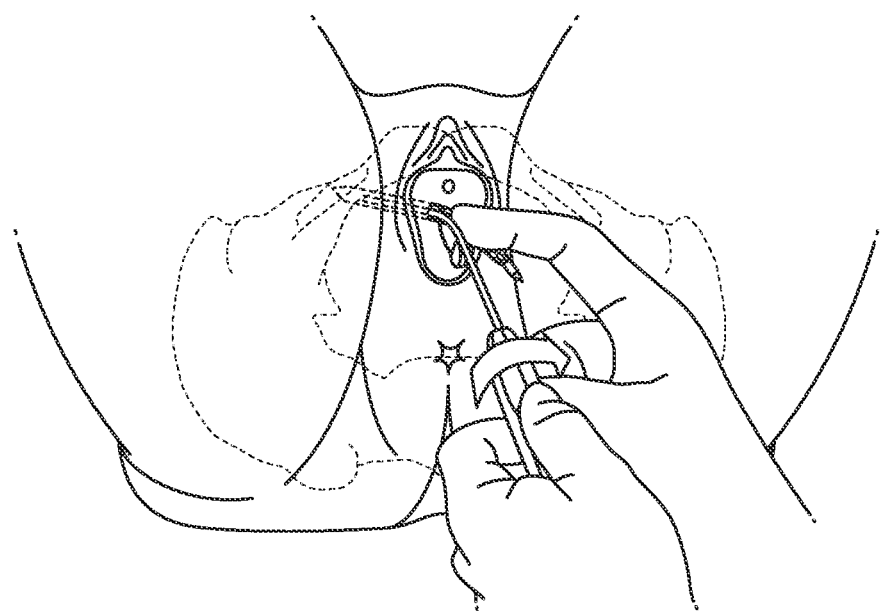
Figures 2, 15N:
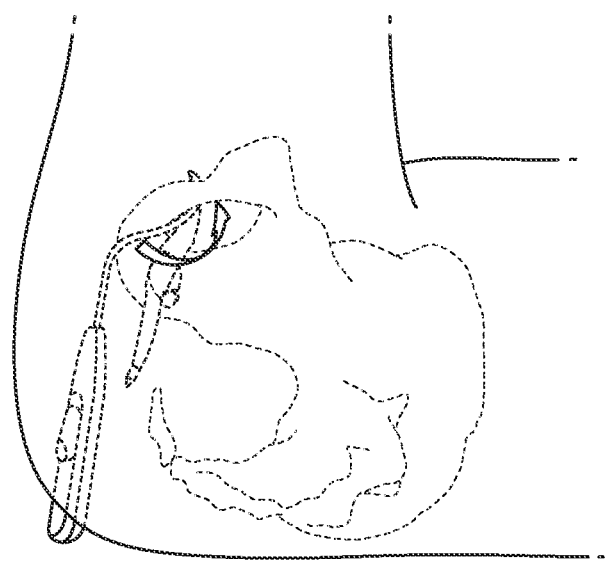

In one embodiment, the handle of the insertion device is lowered toward the table so that the handle is nearly vertical. The handle is then moved past the patient's midline over to the contralateral side. Using a free hand, the surgeon desirably pushes the insertion device until the insertion tip passes through the obturator membrane. The insertion device is then rotated while keeping the leading edge of the inserter in contact with the ischio-pubic ramus, stopping when the insertion tip has passed through the obturator membrane and is positioned in the obturator externus muscle. At this stage, the placement loop is preferably about 5 mm before center on the patient's first insertion side. FIGS. 15L-1 and 15L-2 show the start position of the inserter handle 22A from front and side views, respectively. FIGS. 15M-1 and 15M-2 show the intermediate position of the inserter handle 22A from front and side views, respectively. FIGS. 15N-1 and 15N-2 show the end position of the inserter handle 22A from front and side views, respectively.

Figure 15O:
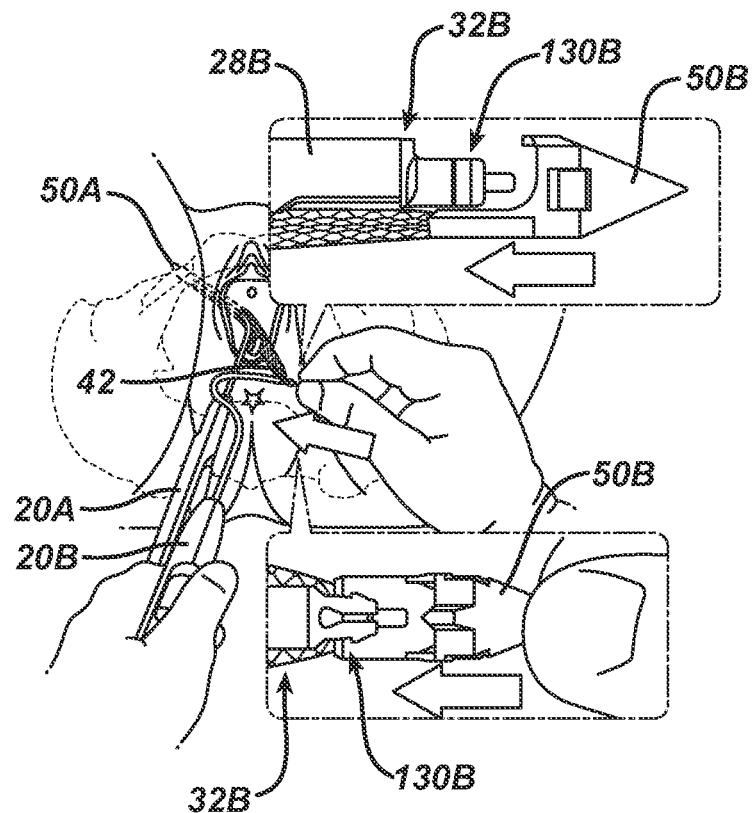

Referring to FIG. 15O, in one embodiment, the left-hand insertion device 20A remains attached to the first insertion tip 50A during the placement of the implant 42 on the patient's second side. In one embodiment, the right-hand insertion device 20B is secured with the second insertion tip 50B by pushing the second insertion tip onto the latching assembly 130B at the distal end 32B of the outer shaft 28B to form a secure connection between the distal end of the right-hand insertion device 20B and the second insertion tip 50B.

Figure 15P:
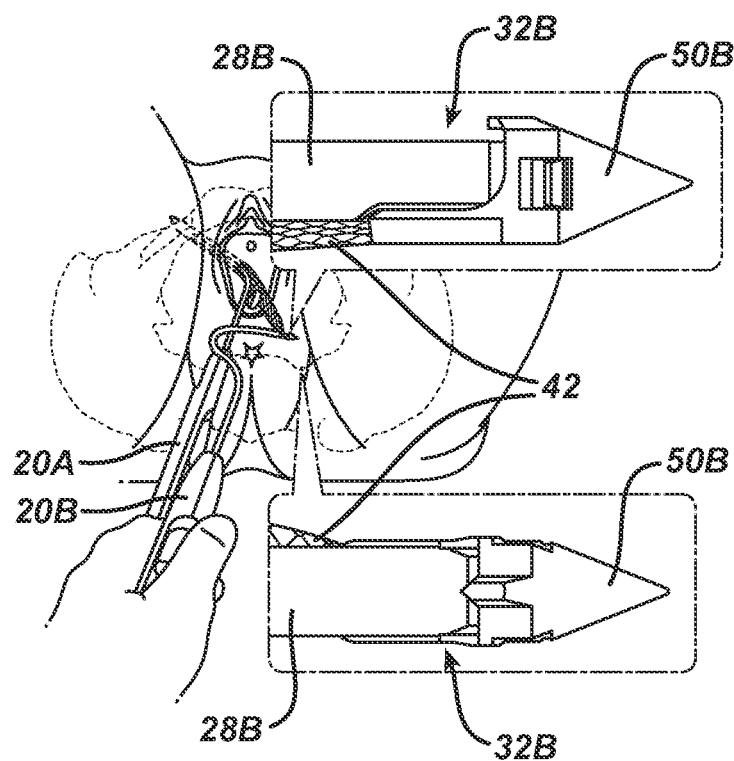

FIG. 15P shows the second insertion tip 50B after it has been secured to the distal end 32B of the outer shaft 28B of the second insertion device 20B. After connection, the surgeon may ensure that the second insertion tip 50B is securely connected by gently pulling upon the second insertion tip. After the second insertion tip 50B has been connected with the second insertion device 20B, the surgeon preferably observes if the implant 42 is twisted. If the implant is twisted, the surgeon preferably removes any twisting to ensure that a twisted portion of the implant is not left under the urethra.

Figure 15Q:
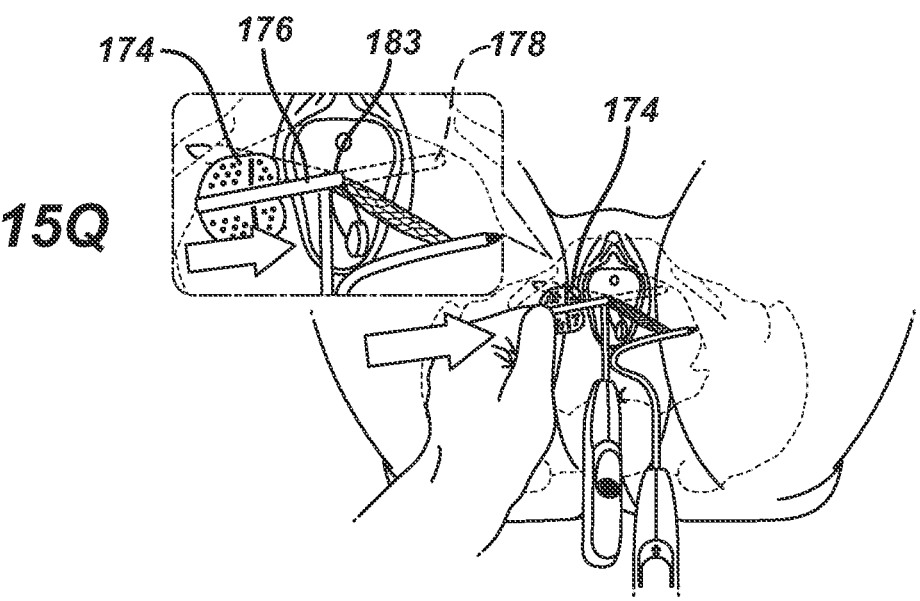

Referring to FIG. 15Q, in one embodiment, the winged guide 174 is inserted into the dissected tract up to the ischio-pubic ramus and slightly into the obturator internus muscle. In one embodiment, the advancement of the distal end of the U-shaped channel 178 of the shaft 176 (FIG. 15H) should be stopped before the shaft 176 perforates the obturator membrane. In one embodiment, the cut-out 183 that defines the insertion zone on the winged guide 174 should be visible during this part of the procedure. Placement of the distal end of the winged guide 174 beyond the insertion zone may allow unintended entry into the obturator membrane or the space of Retzius. If boney contact is not achieved after insertion of the winged guide 174 within the insertion zone, the surgeon should remove and re-evaluate the angle of dissection. If the surgeon encounters difficulty during insertion of the winged guide 174, the surgeon should reconfirm the direction of the dissected tract with a tool such as scissors.

Figure 15R:
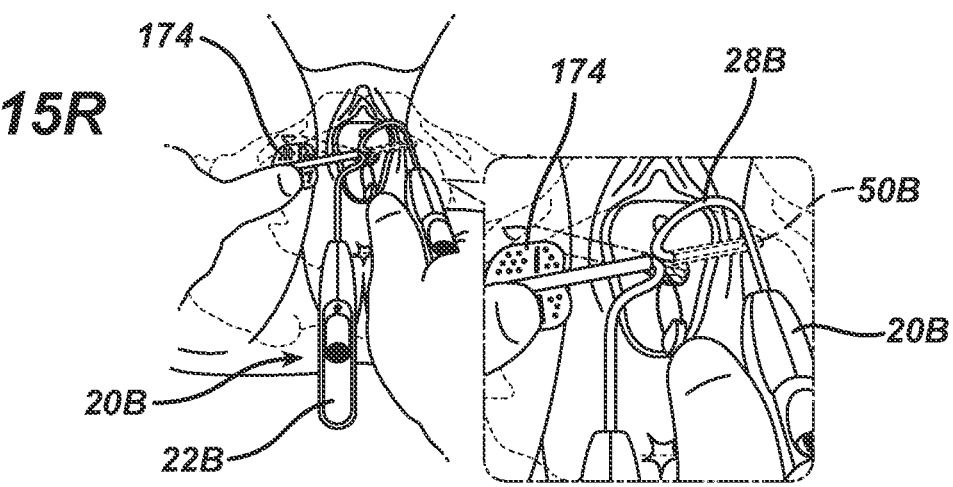

Referring to FIG. 15R, in one embodiment, while the surgeon holds the winged guide 174, the surgeon inserts the right-hand insertion device 20B having the second insertion tip connected therewith into the dissected tract following the U-shaped channel of the winged guide 174 (FIG. 15H). As the distal end 32B of the outer shaft 28B of the right-hand insertion device 20B is placed into the dissected tract, the surgeon preferably ensures that the inserter handle 22B is oriented so that the straight section at the distal end of the outer shaft 28B is aligned with the U-shaped channel 178 in the winged guide 174 (FIG. 15H) and remains in that orientation until the second insertion tip 50B reaches and/or contacts the superior border of the inferior ischio-pubic ramus and is pushed slightly into the obturator internus muscle, such that the second insertion tip 50B does not extend into the obturator membrane.

Figure 15S:
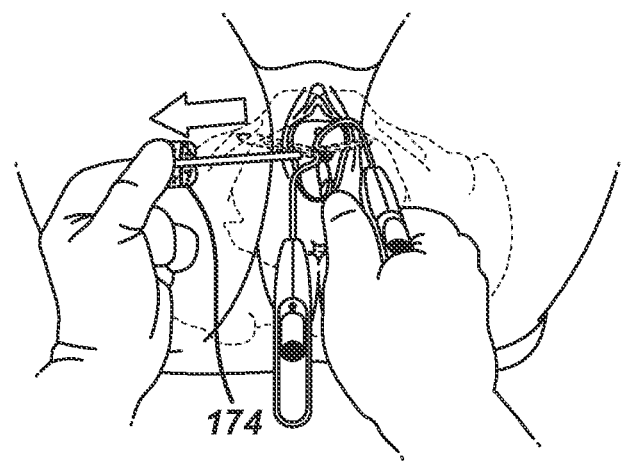

Referring to FIG. 15S, in one embodiment, after the steps shown in FIG. 15P, the surgeon preferably removes the winged guide 174 from the dissected opening.

Figure 15T:
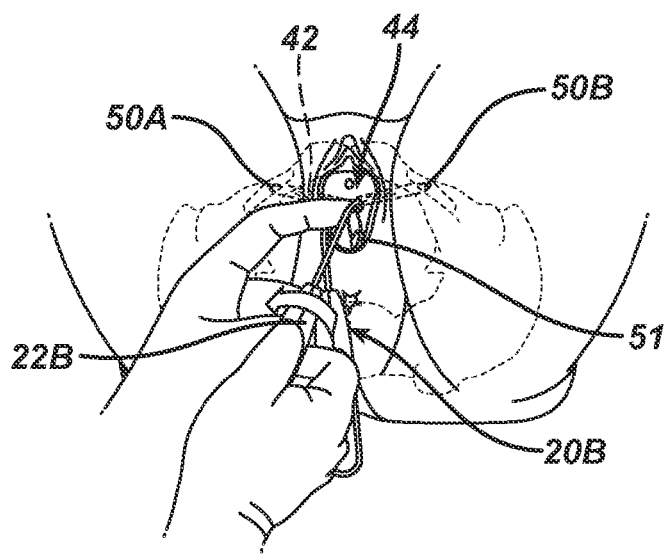

Referring to FIG. 15T, in one embodiment, the surgeon preferably rotates the handle 22B of the right-hand insertion device 20B about its axis until the second insertion tip 50B passes through the obturator membrane and into the obturator externus muscle while the right-hand insertion device maintains contact with the pubic ramus. The central zone 44 of the implant 42 is preferably positioned in close contact to the urethra. The placement loop 51 may aid in the exact placement of the central zone 44 of the implant 42 under the urethra.

In one embodiment, after the first and second insertion tips 50A, 50B have been inserted into tissue at a desired location, a surgeon may perform a cytoscopy.

Figure 15U:
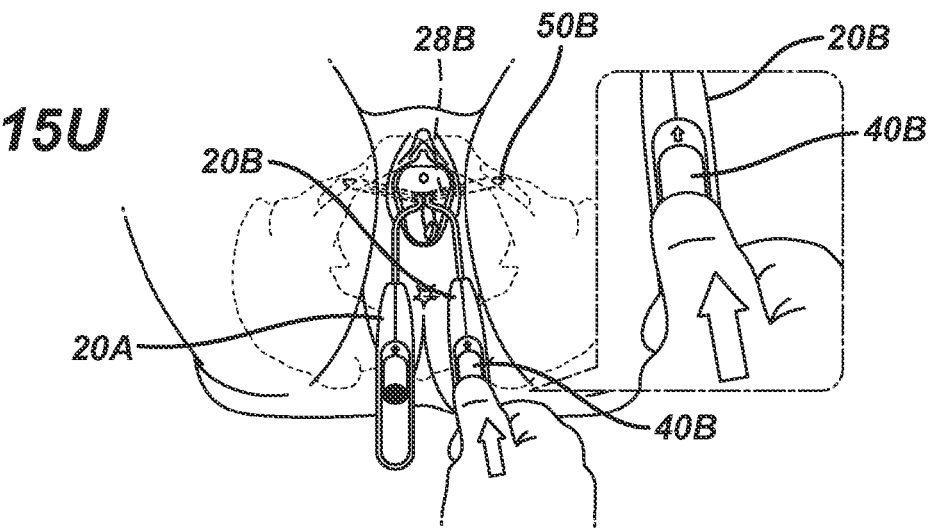

Referring to FIG. 15U, in one embodiment, the second insertion tip 50B is preferably unlocked from the distal end of the right-hand insertion device 20B by pushing the actuator 40B in a distal direction until the surgeon hears an detectable click. As the surgeon pushes the actuator 40B distally, the flexible latching assembly at the distal end of the right-hand insertion device unlocks from the second insertion tip 50B so that the outer shaft 28B of the right-hand insertion device 20B may be retracted through the dissected opening.

In one embodiment, the left-hand insertion device 20A is unlocked from its connection with the first insertion tip 50A and the right-hand insertion device 20B is unlocked from its connection with the second insertion tip 50B. In one embodiment, the surgeon maintains a connection between one of the insertion tips and one of the insertion devices that provides the best option for final adjustment, if necessary.

Figure 15V:
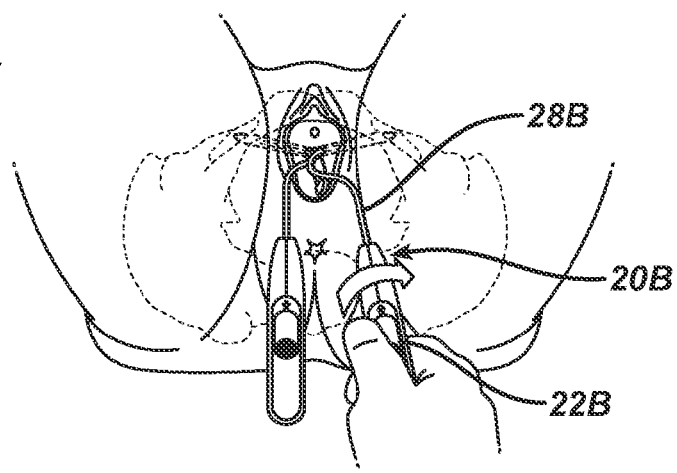

Referring to FIG. 15V, in one embodiment, the right-hand insertion device 20B is removed from the dissected opening by a reverse rotation of the insertion device handle 22B. The outer shaft 28B of the right-hand insertion device 20B preferably follows the entry passage as it is removed from the dissected opening.

Figure 15W:
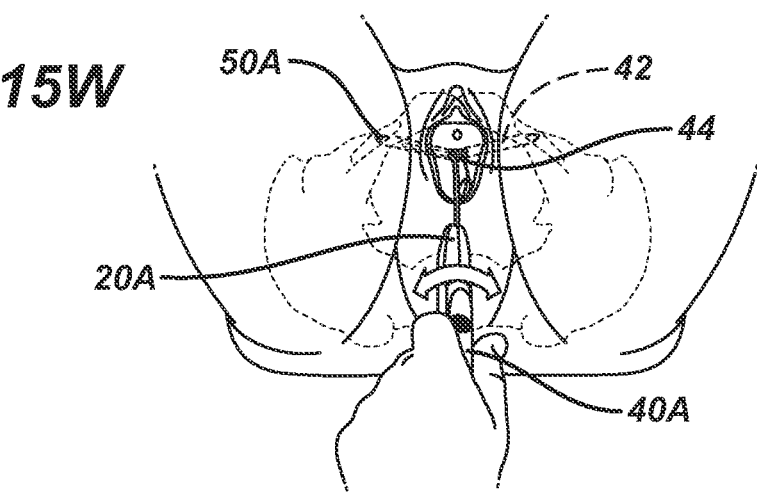

Referring to FIG. 15W, in one embodiment, the appropriate tension provided by the implant 42 is adjusted using the left-hand insertion device 20A. The tension may be adjusted to achieve the desired placement for the central section 44 of the implant 42 relative to the patient's urethra. If the tension on the implant is too high, the surgeon may gently move the first insertion tip 50A and the mesh by pulling the mesh and slowly reversing the inserter or by slightly retracting the left-hand insertion device. After the proper tension level has been obtained, the surgeon preferably unlocks the first insertion tip 50A from the distal end of the left-hand insertion device 20A by pushing the actuator 40A in a distal direction.

Figure 15X:
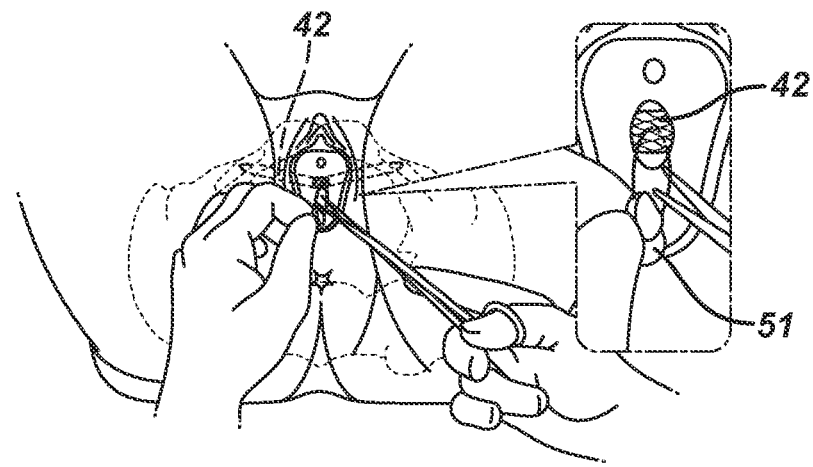
Figure 15Y:
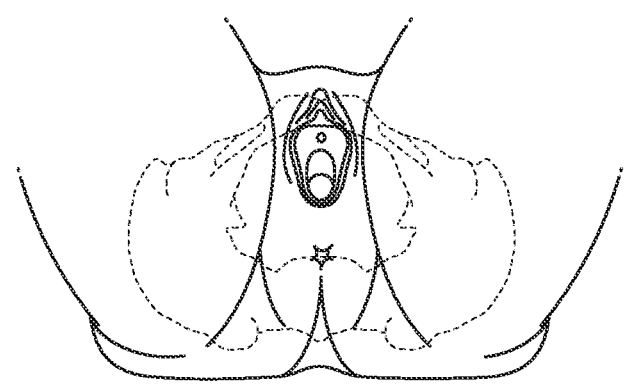

Referring to FIG. 15X, in one embodiment, after the implant 42 has been properly positioned and appropriate tension has been applied, the placement loop 51 may be cut to detach the loop from the implant 42. Referring to FIG. 15Y, in one embodiment, after the step shown in FIG. 15V, the vaginal incision is preferably closed.

Figure 16:
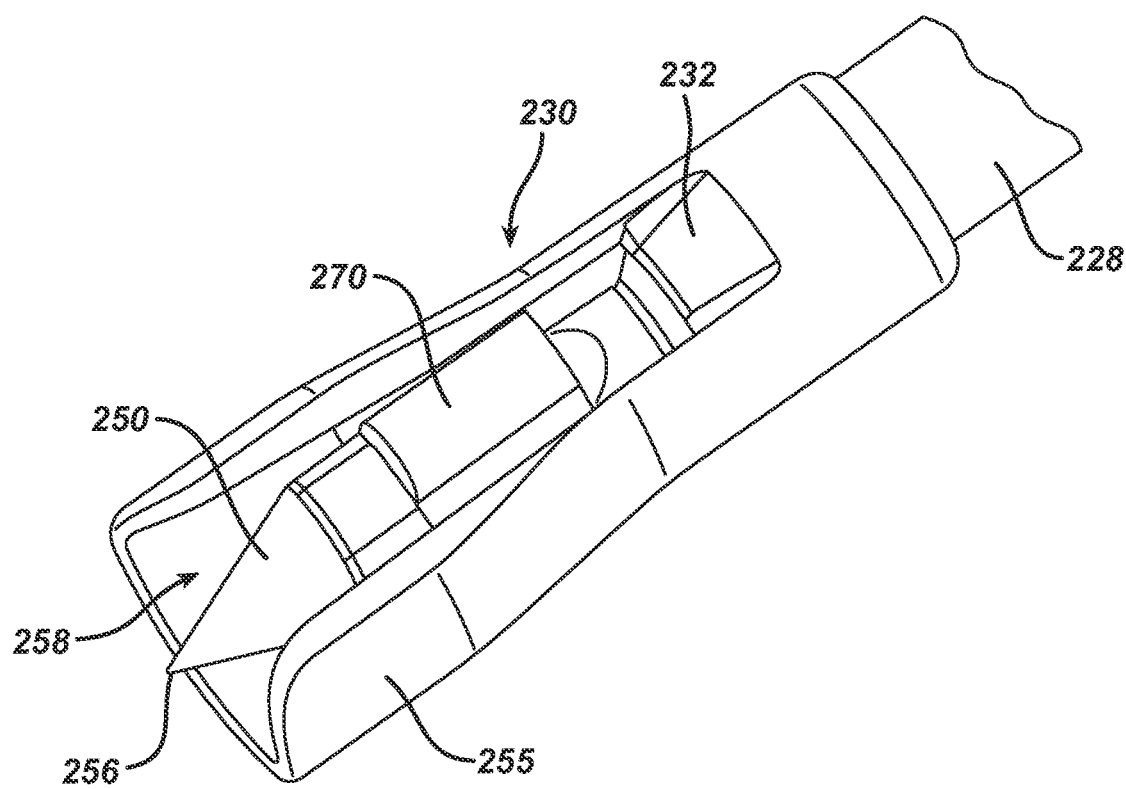
FIG. 16 shows a perspective view of a distal end of an insertion device having a protective shroud that surrounds an insertion tip for an implant, in accordance with one embodiment of the present invention.

Referring to FIG. 16, in one embodiment, an insertion device for an implant desirably includes an outer shaft 228 having a distal end 232 and a flexible or fixed latching assembly 230 provided at the distal end of the insertion device for securing an insertion tip 250 thereto. In one embodiment, a protective shield 255 is secured to the distal end 232 of the outer shaft 228 to isolate the tapered point 256 of the insertion tip 250 from surrounding tissue until the insertion tip has been advanced to a desire location inside a body. In one embodiment, the protective shield 255 preferably includes an elongated opening or slot 258 formed on one side thereof for enabling the implant to be secured to the insertion tip via the hoop 270. In one embodiment, when the insertion tip 250 secured to the distal end of the insertion device has been advanced to a desired location, the protective shield 255 may be manually or automatically retracted to enable the insertion tip to be positioned in tissue at a desired location. In one embodiment, the protective shield 255 may function as a tissue stop to prevent injury to unintended organs or structures.

Figure 17A:
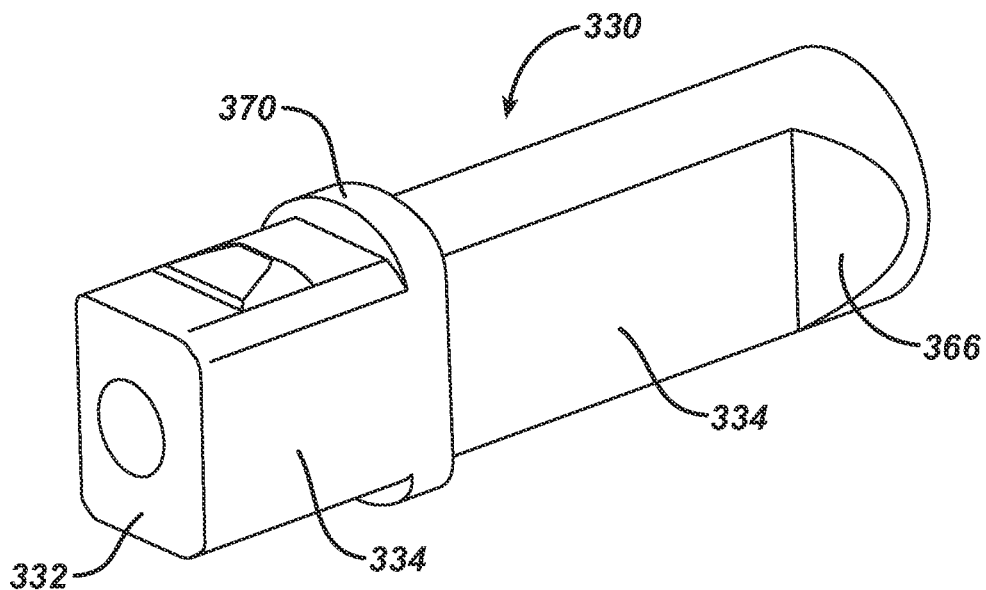
FIG. 17A shows a perspective view of a ground distal end of an insertion device for an implant, in accordance with one embodiment of the present invention.
Figure 17B:
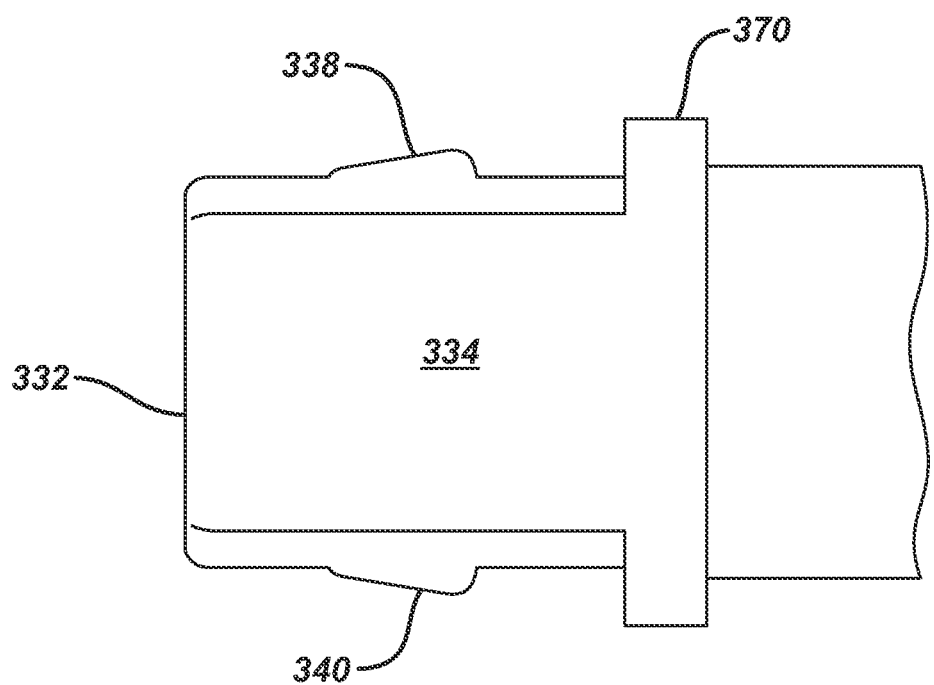
FIG. 17B shows a left side elevation view of the ground distal end of the insertion device shown in FIG. 17A.

Referring to FIGS. 17A and 17B, in one embodiment, an insertion device for an implant preferably includes a distal end having a connector 330 adapted to form a snap-fit connection with an insertion tip, such as the insertion tip described herein. The connector 330 desirably includes a distal end 332 that is insertable into a central lumen of an insertion tip. The connector 330 includes a substantially flat bottom surface 334 that extends in a proximal direction to a sloping surface 366. When an insertion tip is snap-fit onto the end of the connector 330, the flat elongated surface 64 (FIGS. 3A and 3B) of the insertion tip preferably contacts the flat bottom surface 334 of the connector 330. In one embodiment, the sloping surface 336 engages the sloping surface 66 at the proximal end 52 of the tissue connector 50 (FIG. 3B).

The connector includes first and second connecting tabs 338, 340 that are adapted to advance into the opposing windows 62A, 62B of the insertion tip 50 (FIG. 3B). The connector 330 also preferably includes a raised protrusion 370 that engages the central lumen of the insertion tip. In one embodiment, the central lumen of the insertion tip is elastically deformed by the protrusion 370 on the outer surface of the connector 330 as the insertion device moves in a distal direction within the central lumen of the insertion tip. The elastic deformation preferably returns to its original shape when the protrusion 370 on the connector 330 reaches a recessed or widened section toward the distal end of the central lumen of the insertion tip. In one embodiment, the protrusion may reside on the inside of the central lumen of the insertion tip and the corresponding recess may reside on the distal end of the connector.

Referring to FIGS. 17A and 17B, the protrusions 338, 340 adapted to fit into the windows of the insertion tip preferably have a size ranging from 0.002 inches to 0.030 inches, but preferably in the range of 0.010 inches to 0.020 inches. The protrusions 338, 340 may extend the full length of the windows in the insertion tip, or may be of a shorter length depending upon the holding force required between the insertion tip and the connector 330. In one embodiment, the protrusions 338, 340 have a radial surface at a distal end of the protrusions.

Figure 18A:
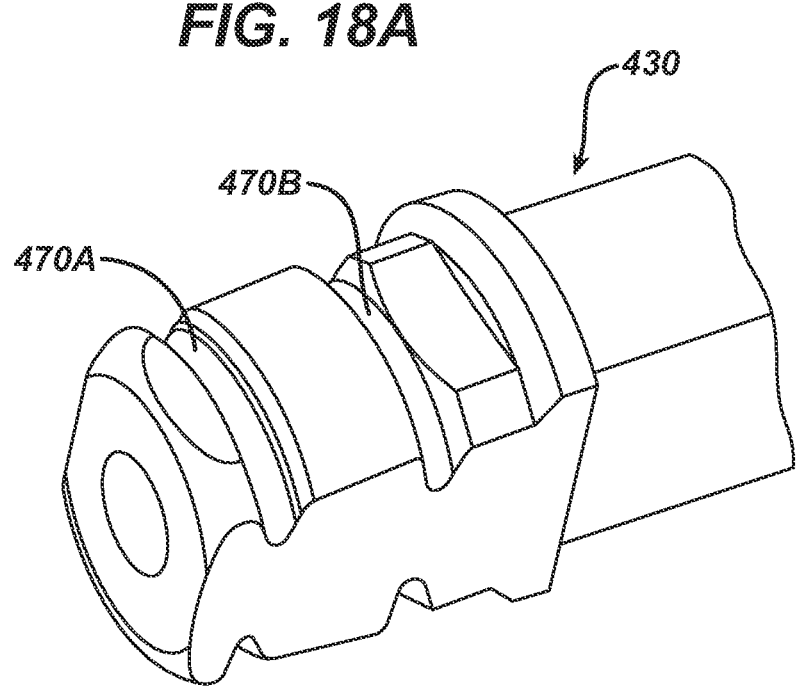
FIG. 18A shows a perspective view of a turned/machined distal end of an insertion device for an implant, in accordance with one embodiment of the present invention.
Figure 18B:
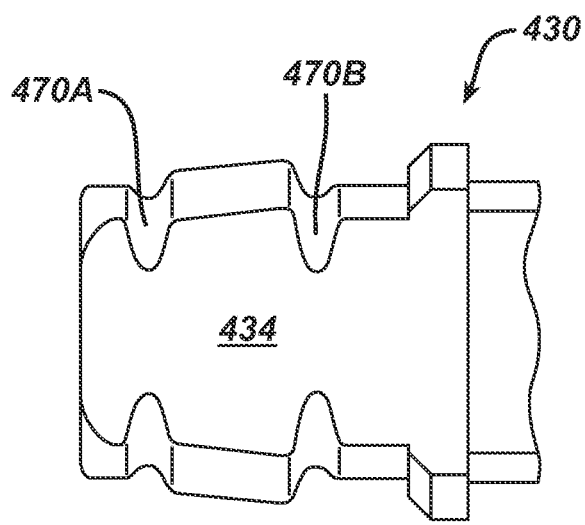
FIG. 18B shows a left side elevation view of the distal end of the insertion device shown in FIG. 18A.
Figure 18C:
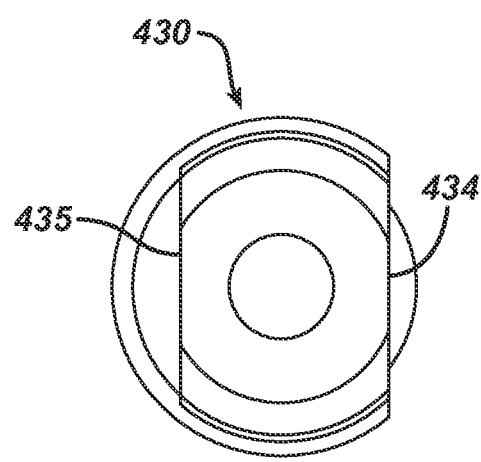
FIG. 18C shows a distal end of the insertion device shown in FIGS. 18A and 18B, in accordance with one embodiment of the present invention.

Referring to FIGS. 18A-18C, in one embodiment, a radial snap-fit connector 430 is provided at a distal end of an insertion device. The connector includes a pair of radial recesses 470A, 470B formed therein, however, other embodiment may have only one radial recess formed therein. In this embodiment, a central lumen of an insertion tip desirably includes a pair of radial protrusions that are adapted to fit into the recesses 470A, 470B for forming a snap fit connection between the insertion tip and the connector 430. The connector has a flat bottom surface 434 that is adapted to be seated against the elongated flat surface 64 of an insertion tip (FIG. 3B). The connector 430 includes a flat top surface 435 that is adapted to be seated against the top wall 86 of the central lumen 60 of the insertion tip (FIG. 3D). The radial snap-fit connector 430 is preferably turned and machined, which allows for ease of manufacture and customizing the fit for both locking and unlocking.

The connectors 330, 430 shown and described in FIGS. 17A-17B and 18A-18C preferably have no moving parts. The snap-fit connectors 330, 430 may be made of plastic, metal or other suitable materials.

Figure 19:
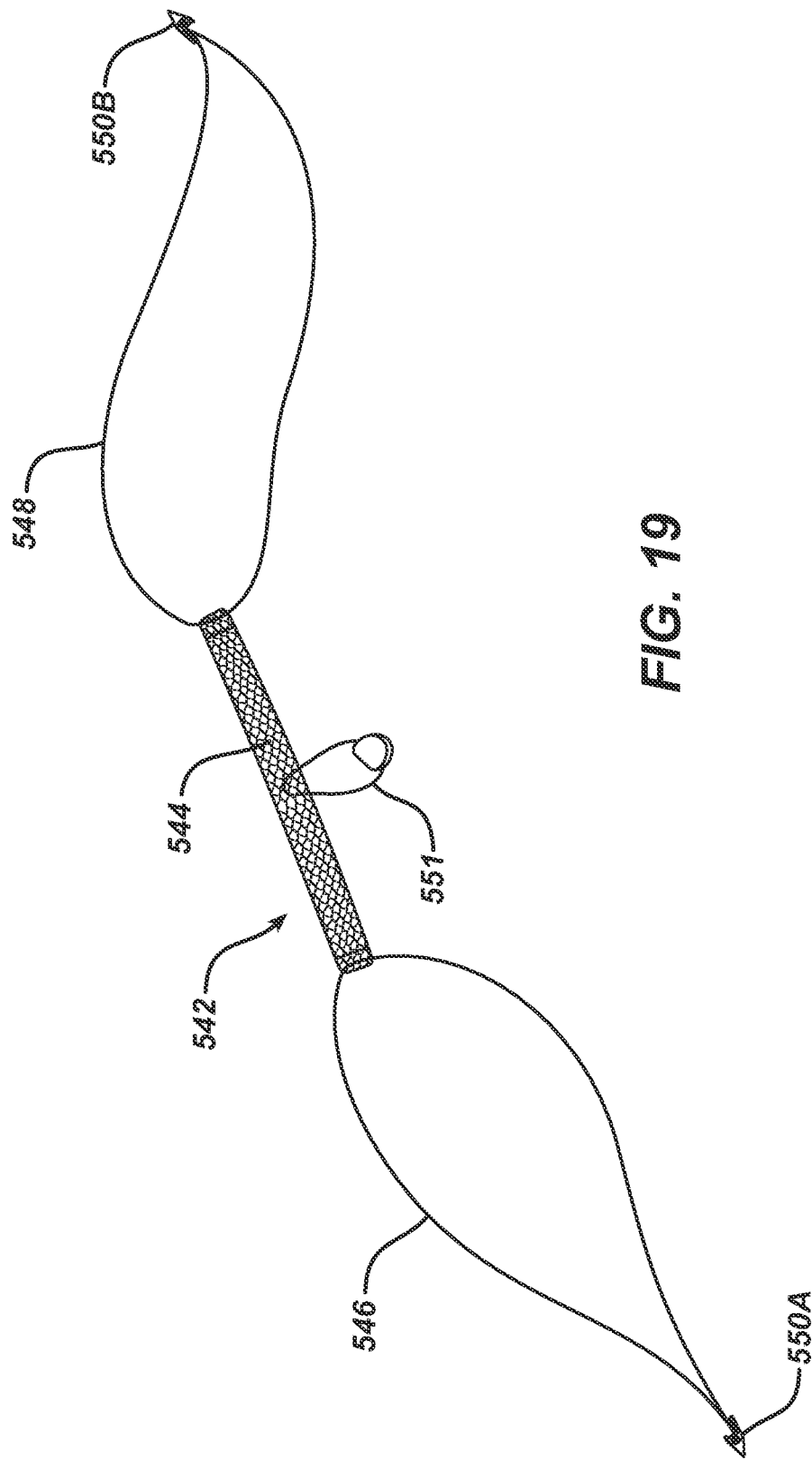
FIG. 19 shows an implant having a central mesh region, first and second suture loops secured to the central mesh region, first and second insertion tips secured to the respective first and second suture loops, and a pull loop, in accordance with one embodiment of the present invention.

Referring to FIG. 19, in one embodiment, an implant 542 preferably has a central mesh region 544 and first and second suture loops 546, 548 that are connected with and extend from opposite ends of the central mesh region 544. The implant 542 desirably includes a first insertion tip 550A that is attached to the outer end of the first suture loop 546 of the implant 542, and a second insertion tip 550B that is attached to the outer end of the second suture loop 548 of the implant 542. The insertion tips 550A, 550B are preferably securable to the distal ends of insertion devices for advancing the implant 542 through tissue for securing the implant at a desired location within the tissue. In one embodiment, plastic sheaths (not shown), such as those used with the Gynecare TVT ABBREVO™ system, may be positioned over the insertion tips and the distal ends of the insertion devices to provide for smooth passage of the insertion tips and the insertion devices through tissue. In one embodiment, the implant 542 preferably includes a placement loop 551 with a button secured to the central region 544 of the implant. In one embodiment, the placement loop has a monofilament loop of PROLENE™ suture with an attached polypropylene button. The loop and the button are pre-assembled as part of the implant at the center of the mesh to aid in the placement of the central region 544 of the mesh under an urethra.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. An implant insertion system comprising:
   an implant;
   at least one insertion tip secured to said implant, coach said at least one insertion tip having a tapered distal end, a proximal end, a base extending proximally from said tapered distal end, and a central lumen formed in said base having an opening facing the proximal end of said insertion tip;
   an insertion device having an outer shaft and a latching assembly provided at a distal end of said outer shaft that is insertable into the opening of the central lumen for selectively locking said insertion tip to said latching assembly, said latching assembly having first and second latches at the distal end thereof defining an outer dimension that is changeable from an expanded state for locking said insertion tip to said latching assembly to a non-expanded state for unlocking said insertion tip from said latching assembly, wherein said first and second latches are elastic, normally flex inwardly toward one another, and have inner cam surfaces that oppose one another; and
   a tip pin disposed within a central opening of said latching assembly that extends between proximal and distal ends of said latching assembly, said tip pin having a shaft with a larger diameter section and a smaller diameter section, wherein said tip pin is moveable toward the proximal end of said latching assembly so that the larger diameter section of said shaft engages said inner cam surfaces for moving said first and second latches away from one another into the expanded state, and wherein said tip pin is moveable toward the distal end of said latching assembly so that the smaller diameter section of said shaft is aligned with said inner cam surfaces whereupon said first and second latches flex inwardly toward one another into the non-expanded state.

2. The implant insertion system as claimed in claim 1, wherein when said latching assembly is in the expanded state the outer dimension of said latching assembly is greater than an inner dimension of the central lumen of said insertion tip.

3. The implant insertion system as claimed in claim 1, wherein when said latching assembly is in the non-expanded state the outer dimension of said latching assembly is less than or equal to an inner dimension of the central lumen of said insertion tip.

4. The implant insertion system as claimed in claim 1, wherein the central lumen of said insertion tip has a width, and wherein said latching assembly is wider than the width of the central lumen when said latching assembly is in the expanded state and narrower than or equal to the width of the central lumen when said latching assembly is in the non-expanded state.

5. The implant insertion system as claimed in claim 1, wherein said latching assembly has said proximal end attached to the distal end of said outer shaft, and wherein said first and second latches have respective first and second latch posts that project away from one another.

6. The implant insertion system as claimed in claim 1, further comprising first and second windows formed in said base of said insertion tip, wherein said first and second windows are formed in opposing side walls of said base of said insertion tip, and wherein said first and second windows oppose one another and intersect with the central lumen formed in said base of said insertion tip.

7. The implant insertion system as claimed in claim 6, wherein said base of said insertion tip further comprises a blind pocket at a distal end of said central lumen and distal to said first and second windows, wherein said blind pocket is adapted to receive latch extensions at distal ends of said first and second latches when said insertion tip is secured to said latching assembly.

8. The implant insertion system as claimed in claim 7, wherein in the expanded state said first and second latch posts extend into said first and second windows in said base of said insertion tip for locking said insertion tip to said latching assembly.

9. The implant insertion system as claimed in claim 8, said tip pin having a proximal end, a distal end, said shaft extending between the proximal and distal ends, a reduced diameter neck formed in said smaller diameter section of said shaft, and an annular base at the proximal end of said tip pin, wherein said reduced diameter neck of said tip pin has a diameter that is smaller than the larder diameter section of said shaft located at the proximal and distal ends of said tip pin, and said annular base of said tip pin has a diameter that is greater than the larder diameter section of said shaft at the proximal and distal ends of said tip pin and greater than the diameter of said central opening of said latching assembly.

10. The implant insertion system as claimed in claim 9, wherein said tip pin comprises metal and is freely moveable within the central opening of said latching assembly for sliding in proximal and distal directions within the central opening of said latching assembly.

11. The implant insertion system as claimed in claim 9, wherein said first and second latches have said inner cam surfaces that slide over the outer surface of said tip pin shaft, wherein when said latching assembly is in the non-expanded state, the distal end of said tip pin is distal to the distal end of said latching assembly and said inner cam surfaces of said first and second latches are in contact with said reduced diameter neck of said tip pin, and when said latching assembly is in the expanded state the distal end of said tip pin is aligned with the distal end of said latching assembly and said inner cam surfaces of said first and second latches are in contact with the larder diameter section of said tip pin shaft adjacent the distal end of said tip pin.

12. The implant insertion system as claimed in claim 11 wherein said insertion device further comprises:
- a handle having a proximal end and a distal end, wherein a proximal end of said outer shaft is secured to the distal end of said handle;
- an actuator provided on said handle and being moveable between the proximal and distal ends of said handle, said actuator having a ramp and said handle having a flexible element that engages said ramp for generating a detectable click when said actuator is moved to a distal-most position for indicating that said latching assembly is in the non-expanded state.

13. The implant insertion system as claimed in claim 12, further comprising:
- said outer shaft having an elongated conduit extending between the proximal and distal ends thereof; and
- a push wire disposed within the elongated conduit of said outer shaft and being moveable in distal and proximal directions relative to said outer shaft, said push wire having a proximal end opposing said actuator and a distal end opposing said annular base of said tip pin, wherein said push wire is not connected with said actuator or said tip pin, and wherein said push wire is free to slide in distal and proximal directions within the elongated conduit of said outer shaft.

14. The implant insertion system as claimed in claim 13, wherein said outer shaft comprises metal, said latching assembly comprises a polymer material, said tip pin comprises metal, said implant comprises mesh or a mesh and suture combination, said insertion tip comprises a polymer, and said push wire is flexible and is selected from the group of materials consisting of stainless steel, polymers, nylon, Teflon, polypropylene and combinations thereof.

15. The implant insertion system as claimed in claim 13, wherein said insertion tip is locked onto said latching assembly by placing the central lumen of said insertion tip over the distal end of said latching assembly and pushing said insertion tip toward the proximal end of said latching assembly for forcing said tip pin to move proximally, which, in turn, urges said first and second latches away from one another.

16. The implant insertion system as claimed in claim 15, wherein said insertion tip is unlocked from said latching assembly by moving said actuator toward the distal end of said handle, which, in turn, urges said push wire distally for contacting said annular base of said tip pin, which, in turn, urges said tip pin distally for aligning said reduced diameter neck of said tip pin with said inner cam surfaces of said first and second latches so that said first and second latches are free to flex inwardly toward one another, wherein when said actuator moves from a proximal-most position to a distal-most position said actuator travels about 4-5 times more than said push wire.

17. The implant insertion system as claimed in claim 1, wherein the central lumen of said insertion tip has a blind pocket adjacent a distal end of said base, a top wall that defines an upper surface of the central lumen, a bottom wall that defines a lower surface of the central lumen, and opposing side walls extending between the top and bottom walls of the central lumen, and wherein said base of said insertion tip has first and second windows that extend through the side walls of the central lumen.

18. The implant insertion system as claimed in claim 17, wherein said insertion tip includes an elongated flat surface that extends proximally from the bottom wall of the central lumen to the proximal end of said insertion tip, wherein when said latching assembly is inserted into the central lumen said latching assembly has a flat bottom surface that engages the bottom wall of the central lumen and the distal end of said outer shaft has a flat surface that engages said elongated flat surface that extends proximally from the bottom wall of said central lumen to the proximal end of said insertion tip.

19. The implant insertion system as claimed in claim 18, wherein said insertion tip further comprises a hoop provided under said elongated flat surface adjacent the proximal end of said insertion tip, said hoop having a hoop opening for receiving an end of said implant, wherein said hoop is collapsible and meltable for conforming to an outer profile of said insertion tip.

20. The implant insertion system as claimed in claim 19, wherein said hoop has opposing sidewalls with weakened sections that enable said opposing sidewalls to collapse inwardly toward one another for capturing said implant within said collapsed hoop.

21. The implant insertion system as claimed in claim 18, wherein said latching assembly has a flat top surface that engages the top wall of the central lumen of said insertion tip when said flat bottom surface of said latching assembly engages the bottom wall of the central lumen of said insertion tip for providing rotational stability for said insertion tip when said insertion tip is locked to a distal end of said insertion device.

22. An implant insertion system comprising:
- an implant having a central section and first and second arms extending from opposite sides of said central section;
- a first insertion tip secured to said first arm of said implant and a second insertion tip secured to said second arm of said implant, each said insertion tip having a tapered distal end, a proximal end, a base extending proximally from said tapered distal end, and a central lumen formed in said base having an opening facing the proximal end of said insertion tip;
- a first insertion device for securing said first insertion tip and a second insertion device for securing said second insertion tip, each said insertion device having an outer shaft and a latching assembly provided at a distal end of said outer shaft that is insertable into the opening of the central lumen of one of said insertion tips for selectively locking the one of said insertion tips to said latching assembly, said latching assembly having first and second latches at the distal end thereof defining an outer dimension that is changeable from an expanded state for locking the one of said insertion tips to said latching assembly to a non-expanded state for unlocking the one of said insertion tips from said latching assembly;
- a tip pin disposed within a central opening of said latching assembly, said tip pin being free to slide distally and proximally within the central opening of said latching assembly;
- a push wire disposed within said outer shaft and being free to slide distally and proximally within said outer shaft, wherein a distal end of said push wire opposes a proximal end of said tip pin, and wherein said tip pin and said push wire are not connected and are free to slide relative to one another in distal and proximal directions.

23. The implant insertion system as claimed in claim 22, wherein said first insertion device comprises a left-hand insertion device for securing said first insertion tip and said second insertion device comprises a right-hand insertion device for securing said second insertion tip.

24. The implant insertion system as claimed in claim 23, wherein when said left-hand and right-hand insertion devices are secured to said first and second insertion tips, respectively, said outer shaft of said left-hand insertion device has a distal end that curves to the left and said outer shaft of said right-hand insertion device has a distal end that curves to the right and away from the distal end of said outer shaft of said left-hand insertion device.

25. The implant system as claimed in claim 22, wherein said first and second latches are elastic, normally flex inwardly toward one another, and have inner cam surfaces that oppose one another, wherein said tip pin has a shaft with a larger diameter section and a smaller diameter section proximal to the larger diameter section, wherein said tip pin is moveable proximally toward the proximal end of said latching assembly so that the larger diameter section of said shaft engages said inner cam surfaces for moving said first and second latches away from one another into the expanded state, and wherein said tip pin is moveable distally toward the distal end of said latching assembly so that the smaller diameter section of said shaft is aligned with said inner cam surfaces whereupon said first and second latches flex inwardly toward one another into the non-expanded state.

26. A method of treating urinary incontinence comprising:
providing a mesh implant having a central section and first and second arms extending from opposite sides of said central section, said mesh implant having a first insertion tip secured to said first arm and a second insertion tip secured to said second arm, each said insertion tip having a tapered distal end, a proximal end, a base extending proximally from said tapered distal end, and a central lumen formed in said base having an opening facing the proximal end of said insertion tip;
providing a first insertion device having a first outer shaft and a first latching assembly having first and second latches at the distal end thereof defining an outer dimension that is changeable from a non-expanded state to an expanded state, wherein said first and second latches are elastic, normally flex inwardly toward one another, and have inner cam surfaces that oppose one another;
disposing a tip pin within a central opening of said first latching assembly, said tip pin having a shaft with a larger diameter section and a smaller diameter section;
inserting said first latching assembly into the central lumen of said first insertion tip so that said first insertion tip engages a distal end of said tip pin for moving said tip pin toward the proximal end of said first latching assembly so that the larger diameter section of said shaft engages said inner cam surfaces of said first and second latches for moving said first and second latches away from one another for changing the outer dimension of said first latching assembly to the expanded state for locking said first insertion tip to said first latching assembly;
providing a second insertion device having a second outer shaft and a second latching assembly having first and second latches at the distal end thereof defining an outer dimension that is changeable from a non-expanded state to an expanded state, wherein said first and second latches of said second latching assembly are elastic, normally flex inwardly toward one another, and have inner cam surfaces that oppose one another; and
inserting said second latching assembly into the central lumen of said second insertion tip so that said second insertion tip engages a distal end of said second tip pin for moving said second tip pin toward the proximal end of said second latching assembly so that the larger diameter section of said shaft of said second tip pin engages said inner cam surfaces for moving said first and second latches of said second latching assembly away from one another for changing the outer dimension of said second latching assembly to the expanded state for locking said second insertion tip to said second latching assembly.

27. The method as claimed in claim 26, further comprising:
forming a surgical opening in tissue;
while said first insertion tip is locked to said first insertion device, inserting said first insertion tip into the surgical opening for positioning said first insertion tip at a first location in the tissue;
while said second insertion tip is locked to said second insertion device, inserting said second insertion tip into the surgical opening for positioning said second insertion tip in a second location in the tissue;
changing the outer dimension of said second insertion device from the expanded state to the non-expanded state for unlocking said second insertion tip from said second insertion device;
while said first insertion tip remains locked to said first insertion device, moving the location of said first insertion tip to a third location in the tissue for adjusting the location of said central section of said mesh implant.

28. The method as claimed in claim 27, further comprising pushing said first insertion tip into the tissue and pulling said first insertion tip out of the tissue while said first insertion tip remains locked to said first latching assembly.

29. The method as claimed in claim 28, further comprising after the pushing and pulling, changing the outer dimension of said first insertion device from the expanded state to the non-expanded state for unlocking said first insertion tip from said first insertion device.

* * * * *